US011524983B2

(12) United States Patent
Liu et al.

(10) Patent No.: US 11,524,983 B2
(45) Date of Patent: Dec. 13, 2022

(54) EVOLUTION OF *BT* TOXINS

(71) Applicants: President and Fellows of Harvard College, Cambridge, MA (US); Monsanto Company, St. Louis, MO (US)

(72) Inventors: David R. Liu, Lexington, MA (US); Ahmed Hussein Badran, Dorchester, MA (US); Victor Guzov, Cambridge, MA (US); Tom Malvar, North Stonington, CT (US); Prashanth Vishwanath, Arlington, MA (US); Jeff Nageotte, Billerica, MA (US); Qing Huai, Winchester, MA (US); Melissa Kemp, Medford, MA (US)

(73) Assignees: President and Fellows of Harvard College, Cambridge, MA (US); Monsanto Company, St. Louis, MO (US)

( * ) Notice: Subject to any disclaimer, the term of this patent is extended or adjusted under 35 U.S.C. 154(b) by 111 days.

(21) Appl. No.: 15/217,839

(22) Filed: Jul. 22, 2016

(65) Prior Publication Data
US 2017/0029473 A1 Feb. 2, 2017
US 2018/0057545 A9 Mar. 1, 2018

Related U.S. Application Data

(60) Provisional application No. 62/305,497, filed on Mar. 8, 2016, provisional application No. 62/196,253, filed on Jul. 23, 2015.

(51) Int. Cl.
*C07K 14/325* (2006.01)
*A01N 63/50* (2020.01)
*C12N 15/10* (2006.01)
*C12N 15/82* (2006.01)

(52) U.S. Cl.
CPC ............ *C07K 14/325* (2013.01); *A01N 63/50* (2020.01); *C12N 15/1058* (2013.01); *C12N 15/8286* (2013.01)

(58) Field of Classification Search
None
See application file for complete search history.

(56) References Cited

U.S. PATENT DOCUMENTS

| 5,057,432 A | 10/1991 | Wangersky et al. |
| 5,223,409 A | 6/1993 | Ladner et al. |
| 5,658,727 A | 8/1997 | Barbas et al. |
| 5,712,089 A | 1/1998 | Borrebaeck et al. |
| 5,821,047 A | 10/1998 | Garrard et al. |
| 5,880,275 A | 3/1999 | Fischhoff et al. |
| 5,965,124 A | 10/1999 | Feinberg et al. |
| 6,033,874 A | 3/2000 | Baum et al. |
| 6,156,509 A | 12/2000 | Schellenberger |
| 6,429,298 B1 | 8/2002 | Ellington et al. |
| 6,713,063 B1 | 3/2004 | Malvar et al. |
| 6,962,705 B2 | 11/2005 | Malvar et al. |
| 6,969,731 B1 | 11/2005 | Tang et al. |
| 7,064,249 B2 | 6/2006 | Corbin et al. |
| 7,070,982 B2 | 7/2006 | Malvar et al. |
| 9,023,594 B2 | 5/2015 | Liu et al. |
| 9,228,207 B2 | 1/2016 | Liu et al. |
| 9,267,127 B2 | 2/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,394,537 B2 | 7/2016 | Liu et al. |
| 9,526,784 B2 | 12/2016 | Liu et al. |
| 9,567,589 B2 | 2/2017 | Jin et al. |
| 9,737,604 B2 | 8/2017 | Jin et al. |
| 9,766,216 B2 | 9/2017 | Wada et al. |
| 9,771,574 B2 | 9/2017 | Liu et al. |
| 10,179,911 B2 | 1/2019 | Liu et al. |
| 10,227,581 B2 | 3/2019 | Liu et al. |
| 10,336,997 B2 | 7/2019 | Liu et al. |
| 10,392,674 B2 | 8/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,920,208 B2 | 2/2021 | Liu et al. |
| 11,046,948 B2 | 6/2021 | Liu et al. |
| 11,078,469 B2 | 8/2021 | Liu et al. |
| 11,104,967 B2 | 8/2021 | Liu et al. |
| 11,214,792 B2 | 1/2022 | Liu et al. |
| 11,299,729 B2 | 4/2022 | Badran et al. |

(Continued)

FOREIGN PATENT DOCUMENTS

| EP | 0289479 A2 | 11/1988 |
| EP | 3115457 A1 | 1/2017 |

(Continued)

OTHER PUBLICATIONS

Cao et al., J Agric Food Chem 59:8550-59 (2011).*
International Preliminary Report on Patentability for PCT/US2016/043559, dated Feb. 1, 2018.
International Preliminary Report on Patentability for PCT/US2016/044546, dated Feb. 8, 2018.
International Preliminary Report on Patentability for PCT/US2016/043513, dated Feb. 1, 2018.
Invitation to Pay Additional Fees for PCT/US2018/14867, dated Apr. 5, 2018.
Badran et al., In vivo continuous directed evolution. Curr Opin Chem Biol. Feb. 2015;24:1-10. doi: 10.1016/j.cbpa.2014.09.040. Epub Nov. 7, 2014.

(Continued)

*Primary Examiner* — Russell T Boggs
(74) *Attorney, Agent, or Firm* — Wolf, Greenfield & Sacks, P.C.

(57) ABSTRACT

The disclosure provides amino acid sequence variants of *Bacillus thuringiensis* (Bt) toxins and methods of producing the same. Some aspects of this disclosure provide methods for generating Bt toxin variants by continuous directed evolution. Some aspects of this disclosure provide compositions and methods for pest control using the disclosed variant Bt toxins.

20 Claims, 26 Drawing Sheets

Specification includes a Sequence Listing.

(56) References Cited

U.S. PATENT DOCUMENTS

| | | |
|---|---|---|
| 2002/0132327 A1 | 9/2002 | Hay et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2005/0019753 A1 | 1/2005 | Kukolj et al. |
| 2005/0100973 A1 | 5/2005 | Steward et al. |
| 2006/0112447 A1 | 5/2006 | Bogdanova et al. |
| 2006/0160222 A1 | 7/2006 | Rozwadowski et al. |
| 2006/0166319 A1 | 7/2006 | Chan et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2010/0297180 A1 | 11/2010 | Shone |
| 2011/0177495 A1 | 7/2011 | Liu et al. |
| 2011/0318385 A1 | 12/2011 | Jackson et al. |
| 2012/0128649 A1 | 5/2012 | Chaddock et al. |
| 2013/0059931 A1 | 3/2013 | Petersen-Mahrt et al. |
| 2013/0117869 A1 | 5/2013 | Duchateau et al. |
| 2013/0345064 A1 | 12/2013 | Liu et al. |
| 2013/0345065 A1 | 12/2013 | Liu et al. |
| 2014/0201858 A1 | 7/2014 | Ostertag et al. |
| 2015/0056177 A1 | 2/2015 | Liu et al. |
| 2015/0259721 A1 | 9/2015 | Van Brunt et al. |
| 2015/0275202 A1 | 10/2015 | Liu et al. |
| 2016/0002301 A1 * | 1/2016 | Je ............................ A01N 63/02 424/93.2 |
| 2016/0201040 A1 | 7/2016 | Liu et al. |
| 2016/0348096 A1 | 12/2016 | Liu et al. |
| 2017/0009224 A1 | 1/2017 | Liu et al. |
| 2017/0029473 A1 | 2/2017 | Liu et al. |
| 2017/0029844 A1 | 2/2017 | Ball et al. |
| 2017/0044520 A1 | 2/2017 | Liu et al. |
| 2017/0233708 A1 | 8/2017 | Liu et al. |
| 2018/0087046 A1 | 3/2018 | Liu et al. |
| 2018/0237758 A1 | 8/2018 | Liu et al. |
| 2019/0219575 A1 | 7/2019 | Gray et al. |
| 2019/0256842 A1 | 8/2019 | Liu et al. |
| 2019/0276816 A1 | 9/2019 | Liu et al. |
| 2019/0276873 A1 | 9/2019 | Dong et al. |
| 2020/0071722 A1 | 3/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2021/0163924 A1 | 6/2021 | Packer et al. |
| 2021/0238569 A1 | 8/2021 | Liu et al. |
| 2021/0261938 A1 | 8/2021 | Liu et al. |

FOREIGN PATENT DOCUMENTS

| | | |
|---|---|---|
| JP | H0937764 A | 2/1997 |
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |
| WO | WO 96/04403 A1 | 2/1996 |
| WO | WO 98/32845 A1 | 7/1998 |
| WO | WO 00/71694 A1 | 11/2000 |
| WO | WO 01/05950 A2 | 1/2001 |
| WO | WO 2001/038547 A2 | 5/2001 |
| WO | WO 01/61049 A1 | 8/2001 |
| WO | WO 2005/081632 A2 | 9/2005 |
| WO | WO 07/066923 A1 | 6/2007 |
| WO | WO 08/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/039518 A2 | 4/2011 |
| WO | WO 2011/147590 A2 | 12/2011 |
| WO | WO 2011/066747 A1 | 6/2012 |
| WO | WO 2012/088381 A2 | 6/2012 |
| WO | WO 2012/138927 A2 | 10/2012 |
| WO | WO 2013/047844 | 4/2013 |
| WO | WO2014/157820 A1 * | 2/2014 |
| WO | WO 2014/039585 A2 | 3/2014 |
| WO | WO 2014/157820 A1 | 10/2014 |
| WO | WO 2014/158593 A1 | 10/2014 |
| WO | WO 2015/134121 A2 | 9/2015 |
| WO | WO 2015/193897 A1 | 12/2015 |
| WO | WO 2016/077052 A9 | 5/2016 |
| WO | WO 2016/168631 A1 | 10/2016 |
| WO | WO 2017/015559 A2 | 1/2017 |
| WO | WO 2017/070632 A2 | 4/2017 |
| WO | WO 2018/009903 A2 | 1/2018 |
| WO | WO 2018/027078 A1 | 2/2018 |
| WO | WO 2018/039438 A1 | 3/2018 |
| WO | WO 2018/109447 A1 | 6/2018 |
| WO | WO 2018/136939 A1 | 7/2018 |
| WO | WO 2019/040935 A1 | 2/2019 |
| WO | WO 2019/067815 A2 | 4/2019 |

OTHER PUBLICATIONS

Dickinson et al., A system for the continuous directed evolution of proteases rapidly reveals drug-resistance mutations. Nat Commun. Oct. 30, 2014;5:5352. doi: 10.1038/ncomms6352.

Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.

Maeder et al., Robust, synergistic regulation of human gene expression using TALE activators. Nat Methods. Mar. 2013;10(3):243-5. doi: 10.1038/nmeth.2366. Epub Feb. 10, 2013.

Extended European Search Report for EP 09812363, dated Mar. 30, 2012.

Extended European Search Report for EP 16 20 3684, dated May 26, 2017.

International Search Report and Written Opinion for PCT/US2009/056194, dated Jun. 21, 2010.

International Preliminary Report on Patentability for PCT/US2009/056194, dated Mar. 17, 2011.

Extended European Search Report for EP 17 16 0955, dated May 16, 2017.

Invitation to Pay Additional Fees for PCT/US2011/066747, dated Aug. 30, 2012.

International Search Report and Written Opinion for PCT/US2011/066747, dated Oct. 30, 2012.

International Preliminary Report on Patentability for PCT/US2011/066747, dated Jul. 4, 2013.

International Search Report and Written Opinion for PCT/US2015/012022, dated Sep. 25, 2015.

International Preliminary Report on Patentability for PCT/US2015/012022, dated Aug. 4, 2016.

Invitation to Pay Additional Fees for PCT/US/2016/043559, dated Jan. 12, 2017.

International Search Report and Written Opinion for PCT/US/2016/043559, dated Mar. 10, 2017.

International Search Report and Written Opinion for PCT/US2015/057012, dated Jun. 10, 2016.

International Preliminary Report on Patentability for PCT/US2015/057012, dated May 4, 2017.

International Search Report and Written Opinion for PCT/US2016/027795, dated Aug. 11, 2016.

International Preliminary Report on Patentability for PCT/US2016/027795, dated Oct. 26, 2017.

Invitation to Pay Additional Fees for PCT/US2016/044546, dated Oct. 12, 2016.

International Search Report and Written Opinion for PCT/US2016/044546, dated Dec. 28, 2016.

International Search Report and Written Opinion for PCT/US2016/043513, dated Nov. 30, 2016.

(56) References Cited

OTHER PUBLICATIONS

Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Badran et al., Development of potent in vivo mutagenesis plasmids with broad mutational spectra. Nat Commun. Oct. 7, 2015;6:8425. doi: 10.1038/ncomms9425.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23 2002;41(16):5144-9.
Buchholz et al., Alteration of Cre recombinase site specificity by substrate-linked protein evolution. Nat Biotechnol. Nov. 2001;19(11):1047-52.
Caldwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dickinson et al., Experimental interrogation of the path dependence and stochasticity of protein evolution using phage-assisted continuous evolution. Proc Natl Acad Sci USA. May 2013;110(22):9007-12.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Durai et al., A bacterial one-hybrid selection system for interrogating zinc finger-DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.

(56) References Cited

OTHER PUBLICATIONS

Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and Escherichia coli expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., Escherichia coli one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat—a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Latimer et al., Specificity of monoclonal antibodies produced against phosphorothioate and ribo modified DNAs. Mol Immunol. Oct. 1995;32(14-15):1057-64.
Leconte et al., A population-based experimental model for protein evolution: effects of mutation rate and selection stringency on evolutionary outcomes. Biochemistry. Feb. 26, 2013;52(8): 1490-1499.
Lincoln et al., Self-sustained replication of an RNA enzyme. Science. Feb. 27, 2009;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Lutz et al., Creating multiple-crossover DNA libraries independent of sequence identity. Proc Natl Acad Sci U S A. Sep. 25, 2001;98(20):11248-53. Epub Sep. 18, 2001.
Makeyev et al., Evolutionary potential of an RNA virus. J Virol. Feb. 2004;78(4):2114-20.
Malmborg et al., Selective phage infection mediated by epitope expression on F pilus. J Mol Biol. Oct. 31, 1997;273(3):544-51.
Martin et al., Kinetic analysis of T7 RNA polymerase-promoter interactions with small synthetic promoters. Biochemistry. May 19, 1987;26(10):2690-6.
McCafferty et al., Phage antibodies: filamentous phage displaying antibody variable domains. Nature. Dec. 6, 1990;348(6301):552-4.
McConnell et al., Constrained peptide libraries as a tool for finding mimotopes. Gene. Dec. 30, 1994;151(1-2):115-8.
Milligan et al., Oligoribonucleotide synthesis using T7 RNA polymerase and synthetic DNA templates. Nucleic Acids Res. Nov. 11, 1987;15(21):8783-98.
Mills et al., An extracellular Darwinian experiment with a self-duplicating nucleic acid molecule. Proc Natl Acad Sci U S A. Jul. 1967;58(1):217-24.
Nelson et al., Filamentous phage DNA cloning vectors: a noninfective mutant with a nonpolar deletion in gene III. Virology. Jan. 30, 1981;108(2):338-50.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
O'Maille et al., Structure-based combinatorial protein engineering (SCOPE). J Mol Biol. Aug. 23, 2002;321(4):677-91.
Opperman et al., A model for a umuDC-dependent prokaryotic DNA damage checkpoint. Proc Natl Acad Sci U S A. Aug. 3, 1999;96(16):9218-23.
Ostendorf et al., Characterization of a dam mutant of Serratia marcescens and nucleotide sequence of the dam region. J Bacteriol. Jul. 1999;181(13):3880-5.
Ostermeier e al., A combinatorial approach to hybrid enzymes independent of DNA homology. Nat Biotechnol. Dec. 1999;17(12):1205-9.

(56) References Cited

OTHER PUBLICATIONS

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Rakonjac et al., Filamentous phage are released from the bacterial membrane by a two-step mechanism involving a short C-terminal fragment of pIII. J Mol Biol. Jun. 25, 1999;289(5):1253-65.
Rakonjac et al., Filamentous phage infection-mediated gene expression: construction and propagation of the gIII deletion mutant helper phage R408d3. Gene. Oct. 1, 1997;198(1-2):99-103.
Rakonjac et al., Roles of pIII in filamentous phage assembly. J Mol Biol. Sep. 11, 1998;282(1):25-41.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rebar et al., Phage display methods for selecting zinc finger proteins with novel DNA-binding specificities. Methods Enzymol. 1996;267:129-49.
Reidhaar-Olson et al., Random mutagenesis of protein sequences using oligonucleotide cassettes. Methods Enzymol. 1991;208:564-86.
Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.
Riechmann et al., The C-terminal domain of TolA is the coreceptor for filamentous phage infection of *E. coli*. Cell. Jul. 25, 1997;90(2):351-60.
Ringquist et al., Translation initiation in *Escherichia coli*: sequences within the ribosome-binding site. Mol Microbiol. May 1992;6(9):1219-29.
Rosenberg et al., T7 Select® Phage Display System: A Powerful new protein display system based on bacteriophage T7. Innovations. 1996;6:1-6.
Santini et al., Efficient display of an HCV cDNA expression library as C-terminal fusion to the capsid protein D of bacteriophage lambda. J Mol Biol. Sep. 11, 1998;282(1):125-35.
Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'-->P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. AIDS Res Hum Retroviruses. Sep. 1, 2001;17(13):1249-55.
Sieber et al., Libraries of hybrid proteins from distantly related sequences. Nat Biotechnol. May 2001;19(5):456-60.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsuji et al., Random multi-recombinant PCR for the construction of combinatorial protein libraries. Nucleic Acids Res. Oct. 15, 2001;29(20):E97.
Tzagoloff et al., The Initial Steps in Infection With Coliphage M13. Virology. Nov. 1964;24:372-80.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
International Search Report and Written Opinion for PCT/US2014/052231, dated Jan. 30, 2015.
International Preliminary Report on Patentability for PCT/US2014/052231, dated Mar. 3, 2016.
International Search Report and Written Opinion for PCT/US2018/14867, dated May 23, 2018.
International Preliminary Report on Patentability for PCT/US2018/14867 dated Aug. 1, 2019.
International Search Report and Written Opinion for PCT/US2018/051557, dated Feb. 25, 2019.
International Search Report and Written Opinion for PCT/US2018/044242, dated Nov. 21, 2018.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Komor et al., Programmable editing of a target base in genomic DNA without double-stranded DNA cleavage. Nature. May 19, 2016;533(7603):420-4. doi: 10.1038/nature17946. Epub Apr. 20, 2016.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Miller et al., A TALE nuclease architecture for efficient genome editing. Nat Biotechnol. Feb. 2011;29(2):143-8. doi:10.1038/nbt.1755. Epub Dec. 22, 2010.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

(56) References Cited

OTHER PUBLICATIONS

Yamamoto et al., Virological and immunological bases for HIV-1 vaccine design. Uirusu 2007;57(2):133-139. https://doi.org/10.2222/jsv.57.133.
PCT/US2014/052231, Jan. 30, 2015, International Search Report and Written Opinion.
PCT/US2014/052231, Mar. 3, 2016, International Preliminary Report on Patentability.
PCT/US2018/14867, May 23, 2018, International Search Report and Written Opinion.
PCT/US2018/14867, Aug. 1, 2019, International Preliminary Report on Patentability.
PCT/US2018/051557, Feb. 25, 2019, International Search Report and Written Opinion.
PCT/US2018/044242, Nov. 21, 2018, International Search Report and Written Opinion.
International Preliminary Report on Patentability, dated Dec. 24, 2020, in connection with Application No. PCT/US2019/037216.
Invitation to Pay Additional Fees, dated Oct. 13, 2020, in connection with Application No. PCT/US2020/042016.
International Search Report and Written Opinion, dated Dec. 10, 2020, in connection with Application No. PCT/US2020/042016.
[No Author Listed] Genbank Submission. NCBI; Accession No. WP_010869888, version WP_010869888.1. tyrosine—tRNA ligase [Methanocaldococcus jannaschii]. Jun. 1, 2019.
Genbank Submission. NCBI; Accession No. WP_011033391, version WP_011033391.1. pyrrolysine—tRNA(Pyl) ligase [Methanosarcina mazei]. Polycarpo et al.; Nov. 29, 2019.
Genbank Submission. NCBI; Accession No. WP_011305865, version WP_011305865.1. pyrrolysine—tRNA(Pyl) ligase [Methanosarcina barkeri].Polycarpo et al.; Nov. 29, 2019.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626. Epub Jun. 21, 2009.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Bade et al., Botulinum neurotoxin type D enables cytosolic delivery of enzymatically active cargo proteins to neurones via unfolded translocation intermediates. J Neurochem. Dec. 2004;91(6):1461-72.
Binz et al., Clostridial neurotoxins: mechanism of SNARE cleavage and outlook on potential substrate specificity reengineering. Toxins. Apr. 2010;2(4):665-82. Epub Apr. 13, 2010.
Box et al., A multi-domain protein system based on the HC fragment of tetanus toxin for targeting DNA to neuronal cells. J Drug Target. Jul. 2003;11(6):333-43. doi: 10.1080/10611860310001634667.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.
Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.
Chaineau et al., Multiple roles of the vesicular-SNARE TI-VAMP in post-Golgi and endosomal trafficking. FEBS Letters. Oct. 2009;583:3817-26.
Chen et al., Engineering botulinum neurotoxin to extend therapeutic intervention. PNAS. Jun. 2009;106(23):9180-4.
Chen et al., SNARE-mediated membrane fusion. Nat Rev Mol Cell Biol. Feb. 2001;2(2):98-106.
Chen et al., VAMP8 facilitates cellular proliferation and temozolomide resistance in human glioma cells. Neuro-Oncology. 2015;17(3):407-18. Epub Sep. 10, 2014.
Chin, Expanding and reprogramming the genetic code of cells and animals. Annu Rev Biochem. 2014;83:379-408. doi: 10.1146/annurev-biochem-060713-035737. Epub Feb. 10, 2014.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. 2013; 339:819-23.
Craik et al., Proteases as therapeutics. Biochem J. Apr. 2011;435(1):16 pages.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.
Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.
Feng et al., Exo1: A new chemical inhibitor of the exocytic pathway. PNAS. May 2003;100(11):6469-74.
Ferretti et al., Complete genome sequence of an M1 strain of *Streptococcus* pyogenes. Proc Natl Acad Sci U S A. Apr. 10, 2001;98(8):4658-63. doi: 10.1073/pnas.071559398.
Foster et al., Re-engineering the target specificity of Clostridial neurotoxins—A route to novel therapeutics. Neurotoxicity Research. May 2006;9(2,3):101-7.
Foster et al., Targeted Secretion Inhibitors—Innovative Protein Therapeutics. Toxins. Dec. 2010;2:2795-815.
Fu et al., Promises and Pitfalls of Intracellular Delivery of Proteins. Bioconjugate Chemistry. Aug. 2014;25:1602-8.
Gill, Bacterial Toxins: a Table of Letal Amounts. Microbiological Reviews. Mar. 1982;46(1):86-94.
Goodnough et al., Development of a delivery vehicle for intracellular transport of botulinum neurotoxin antagonists. FEBS Lett. Feb. 27, 2002;513(2-3):163-8.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.
Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.
Hedstrom et al., Converting trypsin to chymotrypsin: the role of surface loops. Science. Mar. 1992;255(5049):1249-53.
Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.
Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jankovic et al., Direct selection and phage display of a Gram-positive secretome. Genome Biology. Dec. 13, 2007; 8(266):1-15.
Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.
Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.

(56) References Cited

OTHER PUBLICATIONS

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.

Köhler, A yeast-based growth assay for the analysis of site-specific proteases. Nucleic Acids Res. 2003;31(4):e16. 5 pages.

Lebeda et al., The Zinc-Dependent Protease Activity of the Botulinum Neurotoxins. Toxins. May 2010;2:978-97.

Liu et al., Adding new chemistries to the genetic code. Annu Rev Biochem. 2010;79:413-44. doi: 10.1146/annurev.biochem.052308.105824.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.

Mali et al., RNA-guided human genome engineering via Cas9. Science. 2013; 339:823-26.

Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.

Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.

O'Donoghue et al., Upgrading protein synthesis for synthetic biology. Nat Chem Biol. Oct. 2013;9(10):594-8. doi: 10.1038/nchembio.1339.

Pickett et al., Towards New Uses of Botulinum Toxin as a Novel Therapeutic Tool. Toxins. Jan. 2011;3:63-81.

Pogson et al., Engineering Next Generation Proteases. Curr Opin Biotechnol. Aug. 2009;20(4):390-7.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.

Sikorra et al., Substrate Recognition Mechanism of VAMP/Synaptobrevin-cleaving Clostridial Neurotoxins. Journal of Biological Chemistry. 2008;283:21145-52. Epub May 29, 2008.

Somm et al., A botulinum toxin—drived targeted secretion inihibitor downregulates the GH/IGF1 axis. The Journal of Clinical Investigation. Sep. 2012;122(9):3295-306.

Steffen et al., MT1-MMP-Dependent Invasion Is Regulated by TI-VAMP/VAMP7. Current Biology. Jun. 2008;18:926-31.

Tsai et al., Targeting botulinum neurotoxin persistence by the ubiquitin-proteasome system. PNAS. Sep. 2010;107(38):16554-9.

Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.

Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.

Varadarajan et al., Engineering of protease variants exhibiting high catalytic activity and exquisite substrate selectivity. PNAS. May 2005;102(19):6855-60.

Varadarajan et al., Highly active and selective endopeptidases with programmed substrate specificities. Nat Chem Biol. May 2008;4(5):290-4.

Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.

Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.

Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.

Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.

Yeh et al., Retargeted Clostridial neurotoxins as Novel Agents for Treating Chronic Diseases. Biochemistry. Nov. 2011;50:10419-21.

Yi et al., Engineering of TEV protease variants by yeast ER sequestration screening (YESS) of combinatorial libraries. PNAS. Apr. 2013;110(18):7229-34.

Ziemann et al., Gene name errors are widespread in the scientific literature. Genome Biol. Aug. 23, 2016;17(1):177. doi: 10.1186/s13059-016-1044-7.

Invitation to Pay Additional Fees for PCT/US2018/040692 dated Sep. 12, 2018.

International Search Report and Written Opinion for PCT/US2018/040692 dated Nov. 15, 2018.

International Preliminary Report on Patentability for PCT/US2018/040692 dated Jan. 16, 2020.

Invitation to Pay Additional Fees for PCT/US2018/051557, dated Jan. 4, 2019.

International Preliminary Report on Patentability for PCT/US2018/051557, dated Apr. 2, 2020.

International Search Report and Written Opinion for Application No. PCT/US2019/037216 dated Sep. 4, 2019.

Invitation to Pay Additional Fees for Application No. PCT/US 18/48134 dated Nov. 19, 2018.

International Search Report and Written Opinion for Application No. PCT/US 18/48134 dated Jan. 22, 2019.

International Preliminary Report on Patentability for Application No. PCT/US 18/48134 dated Mar. 5, 2020.

[No Author Listed] NCBI Accession No. XP_015843220.1. C ->U editing enzyme APOBEC-1 [Peromyscus maniculatus bairdii], XP002793540.

[No Author Listed] NCBI Accession No. XP_021505673.1. C ->U editing enzyme APOBEC-1 [Meriones unguiculatus], XP002793541.

Cattaneo et al., SEL1L affects human pancreatic cancer cell cycle and invasiveness through modulation of PTEN and genes related to cell-matrix interactions. Neoplasia. 2005;7(11):1030-1038.

Chen, Clinical uses of botulinum neurotoxins: current indications, limitations and future developments. Toxins (Basel). 2012;4(10):913-939.

Deribe, Mechanistic insights into the role of truncating PREX2 mutations in melanoma. Mol Cell Oncol. 2016;3(3):e1160174.

Guzman et al., Tight regulation, modulation, and high-level expression by vectors containing the arabinose PBAD promoter. J Bacteriol. 1995;177(14):4121-4130.

Harris et al., Measurement of enzyme activity. Methods Enzymol. 2009;463:57-71.

Hendricks et al., The *S. cerevisiae* Mag1 3-methyladenine DNA glycosylase modulates susceptibility to homologous recombination. DNA Repair (Amst). 2002;1(8):645-659.

Kim et al., DJ-1, a novel regulator of the tumor suppressor PTEN. Cancer Cell. 2005;7(3):263-273.

Kim et al., Increasing the genome-targeting scope and precision of base editing with engineered Cas9-cytidine deaminase fusions. Nature Biotechnology; Feb. 13, 2007; 35(4): 371-376.

Laskowska et al., IbpA and IbpB, the new heat-shock proteins, bind to endogenous *Escherichia coli* proteins aggregated intracellularly by heat shock. Biochimie. 1996;78(2):117-22.

(56) References Cited

OTHER PUBLICATIONS

Lu, The destructive effect of botulinum neurotoxins on the SNARE protein: SNAP-25 and synaptic membrane fusion. PeerJ. 2015;3:e1065. Published Jun. 30, 2015.
Masuyer et al., Engineered botulinum neurotoxins as new therapeutics. Annu Rev Pharmacol Toxicol. 2014;54:27-51.
Mihai et al., PTEN inhibition improves wound healing in lung epithelia through changes in cellular mechanics that enhance migration. Am J Physiol Lung Cell Mol Physiol. 2012;302(3):L287-L299.
Oeemig et al., Solution structure of DnaE intein from Nostoc punctiforme: structural basis for the design of a new split intein suitable for site-specific chemical modification. FEBS Lett. May 6, 2009;583(9):1451-6.
Rawlings et al., MEROPS: the database of proteolytic enzymes, their substrates and inhibitors. Nucleic Acids Res. Jan. 2014;42(Database issue):D503-9.
Wang et al., Continuous directed evolutions of proteins with improved soluble expression. Nature Chemical Biology. Nat Publishing Group. Aug. 20, 2018; 14(10):972-980.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
Partial European Search Report for Application No. 18847527.1, dated Apr. 21, 2021.
Extended European Search Report for Application No. 18847527.1, dated Aug. 2, 2021.
International Preliminary Report on Patentability dated Jan. 27, 2022, in connection with Application No. PCT/US2020/042016.
Blum, Continuous evolution of bacterial neurotoxins for intracellular protease therapy. 2019. Poster. 1 page.
Blum, Generation of selective botulinum neurotoxin proteases with reprogrammed substrate specificity through phage-assisted directed evolution. Jun. 4, 2019. Powerpoint. 24 pages.
Blum, Generation of selective botulinum neurotoxin proteases with reprogrammed substrate specificity through phage-assisted directed evolution. Apr. 7, 2020. Powerpoint. 36 pages.
Blum et al., Phage-assisted evolution of botulinum neurotoxin proteases with reprogrammed specificity. Science. Feb. 19, 2021;371(6531):803-810. doi: 10.1126/science.abf5972.
Kasai et al., Distinct initial SNARE configurations underlying the diversity of exocytosis. Physiol Rev. Oct. 2012;92(4):1915-64. doi: 10.1152/physrev.00007.2012.
Liu et al., PTEN deletion enhances the regenerative ability of adult corticospinal neurons. Nat Neurosci. Sep. 2010;13(9):1075-81. doi: 10.1038/nn.2603. Epub Aug. 8, 2010.
Meng et al., Role of SNARE proteins in tumourigenesis and their potential as targets for novel anti-cancer therapeutics. Biochim Biophys Acta. Aug. 2015;1856(1):1-12. doi: 10.1016/j.bbcan.2015.04.002. Epub May 5, 2015.
Nicholson-Fish et al., VAMP4 Is an Essential Cargo Molecule for Activity-Dependent Bulk Endocytosis. Neuron. Dec. 2, 2015;88(5):973-984. doi: 10.1016/j.neuron.2015.10.043. Epub Nov. 19, 2015.
Raingo et al., VAMP4 directs synaptic vesicles to a pool that selectively maintains asynchronous neurotransmission. Nat Neurosci. Mar. 11, 2012;15(5):738-45. doi: 10.1038/nn.3067.
Ruiz-Martinez et al., YKT6 expression, exosome release, and survival in non-small cell lung cancer. Oncotarget. Aug. 9, 2016;7(32):51515-51524. doi: 10.18632/oncotarget.9862.
Zhang et al., Identification and characterization of a novel botulinum neurotoxin. Nat Commun. Aug. 3, 2017;8:14130. doi: 10.1038/ncomms14130.
PCT/US2018/040692, Nov. 15, 2018, International Search Report and Written Opinion.
PCT/US2018/040692, Jan. 16, 2020, International Preliminary Report on Patentability.
PCT/US2018/051557, Jan. 4, 2019, Invitation to Pay Additional Fees.
PCT/US2018/051557, Apr. 2, 2020, International Preliminary Report on Patentability.
PCT/US2019/037216, Sep. 4, 2019, International Search Report and Written Opinion.
PCT/US18/481134, Nov. 19, 2018, Invitation to Pay Additional Fees.
PCT/US18/481134, Jan. 22, 2019, International Search Report and Written Opinion.
PCT/US18/481134, Mar. 5, 2020, International Preliminary Report on Patentability.

\* cited by examiner

FIG. 2

H. virescens
H. armigera
P. gossypiella
T. ni

H. virescens    TGVLTLNFQPTASMHGMFEF
H. armigera     TGVLSLNFQPTAAMHGMFEF
P. gossypiella       TGVLILRIQPTASMQGMFEF
T. ni           SGVLSLNMNPLDTMVGMFEF
TBR3            SGVLSLNFNPSATMVGMFEF B. mori   H. armigera   H. virescens   M. sexta Domain III:
Sugar binding Domain I:
Pore formation Cry1Ac Domain II:
Receptor binding

FIG. 5
Round 2: intermediate stringency/moderate mutagenesis
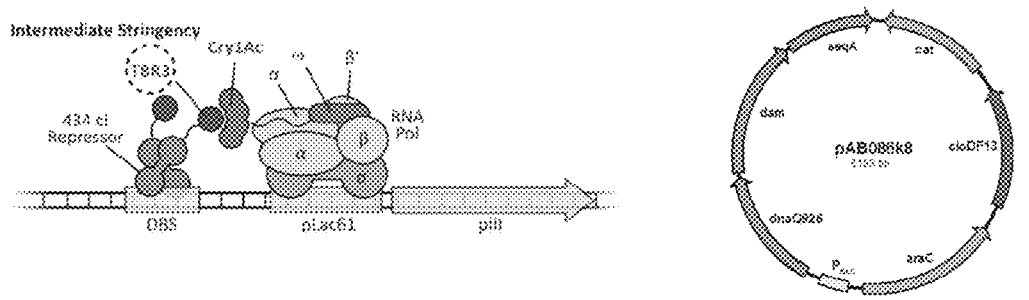
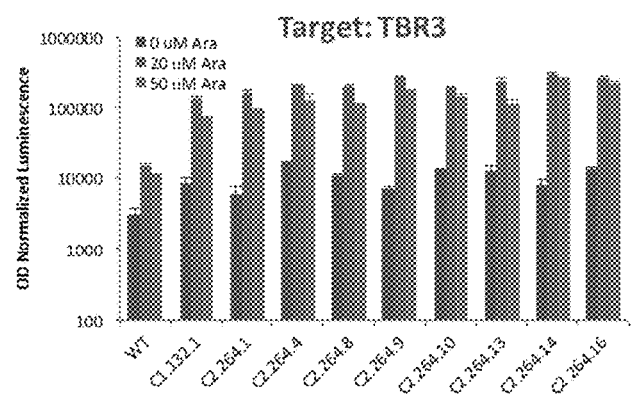

FIG. 9
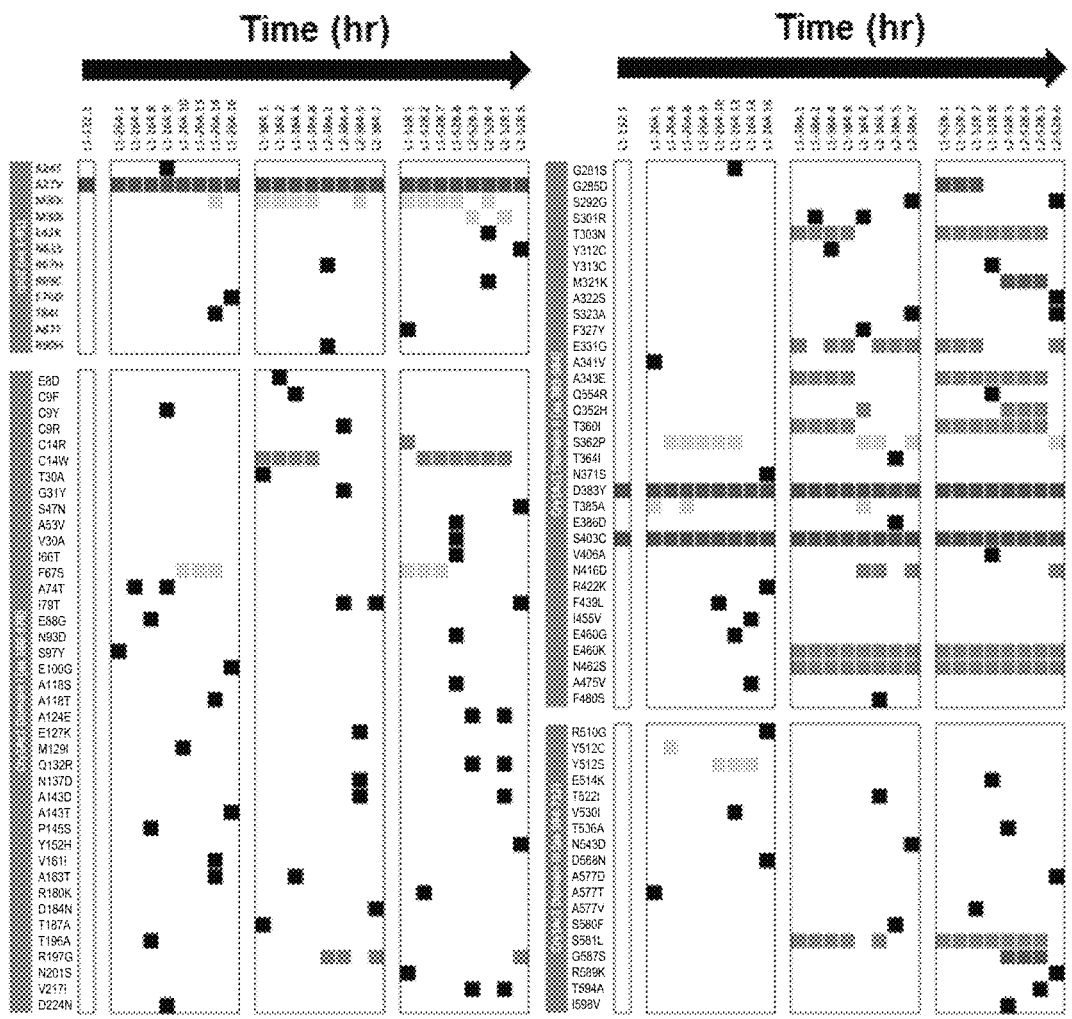
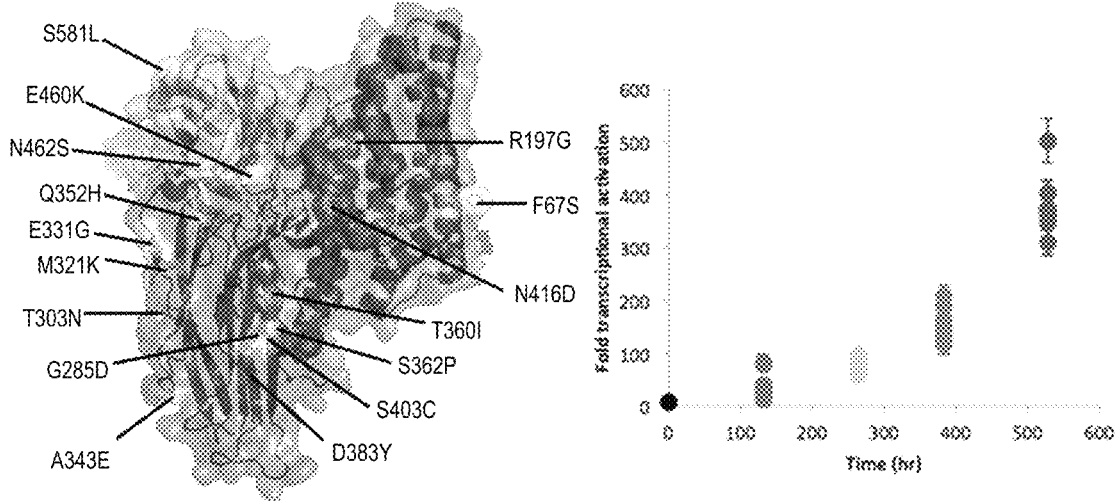

FIG. 10
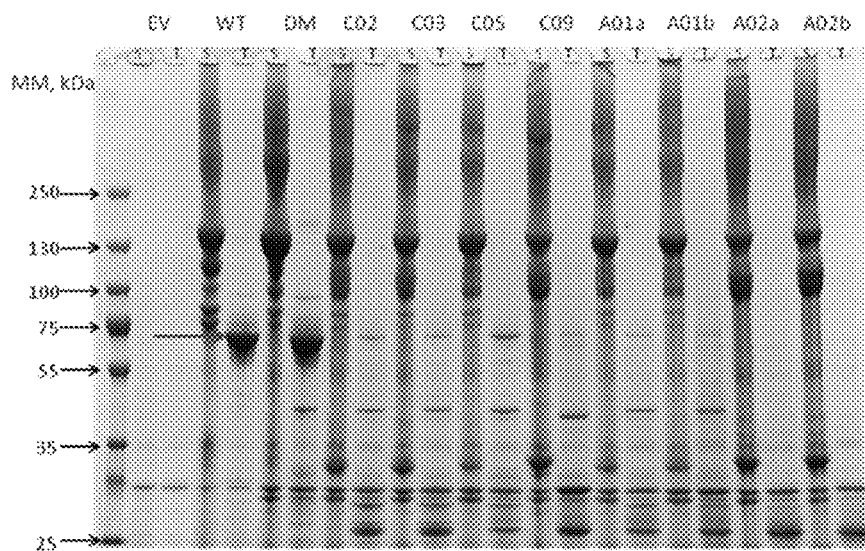
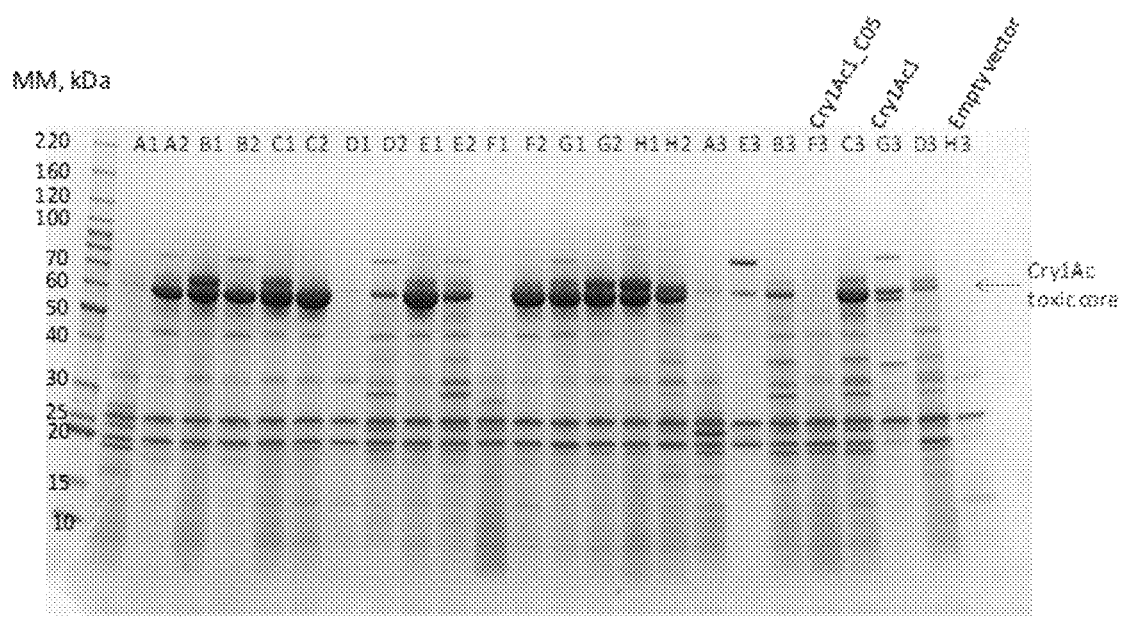

PACE-evolved variant activity – *T. ni* larva

FIG. 14
PACE-evolved variant activity – affinity
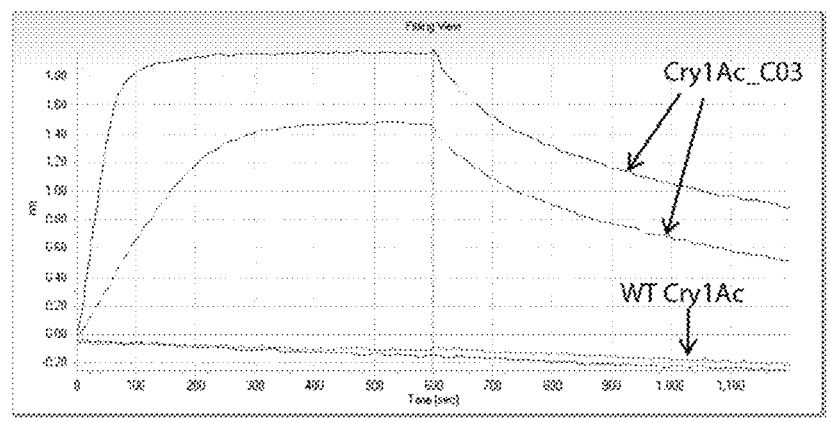
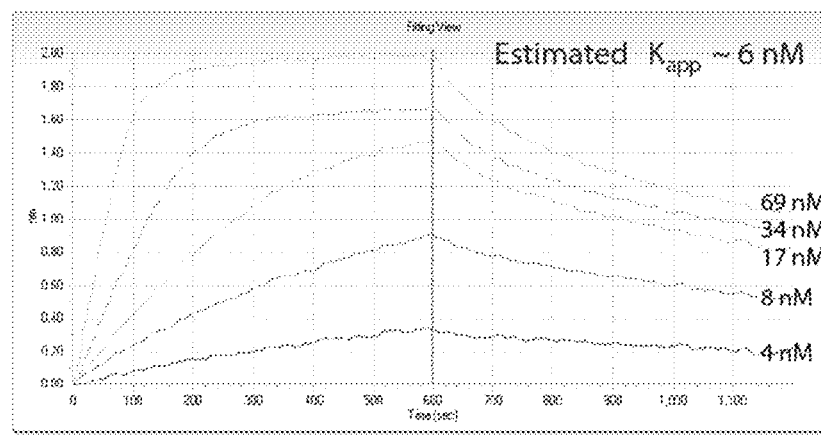
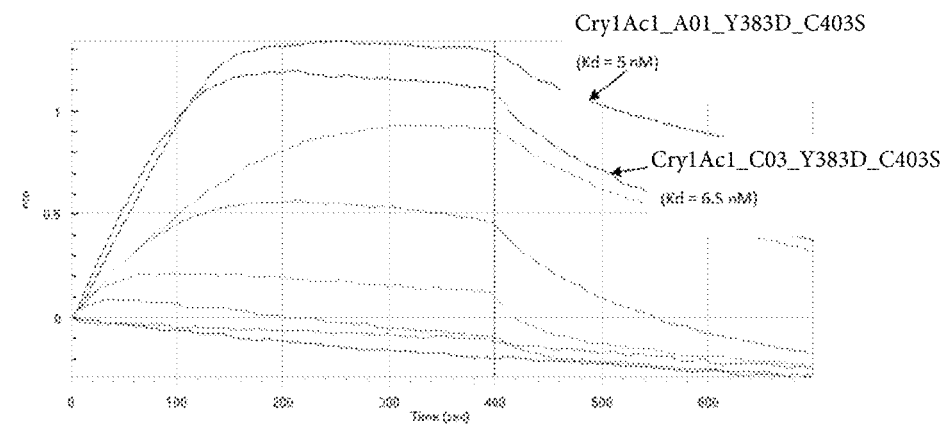

FIG. 15

| Cry1Ac variant | K_d (M) | T_m (°C) | Amino acid 14 67 163 197 285 303 321 331 343 352 360 362 383 385 403 416 460 462 533 581 |
|---|---|---|---|
| LIB50318-001-E01 (Cry1Ac C05) | 4.39E-09 | 42 | F A R G M E Q S T N A |
| Cry1Ac C03 | 5.02E-09 | 44 | A R S T N A |
| LIB50333-004-F02 | 2.54E-08 | 58 | F A R G M E Q S D T S N A |
| LIB50364-003-E11 | 6.51E-09 | 56 | A R S D T S N A |
| LIB50364-003-F11 | 5.08E-09 | 60 | F A R G E S D T S N A |
| LIB50348-001-D06 | 1.17E-08 | 48 | C F A R G M E A Q S T N A S |
| LIB50364-003-F10 | 1.40E-08 | 58 | A R S D T S N A |
| LIB50364-003-D11 | 4.28E-08 | 58 | A R M Q S D T S N A |
| LIB50364-002-F04 | 3.53E-08 | 50 | F A R G T M E A Q S T N N A S |
| Cry1Ac wt | - | 70 | C F A R G T M E A Q T S D T S N E N A S |

FIG. 16

| Target | Cry1Ac variant | K_d (M) | T_m (°C) | Amino acid 14 67 163 197 285 303 321 331 343 352 360 362 383 385 403 416 460 462 533 581 |
|---|---|---|---|---|
| TBRwt | LIB50318-001-E01 (Cry1Ac C05) | 4.39E-09 | 42 | F A R G M E Q S T N A |
| TBRwt | Cry1Ac C03 | 5.02E-09 | 44 | A R S T N A |
| TBRwt | LIB50333-004-F02 | 2.54E-08 | 58 | F A R G M E Q S D T S N A |
| TBRwt | LIB50364-003-E11 | 6.51E-09 | 56 | A R S D T S N A |
| TBRwt | LIB50364-003-F11 | 5.08E-09 | 60 | F A R G E S D T S N A |
| TBRwt | LIB50348-001-D06 | 1.17E-08 | 48 | C F A R G M E A Q S T N A S |
| TBRwt | LIB50364-003-F10 | 1.40E-08 | 56 | A R S D T S N A |
| TBRwt | LIB50364-003-D11 | 4.28E-08 | 58 | A R M Q S D T S N A |
| TBRwt | LIB50364-002-F04 | 3.53E-08 | 50 | F A R G T M E A Q S T N N A S |
| TBRwt | Cry1Ac wt | - | 70 | C F A R G T M E A Q T S D T S N E N A S |

FIG. 21
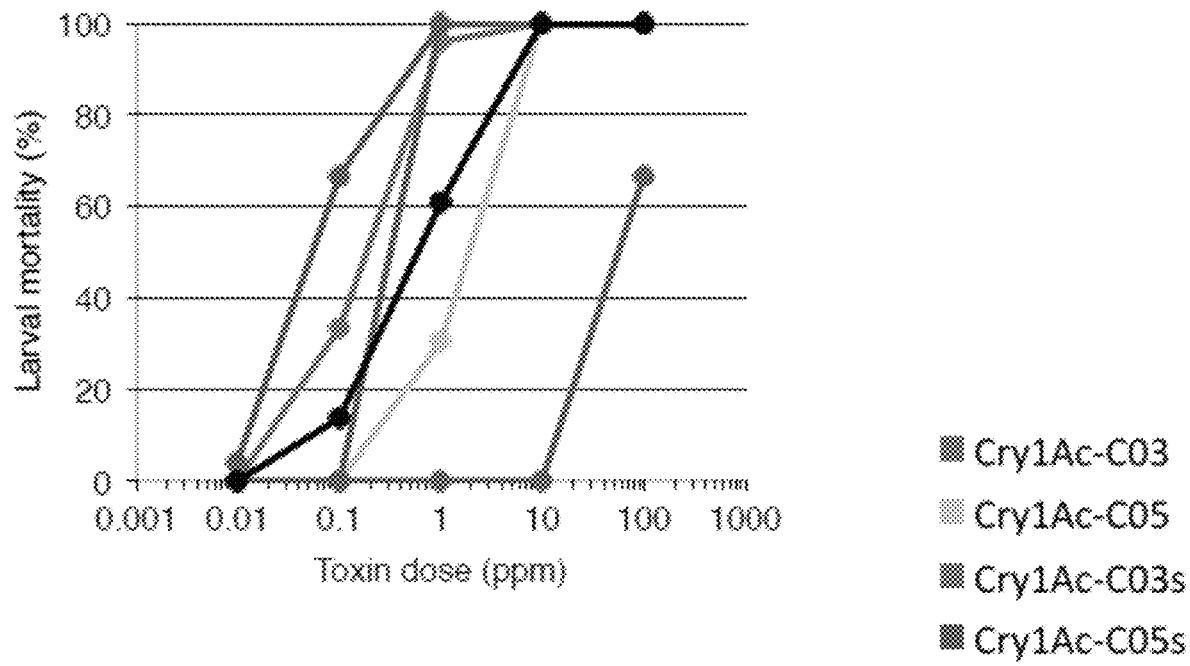
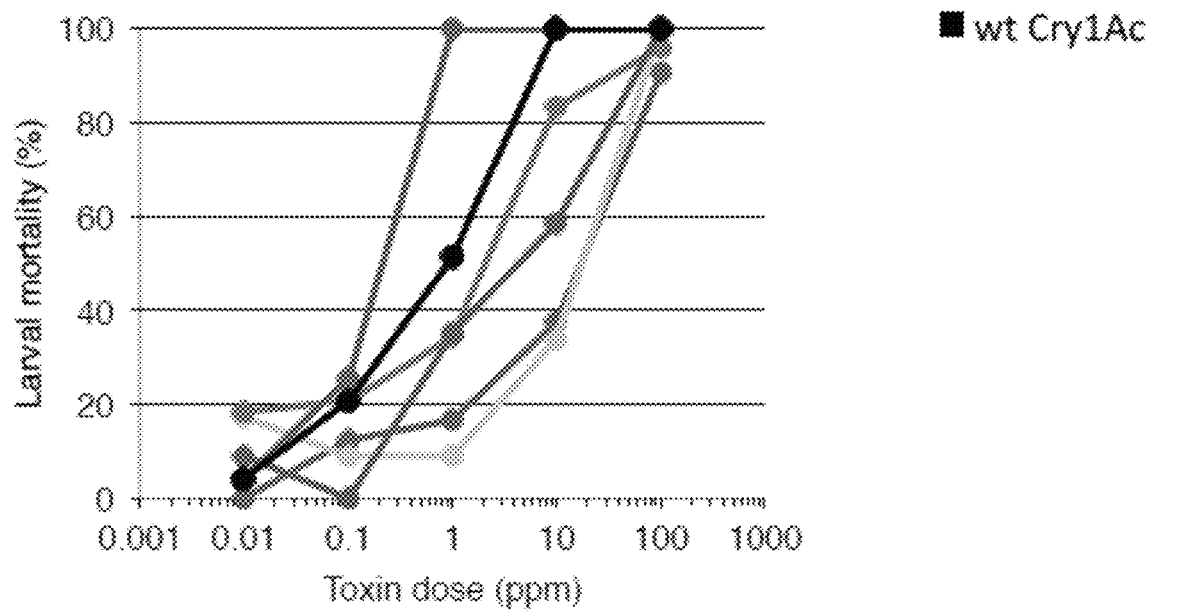

FIG. 21 cont.

*Helicoverpa zea*

*Plutella xylostella*

- Cry1Ac-C03
- Cry1Ac-C05
- Cry1Ac-C03s
- Cry1Ac-C05s
- Cry1Ac-A01s
- wt Cry1Ac

FIG. 21 cont.

*Agrotis ipsilon*

*Spodoptera frugiperda*

- Cry1Ac-C03
- Cry1Ac-C05
- Cry1Ac-C03s
- Cry1Ac-C05s
- Cry1Ac-A01s
- wt Cry1Ac

FIG. 21 cont.

*Anticarsia gemmatalis*

- Cry1Ac-C03
- Cry1Ac-C05
- Cry1Ac-C03s
- Cry1Ac-C05s
- Cry1Ac-A01s
- wt Cry1Ac

*Diatraea saccharalis*

SEQUENCE LISTING

```
<160> NUMBER OF SEQ ID NOS: 11

<210> SEQ ID NO 1
<211> LENGTH: 608
<212> TYPE: PRT
<213> ORGANISM: Bacillus thuringiensis

<400> SEQUENCE: 1
```

```
Asp Asn Asn Pro Asn Ile Asn Glu Cys Ile Pro Tyr Asn Cys Leu Ser
1               5                   10                  15

Asn Pro Glu Val Glu Val Leu Gly Gly Glu Arg Ile Glu Thr Gly Tyr
            20                  25                  30

Thr Pro Ile Asp Ile Ser Leu Ser Leu Thr Gln Phe Leu Leu Ser Glu
            35                  40                  45

Phe Val Pro Gly Ala Gly Phe Val Leu Gly Leu Val Asp Ile Ile Trp
50                  55                  60

Gly Ile Phe Gly Pro Ser Gln Trp Asp Ala Phe Leu Val Gln Ile Glu
65                  70                  75                  80

Gln Leu Ile Asn Gln Arg Ile Glu Glu Phe Ala Arg Asn Gln Ala Ile
                85                  90                  95

Ser Arg Leu Glu Gly Leu Ser Asn Leu Tyr Gln Ile Tyr Ala Glu Ser
                100                 105                 110

Phe Arg Glu Trp Glu Ala Asp Pro Thr Asn Pro Ala Leu Arg Glu Glu
            115                 120                 125

Met Arg Ile Gln Phe Asn Asp Met Asn Ser Ala Leu Thr Thr Ala Ile
            130                 135                 140

Pro Leu Phe Ala Val Gln Asn Tyr Gln Val Pro Leu Leu Ser Val Tyr
145                 150                 155                 160

Val Gln Ala Ala Asn Leu His Leu Ser Val Leu Arg Asp Val Ser Val
                165                 170                 175

Phe Gly Gln Arg Trp Gly Phe Asp Ala Ala Thr Ile Asn Ser Arg Tyr
            180                 185                 190

Asn Asp Leu Thr Arg Leu Ile Gly Asn Tyr Thr Asp Tyr Ala Val Arg
            195                 200                 205

Trp Tyr Asn Thr Gly Leu Glu Arg Val Trp Gly Pro Asp Ser Arg Asp
210                 215                 220

Trp Val Arg Tyr Asn Gln Phe Arg Arg Glu Leu Thr Leu Thr Val Leu
225                 230                 235                 240

Asp Ile Val Ala Leu Phe Pro Asn Tyr Asp Ser Arg Arg Tyr Pro Ile
            245                 250                 255

Arg Thr Val Ser Gln Leu Thr Arg Glu Ile Tyr Thr Asn Pro Val Leu
            260                 265                 270

Glu Asn Phe Asp Gly Ser Phe Arg Gly Ser Ala Gln Gly Ile Glu Arg
            275                 280                 285

Ser Ile Arg Ser Pro His Leu Met Asp Ile Leu Asn Ser Ile Thr Ile
290                 295                 300

Tyr Thr Asp Ala His Arg Gly Tyr Tyr Tyr Trp Ser Gly His Gln Ile
305                 310                 315                 320

Met Ala Ser Pro Val Gly Phe Ser Gly Pro Glu Phe Thr Phe Pro Leu
            325                 330                 335

Tyr Gly Thr Met Gly Asn Ala Ala Pro Gln Gln Arg Ile Val Ala Gln
            340                 345                 350

Leu Gly Gln Gly Val Tyr Arg Thr Leu Ser Ser Thr Leu Tyr Arg Arg
            355                 360                 365

Pro Phe Asn Ile Gly Ile Asn Asn Gln Gln Leu Ser Val Leu Asp Gly
370                 375                 380

Thr Glu Phe Ala Tyr Gly Thr Ser Ser Asn Leu Pro Ser Ala Val Tyr
385                 390                 395                 400

Arg Lys Ser Gly Thr Val Asp Ser Leu Asp Glu Ile Pro Pro Gln Asn
                405                 410                 415
```

Asn Asn Val Pro Pro Arg Gln Gly Phe Ser His Arg Leu Ser His Val
            420                 425                 430

Ser Met Phe Arg Ser Gly Phe Ser Asn Ser Ser Val Ser Ile Ile Arg
        435                 440                 445

Ala Pro Met Phe Ser Trp Ile His Arg Ser Ala Glu Phe Asn Asn Ile
450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

<210> SEQ ID NO 2
<211> LENGTH: 450
<212> TYPE: PRT
<213> ORGANISM: Trichoplusia ni

<400> SEQUENCE: 2

Ala Gly Asn Thr Phe Arg Leu Ser Arg Glu Gln Ser Thr Val Asn Gly
1               5                   10                  15

Val Leu Val Arg Val Asp Gly Gln Ser Phe Pro Arg Val Ser Ala Thr
            20                  25                  30

Asp Glu Asp Gly Leu His Ala Gly Ser Val Ser Phe Ser Val Val Gly
        35                  40                  45

Ala Ala Ala Glu Tyr Phe Ser Met Arg Asn Phe Glu Asp Asn Thr Gly
    50                  55                  60

Glu Leu Tyr Leu Ser Gln Pro Leu Pro Leu Glu Asp Asp Gly Phe Asp
65                  70                  75                  80

Ile Thr Ile Arg Gly Ser Asp Ala Gly Thr Glu Pro Gly Ser Leu Phe
                85                  90                  95

Ser Glu Val Ser Phe Arg Leu Val Phe Val Pro Thr His Gly Asp Pro
            100                 105                 110

Val Phe Ser Val Ser Gln Tyr Thr Val Ala Phe Ile Glu Lys Glu Ala
        115                 120                 125

Gly Leu Leu Glu Ser His Gln Leu Pro Arg Ala Val Asp Pro Lys Asn
130                 135                 140

Tyr Met Cys Glu Glu Met Asn Glu Pro Cys His Glu Ile Tyr Tyr Ser
145                 150                 155                 160

Ile Ile Asp Asn Asn Glu Glu Gly Tyr Phe Gln Val Asp Ser Thr Thr
                165                 170                 175

Asn Val Ile Ser Leu Ser Arg Glu Leu Glu Arg Ala Ser Gln Ala Ser
            180                 185                 190

```
His Val Val Arg Val Ala Ala Ser Asn Thr Leu Leu Asp Pro Ala Ala
            195                 200                 205

Pro Pro Pro Leu Leu Pro Ser Ser Thr Phe Leu Leu Thr Ile Asn Val
210                 215                 220

Arg Glu Ala Asp Pro Arg Pro Val Phe Glu Arg Glu Ile Tyr Thr Ala
225                 230                 235                 240

Gly Ile Tyr Glu Thr Asp Thr Ser Asn Arg Glu Leu Leu Thr Val His
            245                 250                 255

Ala Thr His Thr Glu Gly Leu Asp Ile Thr Tyr Thr Met Asp Leu Asp
            260                 265                 270

Thr Met Val Val Asp Pro Ser Leu Glu Gly Val Arg Glu Ser Ala Phe
            275                 280                 285

Thr Leu His Pro Ser Ser Gly Val Leu Ser Leu Asn Met Asn Pro Leu
            290                 295                 300

Asp Thr Met Val Gly Met Phe Glu Phe Asp Val Val Ala Thr Asp Thr
305                 310                 315                 320

Arg Gly Ala Glu Ala Arg Thr Asp Val Lys Ile Tyr Leu Ile Thr His
            325                 330                 335

Leu Asn Arg Val Tyr Phe Leu Phe Asn Asn Thr Leu Asp Val Val Asp
            340                 345                 350

Ser Asn Arg Ala Phe Ile Ala Asp Thr Phe Ser Ser Val Phe Ser Leu
            355                 360                 365

Thr Cys Asn Ile Asp Ala Val Leu Arg Ala Pro Asp Ser Ser Gly Ala
            370                 375                 380

Ala Arg Asp Asp Arg Thr Glu Val Arg Ala His Phe Ile Arg Asn His
385                 390                 395                 400

Val Pro Ala Thr Thr Asp Glu Ile Glu Gln Leu Arg Ser Asn Thr Ile
            405                 410                 415

Leu Leu Arg Ala Ile Gln Glu Thr Leu Leu Thr Arg Glu Leu His Leu
            420                 425                 430

Glu Asp Phe Val Gly Gly Ser Ser Pro Glu Leu Gly Val Asp Asn Ser
            435                 440                 445

Leu Thr
    450

<210> SEQ ID NO 3
<211> LENGTH: 712
<212> TYPE: PRT
<213> ORGANISM: Artificial Sequence
<220> FEATURE:
<223> OTHER INFORMATION: Synthetic Polypeptide

<400> SEQUENCE: 3

Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
                20                  25                  30

Gly Gly Lys Asp Pro Leu Val Pro Glu Glu Asn Asp Lys Thr Thr Val
            35                  40                  45

Ile Ala Leu Arg Glu Ile Glu Glu Gly Leu Ile Asn Asn Gln Ile Leu
        50                  55                  60

Asp Val Arg Glu Arg Gln Glu Gln Glu Gln Glu Ala Ala Glu Leu
65                  70                  75                  80

Gln Ala Val Thr Ala Ile Ala Glu Gly Arg Arg Ala Ala Ala Glu Gln
                85                  90                  95
```

```
Lys Leu Ile Ser Glu Glu Asp Leu Asp Asn Asn Pro Asn Ile Asn Glu
                100                 105                 110

Cys Ile Pro Tyr Asn Cys Leu Ser Asn Pro Glu Val Glu Val Leu Gly
            115                 120                 125

Gly Glu Arg Ile Glu Thr Gly Tyr Thr Pro Ile Asp Ile Ser Leu Ser
        130                 135                 140

Leu Thr Gln Phe Leu Leu Ser Glu Phe Val Pro Gly Ala Gly Phe Val
145                 150                 155                 160

Leu Gly Leu Val Asp Ile Ile Trp Gly Ile Phe Gly Pro Ser Gln Trp
                165                 170                 175

Asp Ala Phe Leu Val Gln Ile Glu Gln Leu Ile Asn Gln Arg Ile Glu
            180                 185                 190

Glu Phe Ala Arg Asn Gln Ala Ile Ser Arg Leu Glu Gly Leu Ser Asn
        195                 200                 205

Leu Tyr Gln Ile Tyr Ala Glu Ser Phe Arg Glu Trp Glu Ala Asp Pro
    210                 215                 220

Thr Asn Pro Ala Leu Arg Glu Glu Met Arg Ile Gln Phe Asn Asp Met
225                 230                 235                 240

Asn Ser Ala Leu Thr Thr Ala Ile Pro Leu Phe Ala Val Gln Asn Tyr
                245                 250                 255

Gln Val Pro Leu Leu Ser Val Tyr Val Gln Ala Ala Asn Leu His Leu
            260                 265                 270

Ser Val Leu Arg Asp Val Ser Val Phe Gly Gln Arg Trp Gly Phe Asp
        275                 280                 285

Ala Ala Thr Ile Asn Ser Arg Tyr Asn Asp Leu Thr Arg Leu Ile Gly
    290                 295                 300

Asn Tyr Thr Asp Tyr Ala Val Arg Trp Tyr Asn Thr Gly Leu Glu Arg
305                 310                 315                 320

Val Trp Gly Pro Asp Ser Arg Asp Trp Val Arg Tyr Asn Gln Phe Arg
                325                 330                 335

Arg Glu Leu Thr Leu Thr Val Leu Asp Ile Val Ala Leu Phe Pro Asn
            340                 345                 350

Tyr Asp Ser Arg Arg Tyr Pro Ile Arg Thr Val Ser Gln Leu Thr Arg
        355                 360                 365

Glu Ile Tyr Thr Asn Pro Val Leu Glu Asn Phe Asp Gly Ser Phe Arg
    370                 375                 380

Gly Ser Ala Gln Gly Ile Glu Arg Ser Ile Arg Ser Pro His Leu Met
385                 390                 395                 400

Asp Ile Leu Asn Ser Ile Thr Ile Tyr Thr Asp Ala His Arg Gly Tyr
                405                 410                 415

Tyr Tyr Trp Ser Gly His Gln Ile Met Ala Ser Pro Val Gly Phe Ser
            420                 425                 430

Gly Pro Glu Phe Thr Phe Pro Leu Tyr Gly Thr Met Gly Asn Ala Ala
        435                 440                 445

Pro Gln Gln Arg Ile Val Ala Gln Leu Gly Gln Gly Val Tyr Arg Thr
    450                 455                 460

Leu Ser Ser Thr Leu Tyr Arg Arg Pro Phe Asn Ile Gly Ile Asn Asn
465                 470                 475                 480

Gln Gln Leu Ser Val Leu Asp Gly Thr Glu Phe Ala Tyr Gly Thr Ser
                485                 490                 495

Ser Asn Leu Pro Ser Ala Val Tyr Arg Lys Ser Gly Thr Val Asp Ser
            500                 505                 510
```

| | | | | | | | | | | | |
|---|---|---|---|---|---|---|---|---|---|---|---|
|Leu|Asp|Glu|Ile|Pro|Pro|Gln|Asn|Asn|Val|Pro|Pro|Arg|Gln|Gly|
| | |515| | | |520| | | |525| | | | |

Phe Ser His Arg Leu Ser His Val Ser Met Phe Arg Ser Gly Phe Ser
            530                 535                 540

Asn Ser Ser Val Ser Ile Ile Arg Ala Pro Met Phe Ser Trp Ile His
545                 550                 555                 560

Arg Ser Ala Glu Phe Asn Asn Ile Ile Ala Ser Asp Ser Ile Thr Gln
            565                 570                 575

Ile Pro Ala Val Lys Gly Asn Phe Leu Phe Asn Gly Ser Val Ile Ser
            580                 585                 590

Gly Pro Gly Phe Thr Gly Gly Asp Leu Val Arg Leu Asn Ser Ser Gly
            595                 600                 605

Asn Asn Ile Gln Asn Arg Gly Tyr Ile Glu Val Pro Ile His Phe Pro
610                 615                 620

Ser Thr Ser Thr Arg Tyr Arg Val Arg Val Arg Tyr Ala Ser Val Thr
625                 630                 635                 640

Pro Ile His Leu Asn Val Asn Trp Gly Asn Ser Ser Ile Phe Ser Asn
            645                 650                 655

Thr Val Pro Ala Thr Ala Thr Ser Leu Asp Asn Leu Gln Ser Ser Asp
            660                 665                 670

Phe Gly Tyr Phe Glu Ser Ala Asn Ala Phe Thr Ser Ser Leu Gly Asn
            675                 680                 685

Ile Val Gly Val Arg Asn Phe Ser Gly Thr Ala Gly Val Ile Ile Asp
            690                 695                 700

Arg Phe Glu Phe Ile Pro Val Thr
705                 710

<210> SEQ ID NO 4
<211> LENGTH: 2139
<212> TYPE: DNA
<213> ORGANISM: Artificial Sequence
<220> FEATURE:
<223> OTHER INFORMATION: Synthetic Polynucleotide

<400> SEQUENCE: 4

```
atggcacgcg taactgttca ggacgctgta gagaaaattg gtaaccgttt tgacctggta      60
ctggtcgccg cgcgtcgcgc tcgtcagatg caggtaggcg aaaggatcc gctggtaccg      120
gaagaaaacg ataaaaccac tgtaatcgcg ctgcgcgaaa tcgaagaagg tctgatcaac     180
aaccagatcc tcgacgttcg cgaacgccag gaacagcaag agcaggaagc cgctgaatta     240
caagccgtta ccgctattgc tgaaggtcgt cgtgcggccg cggaacaaaa gcttatttct     300
gaagaggact tggataacaa tccgaacatc aatgaatgca ttccttataa ttgtttaagt     360
aaccctgaag tagaagtatt aggtggagaa agaatagaaa ctggttacac cccaatcgat     420
atttccttgt cgctaacgca atttcttttg agtgaatttg ttcccggtgc tggatttgtg     480
ttaggactag ttgatataat atggggaatt tttggtccct ctcaatggga cgcatttctt     540
gtacaaattg aacagttaat taaccaaaga atagaagaat cgctaggaa ccaagccatt     600
tctagattag aaggactaag caatctttat caaatttacg cagaatcttt tagagagtgg     660
gaagcagatc ctactaatcc agcattaaga gaagagatgc gtattcaatt caatgacatg     720
aacagtgccc ttacaaccgc tattcctctt tttgcagttc aaaattatca agttcctctt     780
ttatcagtat atgttcaagc tgcaaattta catttatcag ttttgagaga tgtttcagtg     840
tttggacaaa ggtggggatt tgatgccgcg actatcaata gtcgttataa tgatttaact     900
```

```
aggcttattg gcaactatac agattatgct gtacgctggt acaatacggg attagaacgt    960
gtatggggac cggattctag agattgggta aggtataatc aatttagaag agaattaaca   1020
ctaactgtat tagatatcgt tgctctgttc ccgaattatg atagtagaag atatccaatt   1080
cgaacagttt cccaattaac aagagaaatt tatacaaacc cagtattaga aaattttgat   1140
ggtagttttc gaggctcggc tcagggcata gaaagaagta ttaggagtcc acatttgatg   1200
gatatactta acagtataac catctatacg gatgctcata ggggttatta ttattggtca   1260
gggcatcaaa taatggcttc tcctgtaggg ttttcggggc cagaattcac ttttccgcta   1320
tatgaaacta tgggaaatgc agctccacaa caacgtattg ttgctcaact aggtcagggc   1380
gtgtatagaa cattatcgtc cactttatat agaagacctt ttaatatagg gataaataat   1440
caacaactat ctgttcttga cgggacagaa tttgcttatg gaacctcctc aaatttgcca   1500
tccgctgtat acagaaaaag cggaacggta gattcgctgg atgaaatacc gccacagaat   1560
aacaacgtgc cacctaggca aggatttagt catcgattaa gccatgtttc aatgtttcgt   1620
tcaggcttta gtaatagtag tgtaagtata ataagagctc ctatgttctc ttggatacat   1680
cgtagtgctg aatttaataa tataattgca tcggatagta ttactcaaat ccctgcagtg   1740
aagggaaact ttctttttaa tggttctgta atttcaggac caggatttac tggtggggac   1800
ttagttagat taaatagtag tggaaataac attcagaata gagggtatat tgaagttcca   1860
attcacttcc catcgacatc taccagatat cgagttcgtg tacggtatgc ttctgtaacc   1920
ccgattcacc tcaacgttaa ttggggtaat tcatccattt tttccaatac agtaccagct   1980
acagctacgt cattagataa tctacaatca agtgattttg ttatttttga aagtgccaat   2040
gcttttacat cttcattagg taatatagta ggtgttagaa attttagtgg gactgcagga   2100
gtgataatag acagatttga atttattcca gttacttaa                          2139
```

<210> SEQ ID NO 5
<211> LENGTH: 221
<212> TYPE: PRT
<213> ORGANISM: Trichoplusia ni

<400> SEQUENCE: 5

Arg Pro Val Phe Glu Arg Glu Ile Tyr Thr Ala Gly Ile Tyr Glu Thr
1               5                   10                  15

Asp Thr Ser Asn Arg Glu Leu Leu Thr Val His Ala Thr His Thr Glu
            20                  25                  30

Gly Leu Asp Ile Thr Tyr Thr Met Asp Leu Asp Thr Met Val Val Asp
        35                  40                  45

Pro Ser Leu Glu Gly Val Arg Glu Ser Ala Phe Thr Leu His Pro Ser
    50                  55                  60

Ser Gly Val Leu Ser Leu Asn Met Asn Pro Leu Asp Thr Met Val Gly
65                  70                  75                  80

Met Phe Glu Phe Asp Val Val Ala Thr Asp Thr Arg Gly Ala Glu Ala
                85                  90                  95

Arg Thr Asp Val Lys Ile Tyr Leu Ile Thr His Leu Asn Arg Val Tyr
            100                 105                 110

Phe Leu Phe Asn Asn Thr Leu Asp Val Val Asp Ser Asn Arg Ala Phe
        115                 120                 125

Ile Ala Asp Thr Phe Ser Ser Val Phe Ser Leu Thr Cys Asn Ile Asp
    130                 135                 140

Ala Val Leu Arg Ala Pro Asp Ser Ser Gly Ala Ala Arg Asp Asp Arg
145                 150                 155                 160

```
Thr Glu Val Arg Ala His Phe Ile Arg Asn His Val Pro Ala Thr Thr
                165                 170                 175

Asp Glu Ile Glu Gln Leu Arg Ser Asn Thr Ile Leu Leu Arg Ala Ile
            180                 185                 190

Gln Glu Thr Leu Leu Thr Arg Glu Leu His Leu Glu Asp Phe Val Gly
        195                 200                 205

Gly Ser Ser Pro Glu Leu Gly Val Asp Asn Ser Leu Thr
    210                 215                 220
```

```
<210> SEQ ID NO 6
<211> LENGTH: 221
<212> TYPE: PRT
<213> ORGANISM: Trichoplusia ni

<400> SEQUENCE: 6

Arg Pro Val Phe Glu Arg Glu Ile Tyr Thr Ala Gly Ile Tyr Glu Thr
1               5                   10                  15

Asp Thr Ser Asn Arg Glu Leu Leu Thr Val His Ala Thr His Thr Glu
            20                  25                  30

Gly Leu Asp Ile Thr Tyr Thr Met Asp Leu Asp Thr Met Val Val Asp
        35                  40                  45

Pro Ser Leu Glu Gly Val Arg Glu Ser Ala Phe Thr Leu His Pro Ser
    50                  55                  60

Ser Gly Val Leu Ser Leu Asn Phe Asn Pro Ser Ala Thr Met Val Gly
65                  70                  75                  80

Met Phe Glu Phe Asp Val Val Ala Thr Asp Thr Arg Gly Ala Glu Ala
                85                  90                  95

Arg Thr Asp Val Lys Ile Tyr Leu Ile Thr His Leu Asn Arg Val Tyr
            100                 105                 110

Phe Leu Phe Asn Asn Thr Leu Asp Val Val Asp Ser Asn Arg Ala Phe
        115                 120                 125

Ile Ala Asp Thr Phe Ser Ser Val Phe Ser Leu Thr Cys Asn Ile Asp
    130                 135                 140

Ala Val Leu Arg Ala Pro Asp Ser Ser Gly Ala Ala Arg Asp Asp Arg
145                 150                 155                 160

Thr Glu Val Arg Ala His Phe Ile Arg Asn His Val Pro Ala Thr Thr
                165                 170                 175

Asp Glu Ile Glu Gln Leu Arg Ser Asn Thr Ile Leu Leu Arg Ala Ile
            180                 185                 190

Gln Glu Thr Leu Leu Thr Arg Glu Leu His Leu Glu Asp Phe Val Gly
        195                 200                 205

Gly Ser Ser Pro Glu Leu Gly Val Asp Asn Ser Leu Thr
    210                 215                 220
```

```
<210> SEQ ID NO 7
<211> LENGTH: 20
<212> TYPE: PRT
<213> ORGANISM: Heliothis virescens

<400> SEQUENCE: 7

Thr Gly Val Leu Thr Leu Asn Phe Gln Pro Thr Ala Ser Met His Gly
1               5                   10                  15

Met Phe Glu Phe
            20
```

```
<210> SEQ ID NO 8
```

```
<211> LENGTH: 20
<212> TYPE: PRT
<213> ORGANISM: Helicoverpa armigera

<400> SEQUENCE: 8

Thr Gly Val Leu Ser Leu Asn Phe Gln Pro Thr Ala Ala Met His Gly
1               5                   10                  15
Met Phe Glu Phe
            20

<210> SEQ ID NO 9
<211> LENGTH: 20
<212> TYPE: PRT
<213> ORGANISM: Pectinophora gossypiella

<400> SEQUENCE: 9

Thr Gly Val Leu Ile Leu Arg Ile Gln Pro Thr Ala Ser Met Gln Gly
1               5                   10                  15
Met Phe Glu Phe
            20

<210> SEQ ID NO 10
<211> LENGTH: 20
<212> TYPE: PRT
<213> ORGANISM: Trichoplusia ni

<400> SEQUENCE: 10

Ser Gly Val Leu Ser Leu Asn Met Asn Pro Leu Asp Thr Met Val Gly
1               5                   10                  15
Met Phe Glu Phe
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 11

Ser Gly Val Leu Ser Leu Asn Phe Asn Pro Ser Ala Thr Met Val Gly
1               5                   10                  15
Met Phe Glu Phe
            20
```

EVOLUTION OF *BT* TOXINS

RELATED APPLICATIONS

This application claims priority to U.S. provisional applications, U.S. Ser. No. 62/196,253, filed Jul. 23, 2015, entitled "EVOLUTION OF BT TOXINS," and U.S. Ser. No. 62/305,497, filed Mar. 8, 2016, entitled "EVOLUTION OF BT TOXINS," each application which is incorporated herein by reference.

GOVERNMENT SUPPORT

This invention was made with government support under grant numbers HR0011-11-2-0003 and N66001-12-C-4207 awarded by the Defense Advanced Research Projects Agency (DARPA). The government has certain rights in the invention.

BACKGROUND OF THE INVENTION

*Bacillus thuringiensis* (Bt) is a gram-positive bacterium that produces crystalline inclusion bodies (Bt toxins) during sporulation, which exhibit potent insecticidal activity through disruption of the osmotic balance in the insect midgut as a consequence of membrane insertion and pore formation (FIG. 1). A limited number of Bt toxins have become widespread biological alternatives to chemical insecticides. Bt toxins can be delivered to insect pests via conventional application routes, and can also be produced in the plant at all times during the plant life cycle to protect the plant from infestation. Bt toxins are benign to other arthropods within the crop field as well as to humans, and are environmentally friendly. However, the development of resistance to this limited set of Bt toxins in some targeted pests represents a serious threat to the viability of these and related Bt toxins for use in pest control applications. Thus there is a need for the development of pesticidal toxin molecules that can be produced in or applied to plants and seeds, that can control targeted pests that have developed resistance to one or more toxin proteins.

SUMMARY OF THE INVENTION

The Bt toxin Cry1Ac has been widely used in plants for the past two decades to control certain lepidopteran species of insect pests. Some target pests have developed resistance to this and to related Bt toxins, and resistant populations of pests have become a problematic phenomenon. Thus, there is a need for the development of novel Bt toxins that are effective against pests that have developed resistance to currently available Bt toxins.

Some aspects of the present disclosure are based on the recognition that methods of phage-assisted continuous evolution (PACE) are useful for generating variant polypeptides based on Bt toxins that exhibit altered Bt toxin receptor binding capabilities. Such variant polypeptides comprising altered amino acid sequences as compared to wild-type Bt toxins, referred to herein as variant Bt toxins or Bt toxin variants, hold the potential to exhibit efficacy against a variety of target pests. Some aspects of this disclosure provide variant Bt toxins that bind with higher affinity to a receptor in a Bt toxin-resistant pest than the wild-type Bt toxin.

The general concept of PACE technology been described, for example in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. Application, U.S. Ser. No. 13/922,812, filed Jun. 20, 2013, the entire contents of each of which are incorporated herein by reference.

Some aspects of this disclosure relate to variant Bt toxins and methods for producing the same. In some aspects, the disclosure provides a protein comprising an amino acid sequence that is at least 70%, at least 80%, at least 90%, at least 95%, at least 96%, at least 97%, at least 98%, or at least 99% identical to SEQ ID NO: 1 (protein encoded by *B. thuringiensis* Cry1Ac; GenBank Accession No. AY730621, residues 2-609), wherein the protein comprises at least one amino acid variation (also referred to sometimes as "mutation") in the amino acid sequence provided in Table 1. In some embodiments, the amino acid sequence is at least 75%, at least 85%, at least 95%, at least 96%, at least 97%, at least 98%, at least 99%, at least 99.5%, at least 99.6%, at least 99.7%, at least 99.8%, or at least 99.9% identical to SEQ ID NO: 1. In some embodiments, the amino acid sequence is about 95-99.9% identical to SEQ ID NO: 1. In some embodiments, the protein comprises at least 2, at least 3, at least 4, at least 5, at least 6, at least 7, at least 8, at least 9, at least 10, at least 11, at least 12, at least 13, at least 14, or at least 15 different amino acid sequence variations provided in Table 1 as compared to the sequence of amino acids set forth in SEQ ID NO:1. In some embodiments, the at least one variation in sequence is located in a portion of the receptor binding domain of the protein (e.g., in a sequence corresponding to amino acid residues 275-462 of SEQ ID NO: 1). In some embodiments, there is at least one variation in amino acid sequence of the protein that is selected from the group consisting of: C14W, C14R, F67S, R197G, A267T, T303N, M321K, E331G, A343E, Q352H, T360I, S362P, N416D, E460K, N462S, D383Y, 5403C, and S581L. In some embodiments, the protein does not comprise a destabilizing mutation/variation in the amino acid sequence of the protein, e.g., a mutation that increases the proteins' sensitivity to tryptic digest or to thermal variation, as compared to the wild-type Bt toxin (e.g., to a Bt toxin having the amino acid sequence of SEQ ID NO: 1). In some embodiments, the protein does not comprise a variation in protein sequence at the residue corresponding to residue D383 of SEQ ID NO: 1 and/or at the residue corresponding to residue 5403 of SEQ ID NO: 1. In some embodiments, the protein comprises the wild-type amino acid at the residue corresponding to D383 of SEQ ID NO: 1 and/or at the residue corresponding to residue 5403 of SEQ ID NO: 1. In some embodiments, the protein comprises the mutations E460K, N462S, T303N, A343E, T360I, S581L, C14W, M321K, and Q352H. In some embodiments, the protein comprises the mutations E460K, N462S, T303N, A343E, T360I, S581L, C14W, M321K, Q352H, F67S, G285D, and E331G. In some embodiments, the protein comprises the mutations E460K, N462S, T303N, A343E, T360I, S581L, C14W, M321K, Q352H, F67S, G285D, and E331G.

In some aspects, the disclosure provides a protein comprising a receptor binding domain, wherein the receptor binding domain comprises an amino acid sequence that is at least 70%, at least 80%, at least 85%, at least 90%, at least about 94%, at least 95%, at least 96%, at least 97%, at least 98%, at least 99%, or at least 99.4% identical to amino acid residues 275-462 of SEQ ID NO: 1, wherein the receptor binding domain comprises at least one variation in protein sequence provided in Table 1, and wherein the protein binds a Bt toxin receptor with higher affinity than SEQ ID NO: 1. In some embodiments, the receptor binding domain comprises an amino acid sequence that is at least 70%, at least 80%, at least 85%, at least 90%, at least 92%, at least 93%, at least 94%, at least 95%, at least 96%, at least 97%, at least 98%, at least 99%, or at least 99.9% identical to the receptor binding domain as set forth in SEQ ID NO: 1 from amino acid residues 275-462. In some embodiments, the receptor binding domain comprises an amino acid sequence having at least 2, at least 3, at least 4, at least 5, at least 6, at least 7, at least 8, at least 9, at least 10, at least 11, at least 12, at least 13, at least 14, or at least 15 mutations provided in Table 1. In some embodiments, the at least one variation in in amino acid sequence of the protein is selected from the group consisting of: T303N, M321K, E331G, A343E, Q352H, T360I, S362P, N416D, E460K, and N462S. In some embodiments, the protein does not comprise a destabilizing variation in amino acid sequence of the protein, e.g., a mutation that reduces the stability of the protein against tryptic digest or increases or decreases thermal stability as compared to the wild-type Bt toxin (e.g., to a Bt toxin having the amino acid sequence of SEQ ID NO: 1). In some embodiments, the protein does not comprise a mutation at the residue corresponding to residue D383 of SEQ ID NO: 1 and/or at the residue corresponding to residue S403 of SEQ ID NO: 1. In some embodiments, the protein comprises the wild-type amino acid at the residue corresponding to D383 of SEQ ID NO: 1 and/or at the residue corresponding to residue 5403 of SEQ ID NO: 1. In some embodiments, the protein comprises the variation in amino acid sequence E460K, N462S, T303N, A343E, T360I, M321K, and Q352H. In some embodiments, the protein comprises the variation in amino acid sequence E460K, N462S, T303N, A343E, T360I, M321K, Q352H, G285D, and E331G. In some embodiments, the protein binds to a Bt toxin receptor comprising an amino acid sequence represented by SEQ ID NO: 2 (*Trichoplusia ni* cadherin, GenBank Accession No. AEA29692, residues 1133-1582).

In some embodiments, the protein is effective in killing insects that are resistant to treatment with Bt toxin, e.g., resistant to treatment with a protein represented by SEQ ID NO: 1. In some embodiments, the insects are selected from the group consisting of the orders Lepidoptera, Coleoptera, Diptera, and Hemiptera.

In some aspects, the disclosure provides a genetically engineered cell expressing a variant Bt toxin from a recombinant nucleotide sequence operably linked to a promoter functional in said cell. The nucleotide sequence encodes the protein as described herein. In some embodiments, the cell is a bacterial cell. In some embodiments, the bacterial cell is an *E. coli* cell. In some embodiments, the cell is a plant cell. In some embodiments, the plant cell is a monocot plant cell or a dicot plant cell. For example, dicot plant cells and dicot plants derived therefrom may include but are not limited to tomato, cotton, sugar beet, potato, soybean, tobacco, canola, and alfalfa. Monocot plant cells and monocot plants derived therefrom may include but are not limited to corn, sugarcane, wheat, and rice.

In some aspects, the disclosure provides a genetically modified plant, wherein the plant comprises or consists of recombinant plant cells expressing a pesticidal toxin as provided herein. In some embodiments, the plant is a monocot plant or a dicot plant as noted above. In some embodiments, the plant is resistant to pest infestation by one or more pests that previously were not inhibited by pesticidal proteins or by Bt toxins.

In some aspects, the disclosure provides a method for producing an evolved pesticidal toxin protein, the method comprising: (a) contacting a population of bacterial host cells with a population of M13 phages comprising a first gene encoding a first fusion protein, and deficient in a full-length pIII gene, wherein (1) the first fusion protein comprises a pesticidal toxin protein binding region (TBR) and a repressor element, (2) the phage allows for expression of the first fusion protein in the host cells, (3) the host cells are suitable host cells for M13 phage infection, replication, and packaging; and (4) the host cells comprise an expression construct comprising a second gene encoding the full length pIII protein and a third gene encoding a second fusion protein comprising a pesticidal toxin and an RNA polymerase, wherein expression of the gene encoding the full length pIII is dependent on interaction of the RNA polymerase of the second fusion protein with the TBR of the first fusion protein; (b) incubating the population of host cells under conditions allowing for mutations (and thus, amino acid substitutions) to be introduced into the third gene, the production of infectious M13 phage, and the infection of host cells with M13 phage, wherein infected cells are removed from the population of host cells, and wherein the population of host cells is replenished with fresh host cells that are not infected by M13 phage; and, (c) isolating a mutated M13 phage replication product encoding an evolved second fusion protein from the population of host cells. In some embodiments, the host cells further comprise a mutagenesis plasmid. In some embodiments, the mutagenesis plasmid is an MP4 or MP6 plasmid. In some embodiments, the pesticidal toxin is Cry1Ac (SEQ ID NO: 1), or a fragment thereof. In some embodiments, the fragment of Cry1Ac comprises the receptor binding domain. In some embodiments, the RNA polymerase is RpoZ or RpoA. In some embodiments, the expression construct encoding the full length pIII protein further comprises a promoter. In some embodiments, the promoter is a lacZ promoter or a mutant lacZ promoter. In some embodiments, the expression construct encoding the full length pIII protein further comprises a repressor binding site. In some embodiments, the repressor binding site is a lambda phage (λ) cI, 434 cI, or Zif268 binding site. In some aspects, the disclosure relates to a method of pest control, the method comprising, providing to a pest a pesticidal toxin variant as described by the disclosure. In some embodiments, the pest is selected from the group consisting of the Orders Lepidoptera, Coleoptera, Diptera, and Hemiptera. In some embodiments, the pest is resistant to treatment with the pesticidal toxin, wherein the pesticidal toxin is represented by SEQ ID NO: 1.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 2 shows a schematic illustration of cadherin-like receptors from *T. ni* and other insect species (*B. mori*, H. amigera, H. viscerens, *M. sexta*). Partial amino acid sequences for each cadherin-like receptor are depicted, along with the consensus TBR3 amino acid sequence. The sequences from top to bottom correspond to SEQ ID NOs: 7-11.

FIG. 5 describes Round 2 of PACE selection of Cry1Ac variants. The intermediate stringency/moderate mutagenesis B2H system is graphically depicted. Mutagenesis plasmid M4 is shown as a vector map. Data on the histogram represent 264 hours of PACE.

FIG. 8A illustrates phage titer, lagoon flow rate, and average mutations per clone in the four-round PACE evolution assay. FIG. 8B illustrates examples of mutations identified in the four-round PACE evolution assay.

FIG. 9 illustrates mutations observed during the four-round PACE evolution assay.

FIG. 10 shows protein SDS gel electrophoresis of trypsin treated protein samples corresponding to Cry1Ac1 and variants thereof (upper panel). The arrow indicates the band of the toxic core. EV: Empty vector control; DM: Double mutant Cry1Ac1_D383Y_S403C. Center panel shows the amino acid substitutions of the PACE variants tested in the upper panel. Amino acid numbering corresponds to SEQ ID NO: 1. Bottom panel shows protein SDS gel electrophoresis of trypsin treated protein samples corresponding to selected stabilized variants. The arrow indicates the band of the toxic core.

FIG. 11 shows PACE-evolved Cry1Ac variant activity in Sf9 cells. PACE-evolved Cry1Ac variants are active against T. ni cadherin-like receptor CAD3 expressed in SF9 cells. Wild-type Cry1Ac is inactive.

FIG. 12 shows PACE-evolved Cry1Ac variant activity in T. ni larvae. PACE-evolved Cry1Ac variants are active against soybean looper in a diet bioassay but efficacy is lower than wild-type Cry1Ac.

FIG. 14 shows PACE-evolved Cry1Ac variant binding affinity for T. ni cadherin-like receptor. PACE-evolved Cry1Ac variant binds to the receptor with high affinity; wild-type Cry1Ac does not bind to the receptor. The lower panel shows in vitro binding of purified stabilized consensus PACE-evolved Cry1Ac1 variants to toxin-binding domain TBR3 from the T. ni cadherin, immobilized on a ForteBio chip via His-tag.

FIG. 15 shows screening of Cry1Ac1 variants (solubilized and trypsinized Bt spore/crystal mixtures) for toxicity to Sf9 cells expressing T. ni cadherin expressed as relative fluorescence caused by influx of SytoxGreen fluorescent dye into cells as result of toxin-induced membrane disruption.

FIG. 16 shows toxicity of purified Cry1Ac1 consensus Cry1Ac1 PACE-evolved variant Cry1Ac1_C03 and stabilized consensus Cry1Ac1 PACE-evolved variants (at 10 µg/ml), to Sf9 cells expressing C. includens cadherin.

FIG. 17 shows the activity of stabilized Cry1Ac1 variants (Bt spore/crystal mixtures) against soybean looper (C. includens). Numbers above bars are stunting scores. Letters below bars are for mortality T-grouping for mortality.

FIG. 18 shows the activity (mortality) of stabilized consensus PACE-evolved Cry1Ac1 variants (Bt spore/crystal mixtures) in diet bioassay against T. ni. Numbers above bars are stunting scores (maximum stunting score—3). Letters below bars are for mortality T-grouping.

FIG. 19 shows data from a larval growth inhibition assay in Bt toxin susceptible and Bt toxin resistant T. ni. The larvae were exposed to wild-type Cry1Ac (control) and to various evolved Bt toxins. The data demonstrate that exemplary stabilized evolved Bt toxins are efficient against both T. ni larvae that are susceptible to wild-type Bt toxin and T. ni larvae that are resistant to wild-type Bt Toxin.

Figure 20B:
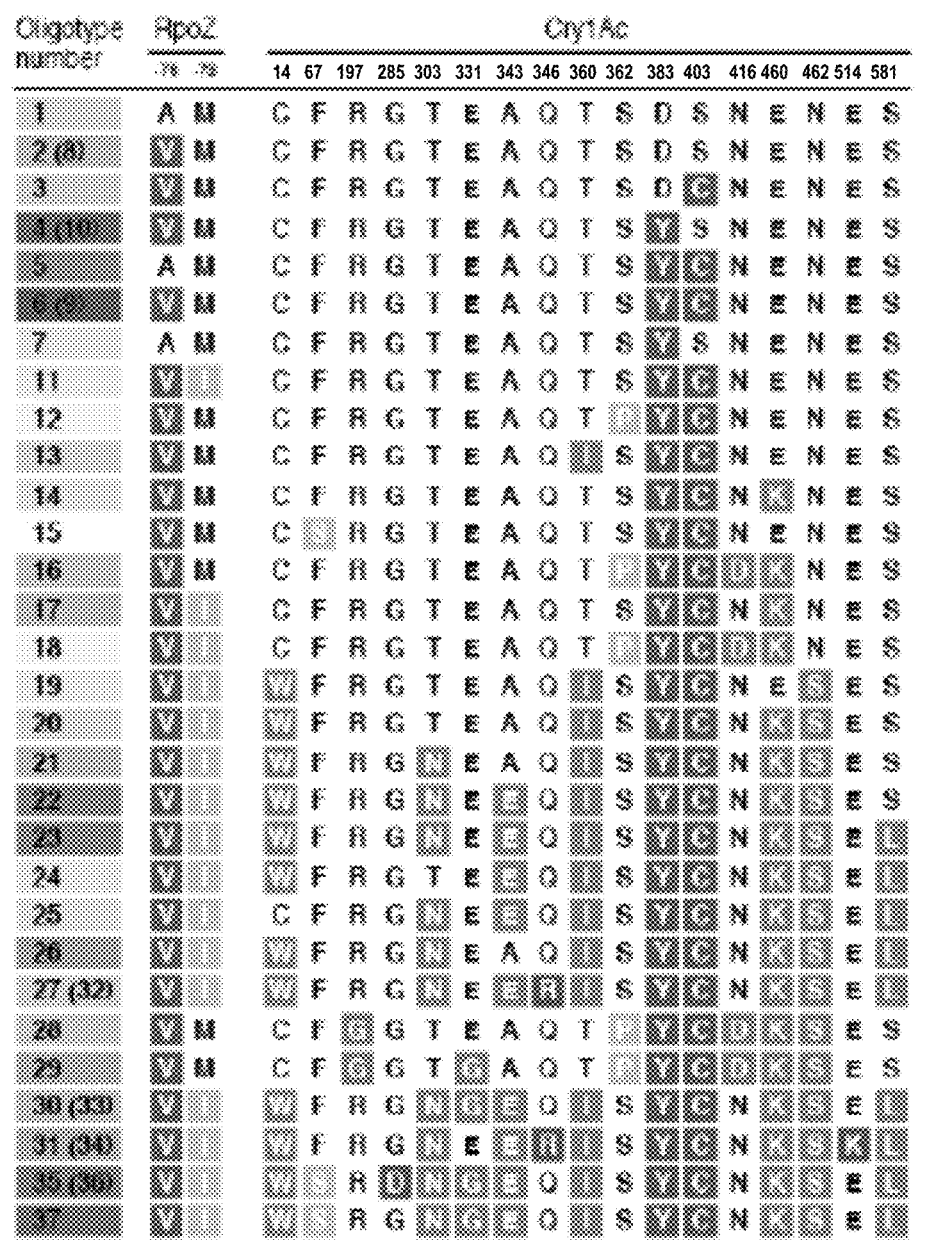

FIGS. 20A-20C show oligotyping analysis of lagoon samples during PACE based on high-throughput DNA sequencing data. FIG. 20A shows olgiotypes containing mutations that occur at high frequency (≥1%) which are represented by different polygons in the graph, shaded based on the stage in which they first became abundant in the evolving Cry1Ac gene pool. FIG. 20B shows the genotype of each oligotype in the table. The numbers in parentheses indicate the oligotype number assigned to that mutant following a synonymous (silent) mutation. FIG. 20C illustrates plausible evolution trajectories over the entire PACE experiment derived from oligotyping analysis which indicates instances of recombination during PACE, and also reveals the influence of mutation rate, selection stringency, and target protein on evolutionary outcomes.

FIG. 21 shows insect diet bioassay activity of PACE-evolved Cry1Ac variants against various agricultural pests. Two consensus and three stabilized PACE-evolved Cry1Ac variants were tested for activity in eleven pests: *Chrysodeixis* includes (soybean looper); *Heliothis virescens* (tobacco budworm); *Helicoverpa zea* (corn earworm); *Plutella xylostella* (diamondback moth); *Agrotis ipsilon* (black cutworm); *Spodoptera frugiperda* (fall armyworm); *Anticarsia gemmatalis* (velvetbean caterpillar); *Diatraea saccharalis* (sugarcane borer); *Spodoptera eridania* (southern armyworm); *Leptinotarsa decemlineata* (Colorado potato beetle); and *Lygus lineolaris* (tarnished plant bug). Stabilized variants showed enhanced activity in *C. includens* and *H. virescens* as compared to wild-type Cry1Ac, and comparable activity to wild-type Cry1Ac in *H. zea, P. xylostella, A. ipsilon, S. frugiperda, A. gemmatalis*, and D. saccharalis. No activity was observed for any of the Cry1Ac variants at any tested dose for *S. eridania, L. decemlineata* or *L. lineolaris*. No insect larvae mortality was observed for *S. frugiperda*, although high toxin doses greatly stunted growth.

DEFINITIONS

*Bacillus thuringiensis* (Bt) Toxins

Figure 1:
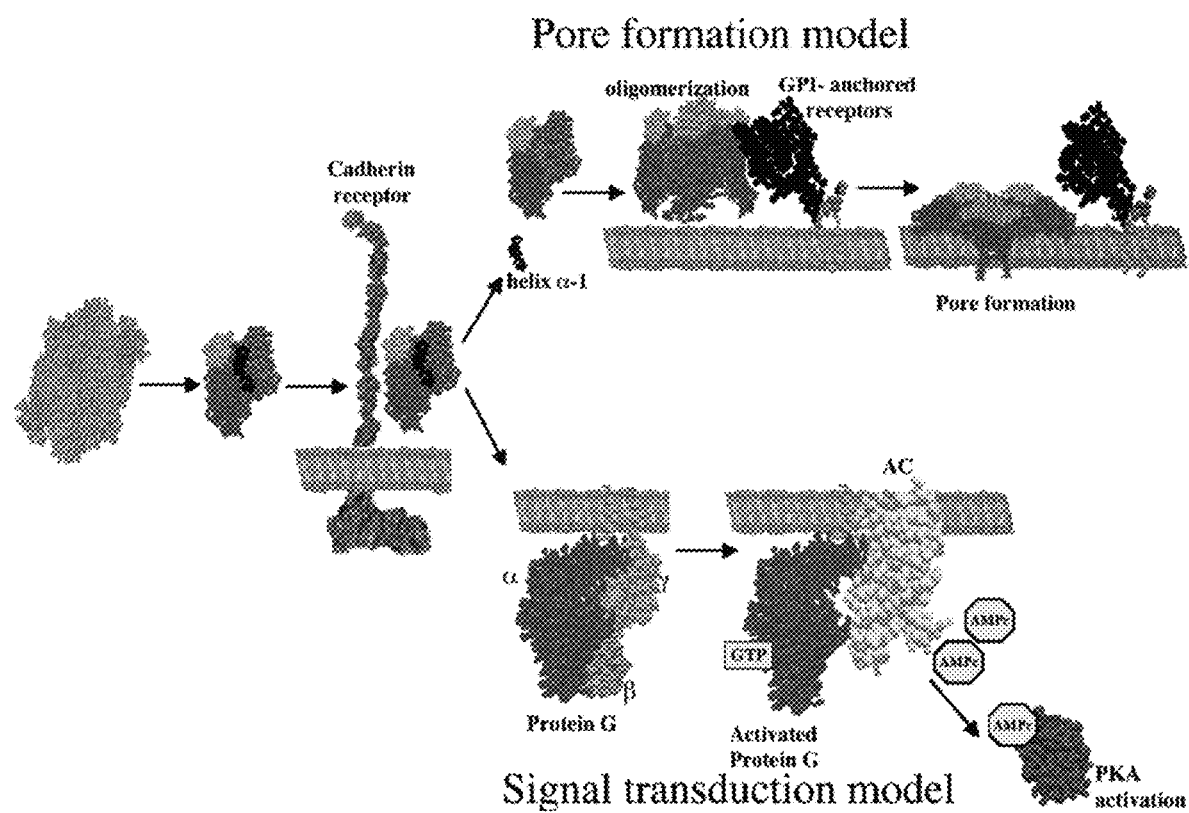
FIG. 1 shows a schematic illustration of Bt toxin mechanisms of action.
Figure 3:
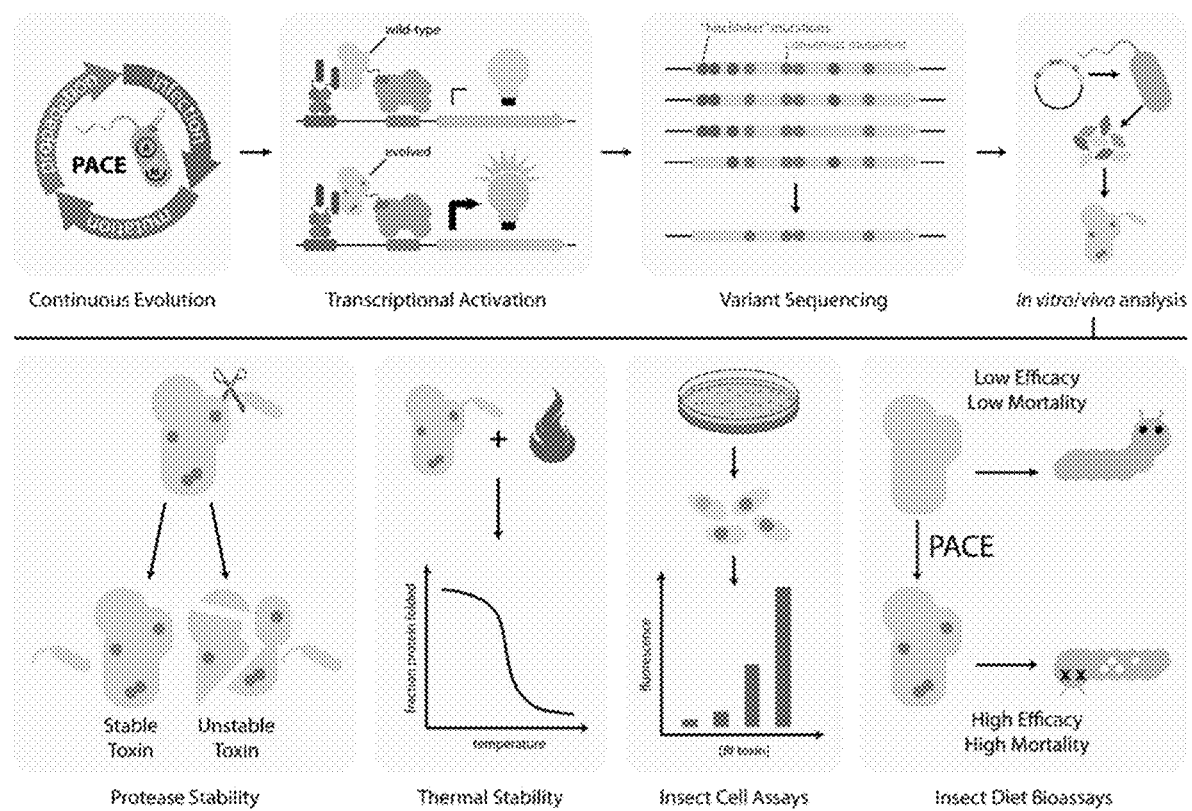
FIG. 3 shows a schematic illustration of the PACE evolution strategy for evolving enhanced Bt toxin variants.

The term "Bt toxin," as used herein, refers to a pesticidal toxin or pesticidal protein that achieves its pesticidal effect(s) upon a target pest by physically interacting with one or more proteins present within and produced by that target pest. In some embodiments, the term "Bt toxin" refers to one or more proteins (e.g., crystal (Cry) protein(s)) that are produced by *Bacillus thuringiensis*, or a subspecies thereof (e.g., *B. thuringiensis* kurstaki, *B. thuringiensis israeliensis*, or *B. thuringiensis* aizawa). Exemplary Bt toxins encoded by a cry gene include: Cry1Aa1-Cry1Aa23, Cry1Ab1-CryAb34, and Cry1Ac1-Cry1Ac38. Other Bt toxins are known in the art, for example those disclosed in Crickmore et al., Revision of the Nomenclature for the *Bacillus thuringiensis* Pesticidal Crystal Proteins, Microbiology and Molecular Biology Reviews (1998) Vol 62: 807-813. A listing of Bt toxins derived from *Bacillus thuringiensis* and related species of bacteria can be found as of the filing date of this application on the world wide web at lifesci.sussex-.ac.uk/home/Neil_Crickmore/Bt/index.html. Generally, pesticidal toxins are useful as insecticides against species within the insect Orders Lepidoptera, Coleoptera, Hemiptera and Diptera, and also as nematicides against plant pathogenic nematodes. Genetically modified plants that express one or more Bt toxins are known in the art.

The term "Bt toxin variant," as used herein, refers to a Bt toxin protein having one or more amino acid variations introduced into the amino acid sequence, e.g., as a result of application of the PACE method, as compared to the amino acid sequence of a naturally-occurring or wild-type pesticidal toxin. Amino acid sequence variations may include one or more mutated residues within the amino acid sequence of the toxin, e.g., as a result of a change in the nucleotide sequence encoding the toxin that results in a change in the codon at any particular position in the coding sequence, the deletion of one or more amino acids (e.g., a truncated protein), the insertion of one or more amino acids, or any combination of the foregoing.

A wild-type Bt toxin refers to the amino acid sequence of a Bt toxin as it naturally occurs in a *Bacillus thuringiensis* genome. An example of a wild-type Bt toxin is the Cry1Ac protein, which is represented by the amino acid sequence set forth in SEQ ID NO: 1.

The term "receptor binding domain," as used herein refers to the portion of the Bt toxin that interacts with a target receptor. Generally, the target receptor is located on a target cell membrane. Several insect cell surface receptors are known to interact with certain Bt toxins, including cadherin-like proteins (CADR), glycosyl-phosphatidyl-inositol (GPI)-anchored aminopeptidase-N (APN), GPI-anchored alkaline phosphatase (ALP) and a 270 kDa glycol-conjugate, however, no single Bt toxin has been shown to interact with more than one of these receptor proteins. For most Bt toxins, the specific receptor that is the target for binding in a target insect species is not known.

Many Bt toxins are comprised of three distinct structural domains, and the ligand (receptor) binding domain of any particular Bt toxin usually is made up of the exposed regions (solvent accessible regions) of the second and third structural domains, commonly referred to as domain II and domain III.

The term "toxin binding region (TBR)," refers to the epitope or epitopes of a target pest protein (commonly referred to as a receptor) that, when exposed to a pesticidal protein that exhibits toxic effects upon the target pest, interacts with the pesticidal protein. Generally, a TBR of any particular insect protein that functions as such a receptor comprises several amino acid residues that interact with a pesticidal protein. A toxin binding region can comprise several (e.g., 1, 2, 3, 4, or more) epitopes (e.g., residues) that bind to Bt toxin.

The term "higher affinity," as used herein, with respect to any particular receptor protein, refers to the increased binding strength of a first protein relative to the binding strength of a second protein, for example, under conditions in which both the first and second protein interact with and bind to the receptor. For example, if protein A has a binding affinity of 1×Kd to receptor Y and protein B has a binding affinity of 3×Kd to receptor Y, then protein A binds to receptor Y with higher affinity than protein B.

Continuous Evolution

The term "continuous evolution," as used herein, refers to an evolution procedure, in which a population of nucleic acids is subjected to multiple rounds of (a) replication, (b) mutation (or modification of the primary sequence of nucleotides of the nucleic acids in the population), and (c) selection to produce a desired evolved product, for example, a novel nucleic acid encoding a novel protein with a desired activity, wherein the multiple rounds of replication, mutation and selection can be performed without investigator interaction and wherein the processes under (a)-(c) can be carried out simultaneously. Typically, the evolution procedure is carried out in vitro, for example, using cells in culture as host cells. In general, a continuous evolution process provided herein relies on a system in which a gene of interest is provided in a nucleic acid vector that undergoes a life-cycle including replication in a host cell and transfer to another host cell, wherein a critical component of the life-cycle is deactivated and reactivation of the component is dependent upon a desired variation in amino acid sequence of a protein encoded by the gene of interest.

In some embodiments, the gene of interest is transferred from cell to cell in a manner dependent on the activity of the gene of interest. In some embodiments, the transfer vector is a virus infecting cells, for example, a bacteriophage, or a retroviral vector. In some embodiments, the viral vector is a phage vector infecting bacterial host cells. In some embodiments, the transfer vector is a conjugative plasmid transferred from a donor bacterial cell to a recipient bacterial cell.

In some embodiments, the nucleic acid vector comprising the gene of interest is a phage, a viral vector, or naked DNA (e.g., a mobilization plasmid). In some embodiments, transfer of the gene of interest from cell to cell is via infection, transfection, transduction, conjugation, or uptake of naked DNA, and efficiency of cell-to-cell transfer (e.g., transfer rate) is dependent on an activity of a product encoded by the gene of interest. For example, in some embodiments, the nucleic acid vector is a phage harboring the gene of interest and the efficiency of phage transfer (via infection) is dependent on an activity of the gene of interest in that a protein required for the generation of phage particles (e.g., pIII for M13 phage) is expressed in the host cells only in the presence of the desired activity of the gene of interest.

For example, some embodiments provide a continuous evolution system, in which a population of viral vectors comprising a gene of interest to be evolved replicates in a flow of host cells, e.g., a flow through a lagoon, wherein the viral vectors are deficient in a gene encoding a protein that is essential for the generation of infectious viral particles, and wherein that gene is comprised in the host cell under the control of a conditional promoter that can be activated by a gene product encoded by the gene of interest, or a mutated version thereof. In some embodiments, the activity of the conditional promoter depends on a desired function of a gene product encoded by the gene of interest. Viral vectors, in which the gene of interest has not acquired a desired function as a result of a variation of amino acids introduced into the gene product protein sequence, will not activate the conditional promoter, or may only achieve minimal activation, while any mutations introduced into the gene of interest that confers the desired function will result in activation of the conditional promoter. Since the conditional promoter controls an essential protein for the viral life cycle, e.g., pIII, activation of this promoter directly corresponds to an advantage in viral spread and replication for those vectors that have acquired an advantageous mutation.

The term "flow," as used herein in the context of host cells, refers to a stream of host cells, wherein fresh host cells are being introduced into a host cell population, for example, a host cell population in a lagoon, remain within the population for a limited time, and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon.

Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

The term "phage-assisted continuous evolution (PACE)," as used herein, refers to continuous evolution that employs phage as viral vectors.

Viral Vectors

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetyl cytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methyl cytidine, arabinose, and hexose), or modified phosphate groups (e.g., phosphorothioates and 5'-N-phosphoramidite linkages).

The term "protein," as used herein refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, cco.caltech.edu/~dadgrp/Unnatstruct.gif on the world wide web, which displays structures of non-natural amino acids that have been successfully incorporated into functional ion channels) and/or amino acid analogs as are known in the art may alternatively be employed. Also, one or more of the amino acids in an inventive protein (e.g., a Bt toxin) may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "gene of interest," as used herein, refers to a nucleic acid construct comprising a nucleotide sequence encoding a gene product (e.g., a protein) of interest, for example, a gene product to be evolved in a continuous evolution process as provided herein. The term includes any variations of a gene of interest that are the result of a continuous evolution process according to methods provided herein. For example, in some embodiments, a gene of interest is a nucleic acid construct comprising a nucleotide sequence encoding a protein to be evolved (e.g., a Bt toxin), cloned into a viral vector, for example, a phage genome, so that the expression of the encoding sequence is under the control of one or more promoters in the viral genome. In other embodiments, a gene of interest is a nucleic acid construct comprising a nucleotide sequence encoding a protein to be evolved and a promoter operably linked to the encoding sequence. For example, a gene of interest encoding a Bt toxin to be evolved may be expressed in host cells, wherein the evolution of the Bt toxin is dependent upon the interaction of the Bt toxin with a second protein expressed from an accessory plasmid of a viral vector (e.g., the TBR of a Bt toxin receptor expressed by an M13 phage). When cloned into a viral vector, for example, a phage genome, the expression of the encoding sequence of such genes of interest is under the control of the heterologous promoter and, in some embodiments, may also be influenced by one or more promoters comprised in the viral genome.

The term "function of a gene of interest," as interchangeably used with the term "activity of a gene of interest," refers to a function or activity of a gene product, for example, a nucleic acid, or a protein, encoded by the gene of interest. For example, a function of a gene of interest may be an enzymatic activity (e.g., an enzymatic activity resulting in the generation of a reaction product, phosphorylation activity, phosphatase activity, etc.), an ability to activate transcription (e.g., transcriptional activation activity targeted to a specific promoter sequence), a bond-forming activity, (e.g., an enzymatic activity resulting in the formation of a covalent bond), or a binding activity (e.g., a protein, DNA, or RNA binding activity).

The term "promoter" refers to a nucleic acid molecule with a sequence recognized by the cellular transcription machinery and able to initiate transcription of a downstream gene. Typically, a promoter is A promoter can be constitutively active, meaning that the promoter is always active in a given cellular context, or conditionally active, meaning that the promoter is only active under specific conditions. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "viral particle," as used herein, refers to a viral genome, for example, a DNA or RNA genome, that is associated with a coat of a viral protein or proteins, and, in some cases, with an envelope of lipids. For example, a phage particle comprises a phage genome packaged into a protein encoded by the wild type phage genome.

The term "infectious viral particle," as used herein, refers to a viral particle able to transport the viral genome it comprises into a suitable host cell. Not all viral particles are able to transfer the viral genome to a suitable host cell. Particles unable to accomplish this are referred to as non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles.

The term "viral life cycle," as used herein, refers to the viral reproduction cycle comprising insertion of the viral genome into a host cell, replication of the viral genome in the host cell, and packaging of a replication product of the viral genome into a viral particle by the host cell.

In some embodiments, the viral vector provided is a phage. The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; $1^{st}$ edition (December 2004), ISBN: 0849313368; Martha R. J. Clokie and Andrew M. Kropinski: *Bacteriophages: Methods and Protocols, Volume 1: Isolation, Characterization, and Interactions* (*Methods in Molecular Biology*) Humana Press; $1^{st}$ edition (December, 2008), ISBN: 1588296822; Martha R. J. Clokie and Andrew M. Kropinski: *Bacteriophages: Methods and Protocols, Volume 2: Molecular and Applied Aspects* (*Methods in Molecular Biology*) Humana Press; $1^{st}$ edition (December 2008), ISBN: 1603275649; all of which are incorporated herein in their entirety by reference for disclosure of suitable phages and host cells as well as methods and protocols for isolation, culture, and manipulation of such phages).

In some embodiments, the phage is a filamentous phage. In some embodiments, the phage is an M13 phage. M13 phages are well known to those in the art and the biology of M13 phages has extensively been studied. Wild type M13 phage particles comprise a circular, single-stranded genome of approximately 6.4 kb. In certain embodiments, the wild-type genome of an M13 phage includes eleven genes, gI-gXI, which, in turn, encode the eleven M13 proteins, pI-pXI, respectively. gVIII encodes pVIII, also often referred to as the major structural protein of the phage particles, while gIII encodes pIII, also referred to as the minor coat protein, which is required for infectivity of M13 phage particles.

The M13 life cycle includes attachment of the phage to the sex pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild type M13 genome comprises nine promoters and two transcriptional terminators as well as an origin of replication. This series of promoters provides a gradient of transcription such that the genes nearest the two transcriptional terminators (gVIII and IV) are transcribed at the highest levels. In wild-type M13 phage, transcription of all 11 genes proceeds in the same direction. One of the phage-encode proteins, pII, initiates the generation of linear, single-stranded phage genomes in the host cells, which are subsequently circularized, and bound and stabilized by pV. The circularized, single-stranded M13 genomes are then bound by pVIII, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild type genes, and/or inserting a heterologous nucleic acid construct into the genome. M13 does not have stringent genome size restrictions, and insertions of up to 42 kb have been reported. This allows M13 phage vectors to be used in continuous evolution experiments to evolve genes of interest without imposing a limitation on the length of the gene to be involved.

The term "selection phage," as used herein interchangeably with the term "selection plasmid," refers to a modified phage that comprises a gene of interest to be evolved and lacks a full-length gene encoding a protein required for the generation of infective phage particles. For example, some M13 selection phage provided herein comprise a nucleic acid sequence encoding a protein to be evolved, e.g., under the control of an M13 promoter, and lack all or part of a phage gene encoding a protein required for the generation of infective phage particles, e.g., gI, gII, gIII, gIV, gV, gVI, gVII, gVIII, gIX, gX, or gXI, or any combination thereof. For example, some M13 selection phage provided herein comprise a nucleic acid sequence encoding a protein to be evolved, e.g., under the control of an M13 promoter, and lack all or part of a gene encoding a protein required for the generation of infective phage particles, e.g., the gIII gene encoding the pIII protein. In some embodiments, an M13 selection phage comprises a nucleic acid sequence encoding a protein that interacts with the protein to be evolved (e.g., the TBR of a Bt toxin receptor).

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes required for the generation of phage particles. Helper phages are useful to allow modified phages that lack a gene required for the generation of phage particles to complete the phage life cycle in a host cell. Typically, a helper phage will comprise the genes required for the generation of phage particles that are lacking in the phage genome, thus complementing the phage genome. In the continuous evolution context, the helper phage typically complements the selection phage, but both lack a phage gene required for the production of infectious phage particles.

The term "replication product," as used herein, refers to a nucleic acid that is the result of viral genome replication by a host cell. This includes any viral genomes synthesized by the host cell from a viral genome inserted into the host cell. The term includes non-mutated as well as mutated replication products.

Accessory Plasmids and Helper Constructs

The term "accessory plasmid," as used herein, refers to a plasmid comprising a gene required for the generation of infectious viral particles under the control of a conditional promoter. In the context of continuous evolution described herein, the conditional promoter of the accessory plasmid is typically activated by a function of the gene of interest to be evolved. Accordingly, the accessory plasmid serves the function of conveying a competitive advantage to those viral vectors in a given population of viral vectors that carry a gene of interest able to activate the conditional promoter. Only viral vectors carrying an "activating" gene of interest will be able to induce expression of the gene required to generate infectious viral particles in the host cell, and, thus, allow for packaging and propagation of the viral genome in the flow of host cells. Vectors carrying non-activating versions of the gene of interest, on the other hand, will not induce expression of the gene required to generate infectious viral vectors, and, thus, will not be packaged into viral particles that can infect fresh host cells.

In some embodiments, the conditional promoter of the accessory plasmid is a promote the transcriptional activity of which can be regulated over a wide range, for example, over 2, 3, 4, 5, 6, 7, 8, 9, or 10 orders of magnitude by the activating function, for example, function of a protein encoded by the gene of interest). In some embodiments, the level of transcriptional activity of the conditional promoter depends directly on the desired function of the gene of interest. This allows for starting a continuous evolution process with a viral vector population comprising versions of the gene of interest that only show minimal activation of the conditional promoter. In the process of continuous evolution, any mutation in the gene of interest that increases activity of the conditional promoter directly translates into higher expression levels of the gene required for the generation of infectious viral particles, and, thus, into a competitive advantage over other viral vectors carrying minimally active or loss-of-function versions of the gene of interest.

The stringency of selective pressure imposed by the accessory plasmid in a continuous evolution procedure as provided herein can be modulated. In some embodiments, the use of low copy number accessory plasmids results in an elevated stringency of selection for versions of the gene of interest that activate the conditional promoter on the accessory plasmid, while the use of high copy number accessory plasmids results in a lower stringency of selection. The terms "high copy number plasmid" and "low copy number plasmid" are art-recognized and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000. The copy number of an accessory plasmid will depend to a large part on the origin of replication employed. Those of skill in the art will be able to determine suitable origins of replication in order to achieve a desired copy number.

It should be understood that the function of the accessory plasmid, namely to provide a gene required for the generation of viral particles under the control of a conditional promoter the activity of which depends on a function of the gene of interest, can be conferred to a host cell in alternative ways. Such alternatives include, but are not limited to, permanent insertion of a gene construct comprising the conditional promoter and the respective gene into the genome of the host cell, or introducing it into the host cell using an different vector, for example, a phagemid, a cosmid, a phage, a virus, or an artificial chromosome. Additional ways to confer accessory plasmid function to host cells will be evident to those of skill in the art, and the invention is not limited in this respect.

Mutagens and Mutagenesis Promoting Expression Constructs

The term "mutagen," as used herein, refers to an agent that induces mutations or increases the rate of mutation in a given biological system, for example, a host cell, to a level above the naturally-occurring level of mutation in that system. Some exemplary mutagens useful for continuous evolution procedures are provided elsewhere herein and other useful mutagens will be evident to those of skill in the art. Useful mutagens include, but are not limited to, ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene, 3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9) and t-butyl hydroperoxide (BHP) (CAS no. 75-91-2). Additional mutagens can be used in continuous evolution procedures as provided herein, and the invention is not limited in this respect.

Ideally, a mutagen is used at a concentration or level of exposure that induces a desired mutation rate in a given host cell or viral vector population, but is not significantly toxic to the host cells used within the average time frame a host cell is exposed to the mutagen or the time a host cell is present in the host cell flow before being replaced by a fresh host cell.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene. In some embodiments, the gene is a GATC methylase gene, for example, a deoxyadenosine methylase (dam methylase) gene. In some embodiments, the gene is involved in binding of hemimethylated GATC sequences, for example a seqA gene. In some embodiments, the gene is involved with repression of mutagenic nucleobase export, for example emrR. In some embodiments, the gene is involved with inhibition of uracil DNA-glycosylase, for example a Uracil Glycosylase Inhibitor (ugi) gene. In some embodiments, the gene is involved with deamination of cytidine (e.g., a cytidine deaminase from *Petromyzon marinus*), for example, cytidine deaminase 1 (CDA1).

Host Cells

The term "host cell," as used herein, refers to a cell that can host a viral vector useful for a continuous evolution process as provided herein. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the invention is not limited in this respect.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector. In some embodiments, the viral vector is a phage and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, XL1-Blue MRF', and DH10B. These strain names are art recognized and the genotype of these strains has been well characterized. It should be understood that the above strains are exemplary only and that the invention is not limited in this respect.

The term "fresh," as used herein interchangeably with the terms "non-infected" or "uninfected" in the context of host cells, refers to a host cell that has not been infected by a viral vector comprising a gene of interest as used in a continuous evolution process provided herein. A fresh host cell can, however, have been infected by a viral vector unrelated to the vector to be evolved or by a vector of the same or a similar type but not carrying the gene of interest. In some embodiments, the host cell is a prokaryotic cell, for example, a bacterial cell.

In some embodiments, the host cell is an *E. coli* cell. In some PACE embodiments, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA$^+$B$^+$Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ‾". In some embodiments, the host cells for M13-PACE are of the genotype F'proA+B+Δ(lacIZY) zzf::Tn10(TetR) lacIQ1PN25-tetR luxCDE/endA1 recA1 galE15 galK16 nupG rpsL(StrR) ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ‾, for example S1030 cells as described in Carlson, J. C., et al. Negative selection and stringency modulation in phage-assisted continuous evolution. *Nat. Chem. Biol.* 10, 216-222(2014). In some embodiments, the host cells for M13-PACE are of the genotype F' proA+B+Δ(lacIZY) zzf::Tn10 lacIQ1 PN25-tetR luxCDE Ppsp(AR2) lacZ luxR Plux groESL/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ−, for example S2060 cells as described in Hubbard, B. P. et al. Continuous directed evolution of DNA-binding proteins to improve TALEN specificity. *Nature Methods* 12, 939-942 (2015).

Pest Control

The term "pest," as used herein, refers to a destructive insect or other animal that attacks crops, livestock, or other subjects (e.g., humans, domesticated animals, etc.). In the context of this disclosure, a pest is generally an insect. However, the skilled artisan recognizes that Bt toxin variants described by the disclosure may be useful against other types of pests, for example parasitic nematodes. The destruction caused by a pest or pests can be physical (e.g., damaging crops or causing physical harm to a subject), mental (e.g., continued irritation from pest activity), economic (e.g., loss of crops due to pest activity), or any combination of the forgoing.

The term "sensitive to treatment with Bt toxin," refers to a pest that can effectively be controlled by treatment with Bt toxin (e.g., a wild-type Bt toxin).

The term "resistant to treatment with Bt toxin," refers to a pest that is refractory to treatment with Bt toxin (e.g., a wild-type Bt toxin). Resistance to Bt toxin generally results from the reduction or absence of binding interactions between a Bt toxin and a cell surface receptor (e.g., a cadherin or cadherin-like receptor) that is present in the resistant subject (e.g., a Bt resistant pest).

DETAILED DESCRIPTION OF THE INVENTION

Some aspects of this disclosure provide variant Bt toxins and methods for producing the same. In some embodiments, the disclosure relates to the use of phage-assisted continuous evolution (PACE) to produce variant Bt toxins. In some embodiments, variant Bt toxins described by the disclosure bind targets (e.g., receptors) in resistant pests with higher affinity than the wild-type Bt toxin from which they are derived and are thus useful for controlling pests that are resistant to wild type Bt toxins. Some aspects of this disclosure provide methods for pest control using the Bt toxin variants provided herein.

Variant Bt Toxins

Some aspects of this disclosure provide variant Bt toxins that are derived from a wild-type Bt toxin and have at least one variation in the amino acid sequence of the protein as compared to the amino acid sequence present within a cognate wild-type Bt toxin or at least one variation in the encoding nucleic acid sequence that results in a change in the amino acid sequence present within a cognate wild type Bt toxin. The variation in amino acid sequence generally results from a mutation, insertion, or deletion in a DNA coding sequence. Mutation of a DNA sequence can result in a nonsense mutation (e.g., a transcription termination codon (TAA, TAG, or TAA) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, also referred to sometimes as a synonymous mutation). In some embodiments, mutation of a DNA sequence results in a non-synonymous (i.e., conservative, semi-conservative, or radical) amino acid substitution.

Wild-type Bt toxins are encoded by genes of the cry gene family, e.g., by the Cry1Ac gene. The amount or level of variation between a wild-type Bt toxin and a variant Bt toxin provided herein can be expressed as the percent identity of the nucleic acid sequences or amino acid sequences between the two genes or proteins. In some embodiments, the amount of variation is expressed as the percent identity at the amino acid sequence level. In some embodiments, a variant Bt toxin and a wild-type Bt toxin are from about 50% to about 99.9% identical, about 55% to about 95% identical, about 60% to about 90% identical, about 65% to about 85% identical, or about 70% to about 80% identical at the amino acid sequence level. In some embodiments, a variant Bt toxin comprises an amino acid sequence that is at least 50%, at least 60%, at least 70%, at least 80%, at least 90%, at least 95%, at least 99%, or at least 99.9% identical to the amino acid sequence of a wild-type Bt toxin.

In some embodiments, a variant Bt toxin is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% identical to a wild-type Bt toxin.

Some aspects of this disclosure relate to variant Cry1Ac proteins comprising an amino acid sequence that is about 70% identical to the amino acid sequence of wild-type Cry1Ac as provided in SEQ ID NO: 1, wherein the protein comprises at least one variation in the amino acid sequence of the protein provided in Table 1.

The amount or level of variation between a wild-type Bt toxin and a variant Bt toxin can also be expressed as the number of mutations present in the amino acid sequence encoding the variant Bt toxin relative to the amino acid sequence encoding the wild-type Bt toxin. In some embodiments, an amino acid sequence encoding a variant Bt toxin comprises between about 1 mutation and about 100 mutations, about 10 mutations and about 90 mutations, about 20 mutations and about 80 mutations, about 30 mutations and about 70 mutations, or about 40 and about 60 mutations relative to an amino acid sequence encoding a wild-type Bt toxin. In some embodiments, an amino acid sequence encoding a variant Bt toxin comprises more than 100 mutations relative to an amino acid sequence encoding a wild-type Bt toxin. Examples of mutations that occur in an amino acid sequence encoding a variant Bt toxin are depicted in Table 1.

Accordingly, in some embodiments, a variant Bt toxin comprises at least 2, at least 3, at least 4, at least 5, at least 6, at least 7, at least 8, at least 9, at least 10, at least 11, at least 12, at least 13, at least 14, or at least 15 mutations provided in Table 1. Particular combinations of mutations present in an amino acid sequence encoding a variant Bt toxin can be referred to as the "genotype" of the variant Bt toxin. For example, a variant Bt toxin genotype may comprise the mutations G158G, S201Y, D487Y, T489A, S507C, and A681T, relative to a wild-type Bt toxin (e.g., SEQ ID NO: 1). Further examples of variant Bt toxin genotypes are shown in Table 2.

In some embodiments, the at least one mutation is selected from the group consisting of: C14W, C14R, F67S, R197G, G267G, T303N, M321K, E331G, A343E, Q352H, T360I, S362P, D383Y, 5403C, N416D, E460K, N462S, D383Y, 5403C, and S581L.

The location of mutations in an amino acid sequence encoding a variant Bt toxin are also contemplated by the disclosure. Generally, mutations may occur in any portion (e.g., N-terminal, interior, or C-terminal) of an amino acid sequence. Mutations may also occur in any functional domain (e.g., the pore-forming domain, the receptor-binding domain, or the sugar-binding domain). In some embodiments, at least one mutation is located in the receptor-binding domain of the Bt variant toxin, which correlates to the portion of the Bt variant toxin that interacts with the TBR of a target pest.

In some aspects, the disclosure relates to variant Bt toxins that bind to receptors in Bt toxin-resistant pests with higher affinity than the wild-type Bt toxin from which they are derived (e.g., Cry1Ac, represented by SEQ ID NO: 1). Generally, binding of a Bt toxin to a receptor is mediated by the interaction between the receptor binding domain (e.g., target binding region) of the Bt toxin and the cell surface receptor of the target cell. Thus, in some embodiments the disclosure provides a protein comprising a receptor binding domain, wherein the receptor binding domain comprises an amino acid sequence that is at least 70%, at least 75%, at least 80%, at least 85%, at least 90%, at least 95%, or at least 99% identical to SEQ ID NO: 1, wherein the receptor binding domain comprises at least one mutation provided in Table 1, and wherein the variant Bt toxin binds a toxin binding region with higher affinity than a protein having the amino acid sequence of SEQ ID NO: 1.

This disclosure relates, in part, to the discovery that continuous evolution methods (e.g., PACE) are useful for producing variant Bt toxins that have altered receptor binding capabilities. In some embodiments, a variant Bt toxin binds to a toxin binding region of a cell surface receptor with higher affinity than the cognate Bt toxin. Several-binding cell surface receptors are known in the art. Examples of such cell surface receptors include, but are not limited to, cadherin-like proteins (CADR), glycosylphosphatidyl-inositol (GPI)-anchored aminopeptidase-N (APN), and GPI-anchored alkaline phosphatase (ALP). Cry1Ac does not bind to, or recognize these as a target receptor. A variant Bt toxin that binds with higher affinity can have an increase in binding strength ranging from about 2-fold to about 100-fold, about 5-fold to about 50-fold, or about 10-fold to about 40-fold, relative to the binding strength of the wild-type Bt toxin from which the variant Bt toxin was derived. Binding strength can be measured or determined using any suitable method known in the art, for example by determining the dissociation constant (Kd) of an interaction.

Production of Variant Bt Toxins Using PACE

In some aspects, the disclosure relates to methods for producing variant Bt toxins using continuous evolution (e.g., PACE). The general concept of PACE technology has been described, for example in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. Application, U.S. Ser. No. 13/922,812, filed Jun. 20, 2013, each of which is incorporated herein by reference. As described by the present disclosure, PACE allows for a gene of interest (e.g., a gene encoding a Bt toxin) in a viral vector to be evolved over multiple generations of viral life cycles in a flow of host cells to acquire a desired function or activity (e.g., increased binding affinity to a toxin binding region in a pest resistant to the wild type Bt toxin, e.g., in a situation in which the wild type Bt toxin has lost the ability to bind to and/or recognize the normal receptor in a particular target pest).

In some aspects, the disclosure provides a method for producing a Bt toxin variant, the method comprising: (a) contacting a population of bacterial host cells with a population of M13 phages comprising a first gene encoding a first fusion protein, and deficient in a full-length pIII gene, wherein (1) the fusion protein comprises a Bt toxin binding region (TBR) and a repressor element, (2) the phage allows for expression of the first fusion protein in the host cells, (3) the host cells are suitable host cells for M13 phage infection, replication, and packaging; and (4) the host cells comprise an expression construct comprising a second gene encoding the pIII protein and a third gene encoding a second fusion protein comprising a Bt toxin and an RNA polymerase, wherein expression of the pIII gene is dependent on interaction of the Bt toxin of the second fusion protein with the TBR of the first fusion protein; (b) incubating the population of host cells under conditions allowing for the mutation of the third gene, the production of infectious M13 phage, and the infection of host cells with M13 phage, wherein infected cells are removed from the population of host cells, and wherein the population of host cells is replenished with fresh host cells that are not infected by M13 phage; (c) isolating a mutated M13 phage replication product encoding an evolved second fusion protein from the population of host cells.

In some embodiments, the incubating of the host cells is for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral life cycles. In certain embodiments, the viral vector is an M13 phage, and the length of a single viral life cycle is about 10-20 minutes.

In some embodiments, the cells are contacted and/or incubated in suspension culture. For example, in some embodiments, bacterial cells are incubated in suspension culture in liquid culture media. Suitable culture media for bacterial suspension culture will be apparent to those of skill in the art, and the invention is not limited in this regard. See, for example, *Molecular Cloning: A Laboratory Manual*, 2nd Ed., ed. by Sambrook, Fritsch, and Maniatis (Cold Spring Harbor Laboratory Press: 1989); Elizabeth Kutter and Alexander Sulakvelidze: *Bacteriophages: Biology and Applications*. CRC Press; 1st edition (December 2004), ISBN: 0849313368; Martha R. J. Clokie and Andrew M. Kropinski: *Bacteriophages: Methods and Protocols, Volume 1: Isolation, Characterization, and Interactions* (*Methods in Molecular Biology*) Humana Press; 1st edition (December, 2008), ISBN: 1588296822; Martha R. J. Clokie and Andrew M. Kropinski: *Bacteriophages: Methods and Protocols, Volume 2: Molecular and Applied Aspects* (*Methods in Molecular Biology*) Humana Press; 1st edition (December 2008), ISBN: 1603275649; all of which are incorporated herein in their entirety by reference for disclosure of suitable culture media for bacterial host cell culture). Suspension culture typically requires the culture media to be agitated, either continuously or intermittently. This is achieved, in some embodiments, by agitating or stirring the vessel comprising the host cell population. In some embodiments, the outflow of host cells and the inflow of fresh host cells is sufficient to maintain the host cells in suspension. This in particular, if the flow rate of cells into and/or out of the culture vessel is high.

Generally, an accessory plasmid is required for selection of viral vectors, for example, the accessory plasmid comprising the gene required for the generation of infectious phage particles that is lacking from the phages being evolved. In some embodiments, an accessory plasmid comprises a first fusion protein comprising a Bt toxin TBR and a repressor element. In some embodiments, the host cells are generated by contacting an uninfected host cell with the relevant vectors, for example, the accessory plasmid and, optionally, a mutagenesis plasmid, and growing an amount of host cells sufficient for the replenishment of the host cell population in a continuous evolution experiment. Methods for the introduction of plasmids and other gene constructs into host cells are well known to those of skill in the art and the invention is not limited in this respect. For bacterial host cells, such methods include, but are not limited to electroporation and heat-shock of competent cells. In some embodiments, the accessory plasmid comprises a selection marker, for example, an antibiotic resistance marker, and the fresh host cells are grown in the presence of the respective antibiotic to ensure the presence of the plasmid in the host cells. Where multiple plasmids are present, different markers are typically used. Such selection markers and their use in cell culture are known to those of skill in the art, and the invention is not limited in this respect.

In some embodiments, the host cell population in a continuous evolution experiment is replenished with fresh host cells growing in a parallel, continuous culture. In some embodiments, the cell density of the host cells in the host cell population contacted with the viral vector and the density of the fresh host cell population is substantially the same.

In some embodiments, the host cell population is contacted with a mutagen. In some embodiments, the cell population contacted with the viral vector (e.g., the phage), is continuously exposed to the mutagen at a concentration that allows for an increased mutation rate of the gene of interest, but is not significantly toxic for the host cells during their exposure to the mutagen while in the host cell population. In other embodiments, the host cell population is contacted with the mutagen intermittently, creating phases of increased mutagenesis, and accordingly, of increased viral vector diversification. For example, in some embodiments, the host cells are exposed to a concentration of mutagen sufficient to generate an increased rate of mutagenesis in the gene of interest for about 10%, about 20%, about 50%, or about 75% of the time.

In some embodiments, the host cells comprise a mutagenesis expression construct, for example, in the case of bacterial host cells, a mutagenesis plasmid. In some embodiments, the mutagenesis plasmid comprises a gene expression cassette encoding a mutagenesis-promoting gene product, for example, a proofreading-impaired DNA polymerase. In other embodiments, the mutagenesis plasmid, including a gene involved in the SOS stress response, (e.g., UmuC, UmuD', and/or RecA). In some embodiments, the mutagenesis-promoting gene is under the control of an inducible promoter. Suitable inducible promoters are well known to those of skill in the art and include, for example, arabinose-inducible promoters, tetracycline or doxycyclin-inducible promoters, and tamoxifen-inducible promoters. In some embodiments, the host cell population is contacted with an inducer of the inducible promoter in an amount sufficient to effect an increased rate of mutagenesis. For example, in some embodiments, a bacterial host cell population is provided in which the host cells comprise a mutagenesis plasmid in which a dnaQ926, UmuC, UmuD', and RecA expression cassette is controlled by an arabinose-inducible promoter. In some such embodiments, the population of host cells is contacted with the inducer, for example, arabinose in an amount sufficient to induce an increased rate of mutation.

The use of an inducible mutagenesis plasmid allows one to generate a population of fresh, uninfected host cells in the absence of the inducer, thus avoiding an increased rate of mutation in the fresh host cells before they are introduced into the population of cells contacted with the viral vector. Once introduced into this population, however, these cells can then be induced to support an increased rate of mutation, which is particularly useful in some embodiments of continuous evolution. For example, in some embodiments, the host cell comprise a mutagenesis plasmid as described herein, comprising an arabinose-inducible promoter driving expression of dnaQ926, UmuC, UmuD', and RecA730 from a pBAD promoter (see, e.g., Khlebnikov A, Skaug T, Keasling J D. *Modulation of gene expression from the arabinose-inducible araBAD promoter*. J Ind Microbiol Biotechnol. 2002 July; 29(1):34-7; incorporated herein by reference for disclosure of a pBAD promoter). In some embodiments, the mutagenesis plasmid is an MP4 mutagenesis plasmid or an MP6 mutagenesis plasmid. The MP4 and MP6 mutagenesis plasmids are described, for example in U.S. Provisional Application Ser. No. 62/149,378, filed on Apr. 17, 2015, the content of which is incorporated herein in its entirety. The MP4 mutagenesis plasmid comprises the following genes: dnaQ926, dam, seqA[17]. The MP6 mutagenesis plasmid comprises the following genes: dnaQ926, dam, seqA, emrR, Ugi, and CDA1[22].

In some embodiments, the fresh host cells are not exposed to arabinose, which activates expression of the above identified genes and, thus, increases the rate of mutations in the arabinose-exposed cells, until the host cells reach the lagoon in which the population of selection phage replicates. Accordingly, in some embodiments, the mutation rate in the host cells is normal until they become part of the host cell population in the lagoon, where they are exposed to the inducer (e.g., arabinose) and, thus, to increased mutagenesis. In some embodiments, a method of continuous evolution is provided that includes a phase of diversifying the population of viral vectors by mutagenesis, in which the cells are incubated under conditions suitable for mutagenesis of the viral vector in the absence of stringent selection for the mutated replication product of the viral vector encoding the evolved protein. This is particularly useful in embodiments in which a desired function to be evolved is not merely an increase in an already present function, for example, an increase in the transcriptional activation rate of a transcription factor, but the acquisition of a function not present in the gene of interest at the outset of the evolution procedure (for example, altered ligand binding specificity). A step of diversifying the pool of mutated versions of the gene of interest within the population of viral vectors, for example, of phage, allows for an increase in the chance to find a mutation that conveys the desired function.

In addition to altering the rate of mutagenesis, the selective stringency of host cells can be tuned. Such methods involving host cells of varying selective stringency allow for harnessing the power of continuous evolution methods as provided herein for the evolution of functions that are completely absent in the initial version of the gene of interest, for example, for the evolution of a transcription factor recognizing a foreign target sequence that a native transcription factor, used as the initial gene of interest, does not recognize at all. Or, for another example, the recognition of a desired target sequence by a DNA-binding protein, a recombinase, a nuclease, a zinc-finger protein, or an RNA-polymerase, that does not bind to or does not exhibit any activity directed towards the desired target sequence.

Other selection schemes for gene products having a desired activity are well known to those of skill in the art or will be apparent from the instant disclosure. Selection strategies that can be used in continuous evolution processes and methods as provided herein include, but are not limited to, selection strategies useful in two-hybrid screens. For example, the variant Bt toxin selection strategy described in more detail elsewhere herein is an example of a receptor recognition selection strategy.

In some embodiments, the stability of Bt toxin variants was enhanced by combinatorial reversion of mutations observed in PACE and subsequent stability screening of the resulting Bt toxin variants. For example, in some embodiments, the methods and strategies for evolving Bt toxin may include reverting back a single mutation or a combination of at least two, at least three, at least four, at least five, at least six, at least seven, at least eight, at least nine, or at least ten mutations observed in mutant Bt toxin clones obtained through PACE, and subsequently measuring the stability of the resulting Bt toxin variants (e.g., the stability in the presence of trypsin or other proteases and/or the thermal stability). In some embodiments, additional desirable parameters may also be assessed (e.g., affinity to a target receptor or toxicity to a target pest). In some embodiments, a strategy for improving PACE-derived Bt toxin variants may include multiple rounds of combinatorial reversion of mutations, e.g., wherein the first round includes the reversal of a single mutation in a number of Bt toxin variants, and subsequent rounds include a systematic combination of reversions that are observed to have a beneficial effect (e.g., on stability or toxicity).

Vectors and Reagents

The invention provides viral vectors for methods related to the continuous evolution of Bt toxin. In some embodiments, phage vectors for phage-assisted continuous evolution are provided. In some embodiments, a selection phage is provided that comprises a phage genome deficient in at least one gene required for the generation of infectious phage particles and a gene of interest (e.g., a gene encoding a Bt toxin).

For example, in some embodiments, the selection phage comprises an M13 phage genome deficient in a gene required for the generation of infectious M13 phage particles, for example, a full-length gIII. In some embodiments, the selection phage comprises a phage genome providing all other phage functions required for the phage life cycle except the gene required for generation of infectious phage particles. In some such embodiments, an M13 selection phage is provided that comprises a gI, gII, gIV, gV, gVI, gVII, gVIII, gIX, gX, and gXI gene, but not a full-length gIII In some embodiments, the selection phage comprises a 3'-fragment of gIII, but no full-length gIII The 3'-end of gIII comprises a promoter and retaining this promoter activity is beneficial, in some embodiments, for an increased expression of gVI, which is immediately downstream of the gIII 3'-promoter, or a more balanced (wild-type phage-like) ratio of expression levels of the phage genes in the host cell, which, in turn, can lead to more efficient phage production. In some embodiments, the 3'-fragment of gIII gene comprises the 3'-gIII promoter sequence. In some embodiments, the 3'-fragment of gIII comprises the last 180 bp, the last 150 bp, the last 125 bp, the last 100 bp, the last 50 bp, or the last 25 bp of gIII In some embodiments, the 3'-fragment of gIII comprises the last 180 bp of gIII.

M13 selection phage is provided that comprises a gene of interest in the phage genome, for example, inserted downstream of the gVIII 3'-terminator and upstream of the gIII-3'-promoter. In some embodiments, the gene of interest is a fusion protein comprising a toxin binding region of a Bt toxin receptor and a repressor element. In some embodiments, the repressor element is a lambda repressor element (lambda phage (λ) cI, or 434 cI), or a Zif268 repressor. In some embodiments, an M13 selection phage is provided that comprises a multiple cloning site for cloning a gene of interest into the phage genome, for example, a multiple cloning site (MCS) inserted downstream of the gVIII 3'-terminator and upstream of the gIII-3'-promoter.

Some aspects of this invention provide a vector system for continuous evolution procedures, comprising of a viral vector, for example, a selection phage, and a matching accessory plasmid. In some embodiments, a vector system for phage-based continuous directed evolution is provided that comprises (a) a selection phage comprising a gene encoding a protein that interacts with the protein to be evolved, wherein the phage genome is deficient in a gene required to generate infectious phage; and (b) an accessory plasmid comprising the gene required to generate infectious phage particle under the control of a conditional promoter, wherein the conditional promoter is activated by the interaction of the protein expressed by the selection phage and the protein to be evolved.

In some embodiments, the selection phage is an M13 phage as described herein. In some embodiments, the selection phage comprises an M13 genome including all genes required for the generation of phage particles, for example, gI, gII, gIV, gV, gVI, gVII, gVIII, gIX, gX, and gXI gene, but not a full-length gIII gene. In some embodiments, the selection phage genome comprises an F1 or an M13 origin of replication. In some embodiments, the selection phage genome comprises a 3'-fragment of gIII gene. In some embodiments, the selection phage comprises a multiple cloning site upstream of the gIII 3'-promoter and downstream of the gVIII 3'-terminator.

In some embodiments, the selection phage does not comprise a full length gVI. GVI is similarly required for infection as gIII and, thus, can be used in a similar fashion for selection as described for gIII herein. However, it was found that continuous expression of pIII renders some host cells resistant to infection by M13. Accordingly, it is desirable that pIII is produced only after infection. This can be achieved by providing a gene encoding pIII under the control of an inducible promoter, for example, an arabinose-inducible promoter as described herein, and providing the inducer in the lagoon, where infection takes place, but not in the turbidostat, or otherwise before infection takes place. In some embodiments, multiple genes required for the generation of infectious phage are removed from the selection phage genome, for example, gIII and gVI, and provided by the host cell, for example, in an accessory plasmid as described herein.

The vector system may further comprise a helper phage, wherein the selection phage does not comprise all genes required for the generation of phage particles, and wherein the helper phage complements the genome of the selection phage, so that the helper phage genome and the selection phage genome together comprise at least one functional copy of all genes required for the generation of phage particles, but are deficient in at least one gene required for the generation of infectious phage particles.

In some embodiments, the accessory plasmid of the vector system comprises an expression cassette comprising the gene required for the generation of infectious phage under the control of a conditional promoter. In some embodiments, the accessory plasmid of the vector system comprises a gene encoding pIII under the control of a conditional promoter the activity of which is dependent on interaction of the protein expressed by the selection phage and the protein to be evolved. In some embodiments, the protein to be evolved is expressed by the host cells. In some embodiments, the protein to be evolved is a Bt toxin (e.g., Cry1Ac, SEQ ID NO:1). In some embodiments, the protein to be evolved is fused to a RNA polymerase that drives expression of the gene encoding pIII by interacting with the conditional promoter. In some embodiments, the RNA polymerase is RNA polymerase zeta (RpoZ) or RNA polymerase alpha (RpoA) and the conditional promoter is a lacZ promoter or a mutant lacZ promoter (e.g., $P_{lacZ-opt}$).

In some embodiments, the vector system further comprises a mutagenesis plasmid, for example, an arabinose-inducible mutagenesis plasmid as described herein (e.g., MP4 or MP6).

In some embodiments, the vector system further comprises a helper plasmid providing expression constructs of any phage gene not comprised in the phage genome of the selection phage or in the accessory plasmid.

Pest Control

In some aspects, the disclosure relates to the surprising discovery that variant Bt toxins produced by continuous evolution are effective in killing pests that are normally refractory or resistant to treatment with the wild-type Bt toxin from which the variant Bt toxins are derived. (e.g., Cry1Ac, SEQ ID NO: 1).

Variant Bt toxins described by the disclosure may be effective against a wide variety of pests, for example insects. In some embodiments, the insects are selected from the group consisting of the insect Orders Lepidoptera, Coleoptera, Hemiptera, and Diptera.

Examples of Lepidoptera include *Zeuzera coffeae*, *Hyalarcta* spp., *Eumeta* spp., *Agrotis Ipsilon*, *Pseudaletia unipuncta*, *Spodoptera frupperda*, *Helicoverpa zea*, *Manduca sexta*, *Manduca quinquemaculata*, *Spodoptera exigua*, *Peridroma saucia*, *Ostrinia nubilalis*, *Colias eurytheme*, *Plathypena scabra*, *Pieris rapae*, *Plutella xylostella*, *Trichoplusia ni*, Evergestos *ro*, Evergestos psa, Evergestos *os*, and Pthorimaea *operculella*.

Examples of Coleoptera include Agroites *mancus*, Limonius agonu, white grub, *Chaetocnema pulicaria*, *Carpophilus lugubris*, *Popilia japonica*, *Diabrotica barberi*, Diabrotia undecimpunctata *howardi*, *Diabrotica virgifera*, *Epitrix cucumeris*, *Epitrix fuscula*, Systena *blanda*, *Leptinotarsa decemlineata*, *Cerotoma trifurcate*, *Epilachna varivestis*, *Phyllotreta striolata*, *Phyllotreta cruciferae*, Acalymma *vittata*, Metriona *bicolor*, Systena *blanda*, *Crioceris asparagi*, *Crioceris duodecimpunctata*, Disonycha *xanthomelas*, *Epitrix* spp., *Leptinotarsa decemlineata*, and Epicauta spp.

Examples of Diptera include *Delia platura*, *Zonosemata electa*, *Delia radicum*, *Delia antique*, *Liriomyza sativae*, *Pegomya hyoscyami*, *Anopheles* spp., *Aedes* spp., *Culex* spp., *Onchocerca volvulus*, *Phlebotomus* spp., Ltuzomyia spp., *Chrysops* spp., *Tabanus* spp., *Glossina* spp., *Musca domestica*, and *Stomoxys* spp.

In some aspects, the disclosure provides methods of pest control, the method comprising providing to a pest a variant Bt toxin. Methods of pest control described herein may therefore be useful for controlling pests that are resistant to treatment with certain known and available wild-type Bt toxins.

Historically, Bt toxin has been used to control populations of pests that damage crops. For example Bt toxin can be topically applied to plants affected by pests as an insecticide. In other cases, plants, such as corn (*Zea mays*), cotton (*Gossypium* sp.), rice (*Oryza sativa* L.), alfalfa (*Medicago sativa*), potato (*Solanum tuberosum*), tomato (*Solanum lycopersicum*), soybean (*Glycine max*), tobacco (*Nicotiana* sp.), and others can be genetically modified to express Bt toxin. Thus, in some embodiments, the disclosure provides cells and/or plants comprising a variant Bt toxin, e.g., in the form of a variant Bt toxin expressed from a recombinant nucleic acid encoding a variant Bt toxin provided herein. In some embodiments, the cell is a plant cell. Suitable methods of engineering plant cells and plants to express genes, including wild-type Bt genes, are well known to those of skill in the art, and such methods can be used to produce plant cells and plants expressing the Bt toxin variants provided herein.

Transgenic plant which expresses a nucleic acid segment encoding a novel Bt toxin variant as described herein can be produced utilizing variations of methods well known in the art. In general, such methods comprise transforming a suitable host cell with a DNA segment which contains a promoter operatively linked to a coding region that encodes one or more of the Bt toxin variants. Such a coding region is generally operatively linked to a transcription-terminating region, whereby the promoter is capable of driving the transcription of the coding region in the cell, and hence providing the cell the ability to produce the encoded toxin in vivo. Vectors, plasmids, cosmids, and DNA segments for use in transforming such cells will generally comprise operons, genes, or gene-derived sequences, either native, or synthetically-derived, and particularly those encoding the disclosed Bt toxin variant proteins. These DNA constructs can further include structures such as promoters, enhancers, polylinkers, or other gene sequences which can have regulating activity upon the particular genes of interest. Without limitation, examples of plant transformation vectors include those derived from a Ti plasmid of *Agrobacterium tumefaciens*, as well as those disclosed, e.g., by Herrera-Estrella (Nature 303:209-213, 1983), Bevan (Nature 304:184-187, 1983), Klee (Bio/Technol. 3:637-642, 1985). Transgenic plants are desirable for increasing the insecticidal resistance of a monocotyledonous or dicotyledonous plant, by incorporating into such a plant a transgenic DNA segment encoding one or more Bt toxin variant proteins which are toxic to insects. In a related aspect, the present disclosure also encompasses a seed produced by the transformed plant, a progeny from such seed, and a seed produced by the progeny of the original transgenic plant, e.g., produced in accordance with the above process. Such progeny and seeds will have a Bt toxin variant protein-encoding transgene stably incorporated into their genome, and such progeny plants will inherit the traits afforded by the introduction of a stable transgene.

Examples of techniques for introducing DNA into plant tissue are disclosed in European Patent Application Publication No. 0 289 479, published Nov. 1, 1988, of Monsanto Company and by Perlak et al. in "Modification of the Coding Sequence Enhances Plant Expression of Insect Control Protein Genes," Proc. Natl. Acad. Sci. USA, 88, pp. 3324-3328 (1991). Examples of methods which can be modified for obtaining transgenic plants that express insect-active proteins include those describing, for example, Cry1A proteins (U.S. Pat. No. 5,880,275), Cry1B (U.S. Patent Application Publication No. 2006/0112447), Cry1C (U.S. Pat. No.

6,033,874), Cry1A/F chimeras (U.S. Pat. Nos. 7,070,982; 6,962,705, and 6,713,063), and a Cry2Ab protein (U.S. Pat. No. 7,064,249), the entire contents of each of which are incorporated herein by reference.

Cells comprising variant Bt toxin can be isolated (e.g., cultured or stored in vitro), or can form part of a plant (e.g., a transgenic plant expressing a variant Bt toxin) or an entire plant, rendering the respective plant resistant to pests susceptible to the variant Bt toxin. Such pests may include, in some embodiments, pests that are resistant or refractory to wild-type Bt toxin.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Materials and Methods

General methods. All PCR reactions were performed using PfuTurbo Cx Hotstart DNA polymerase (Agilent Technologies), VeraSeq ULtra DNA polymerase (Enzymatics) or Phusion U Hot Start DNA Polymerase (Life Technologies). Water was purified using a MilliQ water purification system (Millipore, Billerica Mass.). All plasmids and selection phages were constructed using USER cloning (New England Biolabs). Genes were synthesized as bacterial codon-optimized gBlocks Gene Fragments (Integrated DNA Technologies). All DNA cloning was carried out using NEB Turbo cells (New England Biolabs).

Electrocompetent strain preparation. Strain S1030 was used for all luciferase and plaque assays, as well as continuous evolution experiments. The glycerol stock of S1030 cells was used to seed a 2 mL overnight culture using 2×YT media supplemented with 10 μg/mL tetracycline (Sigma Aldrich), 50 μg/mL streptomycin (Sigma Aldrich), 10 μg/mL fluconazole (TCI America), and 10 μg/mL amphotericin B (TCI America) in a 37° C. shaker at 230 rpm. The saturated culture was diluted 1000-fold in 50 mL of the same supplemented media and grown under the same conditions until it reached mid log-phase ($OD_{600}$ 0.5-0.8). Once the appropriate $OD_{600}$ had been reached, the cells were pelleted in a 50 mL conical tube (VWR) for 5 mins at 10,000 rcf. The supernatant was immediately decanted and the interior of the tube was wiped with a few Kimwipes (Kimberly-Clark) to remove residual media and salts. The cells were resuspended in 25 mL of pre-chilled, sterile filtered 10% glycerol in MilliQ purified water using a pipette to quickly breakup the pellet. The cells were centrifuged and washed an additional three times. After the last centrifugation step, the interior of the tube was wiped with a few Kimwipes to remove residual glycerol solution. The pellet was resuspended in as little volume as possible, typically ~150 μL, and split into 10 μL aliquots for storage. Cells were flash frozen using a liquid $N_2$ bath, then quickly transferred to −80° C. for extended storage. Electrocompetent S1030 cells produced by this method typically yielded $10^7$-$10^8$ colonies/μg plasmid DNA.

General USER cloning. All plasmid and phage materials were constructed via USER cloning. Briefly, primers were designed to include a single internal deoxyuracil base ~15-20 bases from the 5' end of the primer, specifying this region as the USER junction. Criteria for design of the USER junction were: the junction should contain minimal secondary structure, have 45° C.$<T_m<$70° C., and begin with a deoxyadenosine and end with a deoxythymine (to be replaced by deoxyuridine). The USER junction specifies the homology required for correct assembly. PfuTurbo Cx Hotstart DNA polymerase (Agilent Technologies), VeraSeq ULtra DNA polymerase (Enzymatics) or Phusion U Hot Start DNA Polymerase (Life Technologies) are able to use primers carrying deoxyuracil bases, whereas alternative polymerases undergo a phenomenon known as PCR poisoning and do not extend the primer.

All PCR products were purified using MinElute PCR Purification Kit (Qiagen) to 10 μL final volume and quantified using a NanoDrop 1000 Spectrophotometer (Thermo Scientific). For assembly, PCR products carrying complementary USER junctions were mixed in an equimolar ratio (up to 1 pmol each) in a 10 μL reaction containing 15 units Dpnl (NEB), 0.75 units USER (Uracil-Specific Excision Reagent) enzyme (Endonuclease VIII and Uracil-DNA Glycosylase, NEB), 50 mM Potassium Acetate, 20 mM Tris-acetate, 10 mM Magnesium Acetate, 100 μg/ml BSA at pH 7.9 (lx CutSmart Buffer, NEB). The reactions were incubated at 37° C. for 45 min, followed by heating to 80° C. and slow cooling to 22° C. (0.1° C./s). The hybridized constructs were directly used for heat-shock transformation of chemically competent NEB turbo *E. coli* cells according to the manufacturer's instructions. Transformants were selected on 1.8% agar-2×YT plates supplemented with the appropriate antibiotic(s).

For SP cloning, the hybridized constructs were purified using EconoSpin purification columns (Epoch Life Sciences), eluted using 25 μL 10% glycerol, and transformed into electrocompetent S1030 cells carrying the phage responsive AP pJC175e, which produces functional pIII in response to phage infection (this strain is henceforth referred to as S2208). Following recovery for 3-4 hours at 37° C. using unsupplemented 2×YT media, the culture was centrifuged and the supernatant was purified using a 0.22 μm PVDF Ultrafree centrifugal filter (Millipore). The supernatant was diluted in 100-fold increments and used in plaque assays using log-phase 52208 cells. Following overnight at 37° C., single plaques were picked into unsupplemented 2×YT media and grown for ~12 h in a 37° C. at 230 rpm. The supernatant was purified again to yield clonal phage stocks. In all cases, cloned plasmids and phages were prepared using the TempliPhi 500 Amplification Kit (GE Life Sciences) according to the manufacturer's protocol and verified by Sanger sequencing.

Plaque assays. S1030 cells transformed with the AP of interest were grown in 2×YT liquid media supplemented with the appropriate antibiotics to an $OD_{600}$ of 0.6-0.9. The phage supernatant was diluted in three, 100-fold increments to yield 4 total samples (undiluted, $10^{-2}$, $10^{-4}$, $10^{-6}$) to be used for infections. For each sample, 150 μL of cells were added to 10 μL of phage that had been filtered using a 0.22 μm PVDF Ultrafree centrifugal filter (Millipore). Within 1-2 min of infection, 1 mL of warm (~55° C.) top agar (7 g/L bacteriological agar in 2×YT) was added to the phage/cell mixture, mixed by pipetting up and down once, and plated onto quartered plates that had been previously poured with 2 mL of bottom agar (18 g/L bacteriological agar in 2×YT) in each quadrant. The plates were then grown overnight at 37° C. before plaques were observed.

Phage-Assisted Continuous Evolution (PACE). Host cell cultures, lagoons, media, and the PACE apparatus were prepared. The likelihood of recombinant, wild type selection phage ("SP") occurrence in an SP stock increases with extended standing culture growth of SP. To limit the enrichment of these SP during PACE, all SPs are repurified prior to any continuous evolution experiments. Briefly, SPs were plaqued using 52208 cells to yield single plaques. A single plaque was picked into 2 mL 2×YT supplemented with the appropriate antibiotics and grown until the culture reached mid log-phase ($OD_{600}$ 0.5-0.8). The culture was centrifuged using a tabletop centrifuge for 2 min at 10,000 rcf, followed by supernatant filtration using a 0.22 μm PVDF Ultrafree centrifugal filter (Millipore). This short growth time routinely yields titers of $10^6$-$10^8$ pfu/mL.

To prepare the PACE strain, the accessory plasmid (AP) and mutagenesis plasmid (MP) were co-transformed into electrocompetent S1030 cells and recovered using Davis rich media (DRM) to ensure MP repression. Transformations were plated on 1.8% agar-2×YT containing 50 μg/mL carbenicillin, 40 μg/mL chloramphenicol, 10 μg/mL fluconazole, 10 μg/mL amphotericin B, 100 mM glucose (United States Biological) and grown for 12-18 h in a 37° C. incubator. Following overnight growth, 4 single colonies were picked and resuspended in DRM, then serially diluted and plated on 1.8% agar-2×YT containing 50 μg/mL carbenicillin, 40 μg/mL chloramphenicol, 10 μg/mL fluconazole, 10 μg/mL amphotericin B, and either 100 mM glucose or 100 mM arabinose (Gold Biotechnology) and grown for 12-18 h in a 37° C. incubator. Concomitant with this plating step, the dilution series was used to inoculate liquid cultures in DRM supplemented with 50 μg/mL carbenicillin, 40 μg/mL chloramphenicol, 10 μg/mL tetracycline, 50 μg/mL streptomycin, 10 μg/mL fluconazole, 10 μg/mL amphotericin B and grown for 12-18 h in a 37° C. shaker at 230 rpm. Following confirmation of arabinose sensitivity using the plate assay, cultures of the serially diluted colonies still in log-phase growth were used to seed a 25 mL starter culture for the PACE chemostat.

Once the starter culture had reached log-phase density, the 25 mL culture was added directly to 175 mL of fresh DRM in the chemostat. The chemostat culture was maintained at 200 mL and grown at a dilution rate of 1.5-1.6 vol/hr. Lagoons flowing from the chemostats were maintained at 40 mL, and diluted as described for each experiment. Lagoons were supplemented with 25 mM arabinose to induce the MP for 8-16 h prior to infection with packaged SP. Samples were taken at the indicated time points, centrifuged at 10,000 rcf for 2 min, then sterile filtered with a 0.2 μm filter and stored overnight at 4° C. Phage aliquots were titered on 52208 (total phage) and S1030 (wild type or recombinant phage) for all time points.

Mutagenesis during PACE. The basal mutation rate of replicating filamentous phage ($7.2 \times 10^{-7}$ substitutions/bp/generation) is sufficient to generate all possible single but not double mutants of a given gene in a 40 mL lagoon following one generation of phage replication. For the 2,139 bp rpoZ-cry1ac target, a basal mutation rate of $7.2 \times 10^{-7}$ substitutions/bp/generation applied to $2 \times 10^{10}$ copies of the gene (a single generation) in a 40 mL lagoon yields $3.1 \times 10^7$ base substitutions, easily enough to cover all 6,417 single point mutants but not all double mutants. Arabinose induction of MP6 can increase the mutation rate to $7.2 \times 10^{-3}$ substitutions/bp/generation, yielding ~$3.1 \times 10^{11}$ substitutions spread over $2 \times 10^{10}$ copies of the gene after a single generation. This elevated mutation rate is sufficient to cover all possible single ($6.4 \times 10^3$), double ($4.1 \times 10^7$) and triple ($2.6 \times 10^{11}$) mutants after a single phage generation.

Luciferase assays. Expression plasmids (EPs) were co-transformed with an accessory plasmid ("AP") of interest into electrocompetent S1030 cells and plated onto 1.8% agar-2×YT plates with 50 μg/mL carbenicillin and 100 μg/mL spectinomycin. After overnight growth at 37° C., single colonies were each picked into 2 mL DRM supplemented with 50 μg/mL carbenicillin, 100 μg/mL spectinomycin, 10 μg/mL tetracycline, 50 μg/mL streptomycin, 10 μg/mL fluconazole, 10 μg/mL amphotericin B and grown for 12-18 h in a 37° C. shaker at 230 rpm. Following overnight growth, cultures were diluted 1000-fold in a 96-well deep well plate containing 500 μL DRM with 50 μg/mL carbenicillin, 100 μg/mL spectinomycin and the indicated arabinose concentration to induce rpoZ-cry1Ac expression from the EP. After growth with shaking at 37° C. for 4-5 hours, 150 μL of each culture was transferred to a 96-well black wall, clear bottom plate (Costar), and the $OD_{600}$ and luminescence for each well was measured on an Infinite M1000 Pro microplate reader (Tecan).

High-throughput sequencing and oligotype analysis. Raw reads are deposited in the NCBI Sequence Read Archive with accession number PRJNA293870, and all custom scripts used in analysis are available at github.com/MonsantoCo/BadranEtA12015. Illumina reads obtained from each time point were mapped to the SP055-rpoZ-cMyc-Cry1Ac1-d123 reference sequence using bowtie v2.1.0, and the resulting SAM files were combined into a single BAM file using samtools v0.1.19. This BAM file was used as input to freebayes v0.9.21-12-28 g92eb53a to call SNPs, using the command "freebayes-use-best-n-alleles 1-pooled-continuous-use-reference-allele-theta 500000000-min-alternate-fraction 0.01-ploidy 1-region SP055-rpoZ-cMyc-Cry1Ac1-d123:2833-4971." The analysis is encapsulated in the custom script "ill.callsnps.sh." PacBio polymerase reads were demultiplexed with RS_Resequencing_Barcode.1 workflow provided by PacBio. Polymerase reads with quality score lower than 0.80 (defined by the PacBio scoring algorithm) or shorter than 50 bp were filtered. High quality reads were processed into subreads after sequencing primers and adaptors were removed. Circular consensus reads (or reads-of-inserts) were obtained by calling consensus of subreads generated from the same polymerase reads. These circular consensus reads were mapped to the SP055-rpoZ-cMyc-Cry1Ac1-d123 reference sequence using BLASR v1.3.1.142244, and the alignment was exported as an aligned FASTA sequence using the custom script "SAMtoAFA.py." The aligned FASTA was used as input to the oligotyping platform, manually specifying entropy components as the positions at which the Illumina data defined informative SNPs. Only oligotypes that occur at >1% in at least one sample were retained. This methodology resulted in informative changes at 25 of the 27 specified components. Oligotypes with gaps at the specified components, likely due to indels in the PacBio sequencing or alignment, were reassigned to other oligotypes with nucleotides in those positions only when it could be done unambiguously, and discarded otherwise, resulting in a total fraction abundance <1 in FIG. 19. The resulting oligotype percent abundance matrix was read into R and analyzed using the custom script "PedigreeAndMullerPlot.R." The pedigree was refined manually, assuming that single mutant derivatives of previous oligotypes are due to de novo mutation, while double, triple, or greater mutations that can be explained by recombination of previously observed oligotypes was due to recombination, since the latter are highly unlikely to arise by multiple point mutation after the start of the PACE experiment.

High-throughput primary Bt toxin preparation and analysis. Wild-type Cry1Ac was cloned into the Bt expression vector pMON262346 using BspQ1 endonuclease restriction sites. Consensus PACE-evolved Cry1Ac variants were synthesized (Gen9) and cloned into the Bt expression vector pMON262346 using Hot Fusion. Reversion mutants of consensus Cry1Ac PACE variants were generated via PCR with Phusion High-Fidelity DNA polymerase (New England Biolabs) and mutant primers followed by Hot Fusion into the Bt expression vector pMON262346. The resulting plasmids were transformed into the protease-deficient Bt strain EG1065044 703 for protein expression. Cells were grown from single colonies in 96-well plates (Thermo Scientific, AB-0932) overnight in 400 µL Brain Heart Infusion Glycerol (BHIG) media (VWR) supplemented with 5 µg/mL chloramphenicol. Overnight cultures were used to prepare glycerol stocks (15% glycerol final concentration) and stored at −80° C. for future protein expression. Following overnight growth, 10 µL of each culture was used to inoculate 1 mL of complete C2 medium containing 5 µg/mL chloramphenicol in 96-well plates. The plates were incubated at 26° C. with vigorous shaking at 550 rpm in a Multitron shaking incubator (Infors HT) for 72 hr. The cells were harvested by centrifugation at 3,200 G for 15 min at 4° C. The supernatant was decanted and a single 3.5 mm glass bead was added to each well of the plate. The pellet was then resuspended in 1 ml of TX wash buffer composed of 10 mM Tris-HCl, pH 7.5, 0.005% Triton X-100 supplemented with 25 units/mL Benzonase® (EMD Millipore), and 2 mM $MgCl_2$, incubated at room temperature for 30-60 min (with vigorous vortexing every 10 min), then centrifuged at 3,200 G for 15 min at 4° C. The resulting pellet was resuspended and centrifuged under identical conditions two additional times. The washed spore/crystal pellet from each 1-mL culture was solubilized in the 96-well plate using 300 µL of solubilization buffer composed of 50 mM CAPS, pH 11, and 10 mM DTT, then incubated while shaking at room temperature for 1 h. The insoluble debris was pelleted by centrifugation at 3,200 G for 15 min at 4° C., and 200 µL of the supernatant were transferred to a sterile U-bottom 96-well plate. To each well, 10 µL of 0.2 mg/mL trypsin in 1 M Tris-HCl, pH 7.5 was added. The mixture was incubated at 37° C. for 2 h while shaking at 150 rpm, followed by quenching using 2 µL 0.1 M PMSF. The solution was filtered using a Millipore multiscreen plate with a 0.22 µm membrane. Protein stability was assessed by SDS-PAGE and quantified using spot densitometry. Proteins purified using this protocol were tested in downstream insect cell assays.

Secondary Bt toxin purification and analysis. Bt glycerol stocks described above were used for large-scale protein expression and purification. A 2-mL starter culture of BHIG medium supplemented with 5 µg/mL chloramphenicol was inoculated from the glycerol stocks and grown overnight at 280 rpm in a 28° C. shaker. The following day, the saturated culture was transferred into 500 mL complete C2 medium containing 5 µg/mL chloramphenicol in a 2 L baffled flask and grown for an additional 72 h at 26° C. while shaking at 280 rpm. Sporulation and crystal formation in the culture was verified by optical microscopy of a 2-µL aliquot of the saturated Bt culture. Upon confirmation of crystals, the partially lysed sporulated cells were harvested by centrifugation at 10,000 G for 12 min at 4° C. The pellet was then resuspended in 100 mL TX wash buffer composed of 10 mM Tris-HCl, pH 7.5, and 0.005% Triton X-100 supplemented with 0.1 mM PMSF, 25 units/mL Benzonase® (Sigma-Aldrich), and 2 mM $MgCl_2$, incubated at room temperature for 30-60 min (with vigorous vortexing every 10 min), then centrifuged at 3,200 G for 15 min at 4° C. The resulting pellet was resuspended and centrifuged under identical conditions two additional times. The washed spore/crystal pellet was solubilized in 120 mL 50 mM CAPS, pH 11, 10 mM DTT at room temperature for 1 h while shaking at 130 rpm. The solubilized protein was separated from the insoluble debris by centrifugation at 35,000 G for 20 min at 4° C.

The supernatant was transferred to a fresh flask, and then supplemented with 10 mL 0.2 mg/mL Trypsin in 1 M Tris-HCl at pH 7.5. The mixture was incubated at 30° C. for 2-6 h with shaking at 150 rpm and trypsinization was monitored by SDS-PAGE. Once the trypsin digestion reaction was complete, the mixture was centrifuged at 3,200 G for 15 min at 4° C. The clear supernatant was removed and mixed with PMSF to 1 mM final concentration. The sample was loaded on a 5-10 mL Q-Sepharose (GE Healthcare) anion exchange column at a flow-rate of 4 mL/min and the trypsin resistant core of the toxin was eluted in 25 mM sodium carbonate, pH 9 supplemented with 200-400 mM NaCl. Fractions containing the toxin tryptic cores were pooled, concentrated (Millipore Amicon Ultra-15 centrifugal filter Units, Fisher) and 758 loaded on a Hiload Superdex 200 gel filtration column using an ÄKTA chromatography system (GE Healthcare, United Kingdom). The column was pre-equilibrated and run with 25 mM sodium carbonate at pH 10.5 supplemented with 1 mM β-mercaptoethanol. Only the monomer peak of the toxin fractions was collected in each case and concentrated to 1-3 mg/mL. The final protein concentration was quantified by spot densitometry. The quality of the trypsinized toxin was assessed using the peptide mass fingerprinting (PMF) method that was based on in-gel digestion of proteins by trypsin and mass spectrometry (MS) analysis of the resulted peptides.

*T. ni* receptor fragment expression and purification. Custom expression vectors pMON251427 and IS0008 (same as pMON251427 but with wild-type TnCAD) were used to express TnTBR3 and TnCAD fragments in *Escherichia coli*. Both vectors contain an N-terminal MBP-TVMV protease cleavage site tag and a C-terminal 6× histidine tag flanking the receptor fragment of interest, with the ORF driven by the T7 promoter. Expression vectors were transformed into commercial BL21 (λDE3) competent cells (Life Technologies) that had been previously transformed with TVMV protease expression vector (pMON101695; encodes constitutive TVMV protease from a pACYC184 (New England Biolabs) backbone). A single colony was inoculated in 2 mL of LB media supplemented with 50 µg/mL kanamycin and 25 µg/mL chloramphenicol, and grown at 37° C. for 4 h to generate a starter culture, which was used to prepare glycerol stocks and stored at −80° C. for the future protein expression. A second starter culture was inoculated using the BL21 (λDE3) strain glycerol stocks in 2 mL of LB media supplemented with 50 µg/mL kanamycin and 25 µg/mL chloramphenicol and grown in a 25° C. shaker (280 rpm) for 15 h. The culture was transferred into 500 mL of Terrific Broth medium (24 g/L yeast extract, 12 g/L tryptone, and 5 g/L glucose) supplemented with 50 µg/mL kanamycin and 25 µg/mL chloramphenicol, and grown at 37° C. for 4 h at 280 rpm, then transferred to 15° C. and grown for an additional 48 h after supplementation with IPTG to a final concentration of 0.1 mM. The cells were harvested by centrifugation at 10,000 G for 787 12 min at 4° C.

The bacterial cell pellet was resuspended in affinity buffer A (25 mM Tris-HCl at pH 8.0, 0.5 M NaCl, 15 mM imidazole, and 0.2 mM $CaCl_2$) containing 125 units/mL of Benzonase (EMD Millipore), 10,000 units/mL of Chicken egg white lysozyme (Sigma Aldrich) and 1× BugBuster (Novagen). The cell slurry was incubated at room temperature for 15 min, followed by sonication using Cell Disruptor W-0375 (Heat Systems-Ultrasonics) at 45% Duty Cycle (output No. 5) for 30 seconds with 60 second rests for a total of three cycles. The cell lysate was centrifuged at 35,000 G for 20 min at 4° C. The supernatant was loaded onto a 5-mL Ni-NTA column that had been pre-equilibrated using affinity buffer A. After extensive washing with affinity buffer A, the receptor fragment was eluted with the affinity buffer B (25 mM Tris-HCl at pH 8.0, 0.1 M NaCl, 250 mM imidazole, 0.2 mM $CaCl_2$). Fractions containing the receptor fragment were pooled, concentrated and loaded on a Hiload Superdex 200 gel filtration column using an ÄKTA chromatography system (GE Healthcare, United Kingdom). The column was pre-equilibrated and run with 25 mM Tris-HCl at pH 8.0, 0.1 M NaCl, 0.2 mM $CaCl_2$. Dimer and monomer peaks of the *T. ni* TBR3 and CAD fractions were collected separately and concentrated to 1-2 mg/mL. Only TnTBR3 and TnCAD monomers were used for Cry1Ac1 binding studies.

Fluorescence thermal shift (FTS) assays. All assays were performed using a BioRad CFX96 real-time PCR thermal cycler, enabling thermal manipulations and dye fluorescence detection. The fluorescence sensitive dye SYPRO orange (Life Technologies, S6650) was used at a 5× concentration in all assays. The temperature was increased by 0.5° C. each cycle over a temperature range of 25-90° C. Assay reactions were performed in 96-well white PCR plates (Bio-Rad, No. HSP9631), and heat-sealed (Thermo Scientific, No. ALPS3000) to reduce volume loss through evaporation. The data was analyzed using the CFX manager software.

Protein-protein interaction affinity measurement. The OctetQk (ForteBio) and the Dip and Read™ Ni-NTA (NTA) biosensors were used to measure the affinity of Cry1Ac and its variants to immobilized 6×His-TnCAD or TnTBR3 receptor fragments in 25 mM Tris-HCl at pH 8.5, 0.1 M NaCl, 0.1 mg/ml BSA, 0.05% Tween 20 according to the manufacturer's instructions. Octet Data Acquisition 7.1.0.100 software was used for data acquisition, and ForteBio Data Analysis 7 software was used for data analysis. At least four readings at different Cry1Ac1 concentrations (2-100 nM) were used for each receptor fragment-Bt toxin interaction and a global fit was used to calculate binding affinities.

Insect-based cell assays. 519 cells (Life Technologies) were plated in Sf-900™ III SFM (Life Technologies) at a density of 50,000 cells/well in a 96-well optical bottom black plate (Nunc, Thermo Scientific). The cells were incubated at 27° C. overnight to allow for adherence to the plate. Following overnight incubation, the medium was aspirated from the cells and 100 µL of p3 or p4 generation (third or fourth generation of baculovirus amplification in SD cells following initial transfection with plasmid) recombinant baculovirus encoding each receptor diluted in SFM was added to each well. The plates were kept in a humidified environment to prevent evaporation and incubated at 27° C. for 48 h. Receptor expression was confirmed by western blotting. Toxins were diluted to the same protein concentration in 25 mM sodium carbonate at pH 11, supplemented with 1 mM β-mercaptoethanol, followed by an additional 10-fold dilution in unsupplemented Grace's Media with 2 µM SYTOX Green Nucleic Acid Stain (Life Technologies, S7020). The media was removed from the wells without disturbing the attached cells, and the diluted toxins or buffer controls were added to respective wells. The fluorescence was measured on a CLARIOstar microplate reader (BMG Labtech) after incubation for 4 h. The fluorescence intensity of control cells expressing β-glucuronidase (GUS) was subtracted from wells expressing the variable receptor fragments with or without toxins. Replicates were averaged and signal was plotted for each toxin condition.

Primary insect diet bioassays. Insect diet bioassays using the evolved consensus Cry1Ac variants were performed as previously described. Briefly, 200 mL of artificial diet in 96-well plates were overlaid with 20 mL aliquots of toxin Bt spore/crystal or Bt crystal suspension, dried, after which wells were infested with neonate insect eggs suspended in 0.2% agar, dried again, sealed with Mylar sheets, and incubated at 20° C., 60% RH, in complete darkness for 5 days. The plates were scored on day 5 for larval mortality and growth stunting. Each assay was carried out in three independent biological replicates with eight insects per replicate.

Secondary insect diet surface overlay bioassays. An inbred Bt-susceptible laboratory strain of *T. ni*, (designated the Cornell strain), and a Cry1Ac-resistant strain nearly isogenic to the Cornell strain, GLEN-Cry1Ac-BCS, were maintained on a wheat germ-based artificial diet at 27° C. with 50% humidity and a photoperiod of 16 h light and 8 h dark. Diet surface overlay bioassays were conducted to determine the insecticidal activity of the toxins in the susceptible and Cry1Ac-resistant *T. ni*, as previously described. Briefly, 200 µL of toxin solution was spread on the surface of 5 mL of artificial diet in 30-mL plastic rearing cups (diet surface area was ~7 $cm^2$), and 10 neonatal larvae were placed into each rearing cup after the toxin solution had dried. For each bioassay, 7-8 concentrations of the toxin were used and each treatment included five replicates (50 larvae total per concentration). Larval growth inhibition (neonates that did not reach $2^{nd}$ instar after 4 days) and mortality were recorded after 4 days of feeding. The observed larval growth inhibition and mortality were corrected using Abbott's formula. Both $IC_{50}$ and $LC_{50}$ values and their 95% confidence intervals were calculated by probit analysis using the computer program POLO (LeOra Softare, 1997).

Results

Development of a Sensitive PPI Detection Platform

N-hybrid methods enable the detection of native protein-protein interactions. Described here is an n-hybrid system that can rapidly detect protein-protein interactions in vivo.

A bacterial 2-hybrid system (B2H) that robustly reports on protein-protein interactions ("PPIs") in vivo that rely on a DNA-binding domain (typically phage repressor) covalently fused to the "bait" protein, which serves as one of the interacting domains was designed to be compatible with the Phage-Assisted Continuous Evolution (PACE) platform. The partner interacting domain ("prey) is fused to an activation domain, one that binds to the *E. coli* RNA polymerase. On-target interactions between the bait and prey domains result in localization of the RNA polymerase upstream of a reporter gene, typically the bacterial β-galactosidase. PACE has been previously shown to enable the rapid directed evolution of a number of protein classes, requiring minimal researcher intervention and yielding variants with selection-specified properties.

Initial surveying of known mechanisms of transcriptional activation in *E. coli* yielded three proteins: the *E. coli* RNA polymerase alpha (RpoA) and omega (RpoZ), and the T4 phage anti-sigma factor AsiA. AsiA and RpoA yield moderate levels of transcriptional activation, but AsiA is toxic to *E. coli* and requires genomic modifications to native σ70 subunit. RpoZ outperformed both alternative transcriptional activation mechanisms, enabling an average transcriptional activation of 17-fold. Using RpoZ, additional DNA-binding domains: murine zinc finger Zif268 and 434 phage cI repressor were assessed. Both λ and 434 cI outperformed Zif268, likely a consequence of their dimeric nature as compared to monomeric Zif268. Furthermore, repressor tetramerization or the use of monomeric repressor variants enabled modulation of transcriptional activation levels, consistent with changes in bait abundance.

From these observations, the 434 cI repressor and the omega subunit were selected for further optimizations. The degree of transcriptional activation was low (7-fold for RpoA and 17-fold for RpoZ) using the wild type $P_{lacZ}$ promoter. Directed evolution precedent emphasizes the strong relationship between selection dynamic range and the ability to differentiate between variants of similar activities. To construct a system that would be optimized to select for high affinity interactions, the system was further modified such that the highest affinity interactions result in the greatest degree of transcriptional activation, while increasing the dynamic range to enable the detection of weaker interactions. A number of mutated $P_{lacZ}$-derived promoters were surveyed using both RpoA and RpoZ to increase the degree of transcriptional activation. Mutated promoters tested with RpoA resulted in moderate changes to the degree of transcriptional activation. Conversely, the majority of surveyed mutations to the $P_{lacZ}$ promoter using RpoZ resulted in a greater distribution of transcriptional activation. Among the tested promoters, one variant enhanced the transcriptional activation from 17-fold to 200-fold using the RpoZ-HA4/ 434cI-SH2 pair, while moderately reducing the background transcription as compared to the wild type promoter. This sensitized promoter ($P_{lacZ-opt}$) was used for all further analysis and evolution experiments.

Using the described platform, the degree of transcriptional activation can be modulated by manipulations of the RBS (ribosome activating site) driving the reporter gene, DNA-binding domain abundance, operator distance from the $P_{lacZ-opt}$ promoter, and DNA-binding domain-bait linker length. Cumulatively, these results describe a highly sensitized bacterial 2-hybrid system can potently on on-target interactions and can be easily tuned by the investigator.

PPI-PACE Rapidly Evolves Monobody-Antigen Interactions

The previously evolved monobody HA4 binds to the SH2 domain of ABL1 kinase with high affinity (~7 nM). Prior structural elucidation of the interacting pair highlighted a number of binding hotspots necessary for high affinity binding. Among those, HA4 Y87 interacts with the SH2 domain using a phosphate ion at the interface near the phosphotyrosine-binding pocket, potentially mimicking the native interaction. The mutation Y87A in HA4 was found to ablate binding to the SH2 domain, confirming the amino acid sequence variations' functional significance at the interaction interface. When Y87A was introduced into HA4 using the highly sensitized bacterial 2-hybrid system described above, the degree of transcriptional activation was reduced to negligible levels, confirming the ability of the system to report on functional interactions in vivo. The use of this system in PACE was investigated next. An accessory plasmid (AP) was designed which carries two cassettes: (1) the geneIII-luxAB cassette under the control of $P_{lacZ-opt}$ with an upstream 434 operator (OR1), and (2) a low-level constitutive expression cassette encoding the 434cI-SH2. Similarly, a selection phage (SP) encoding the rpoZ-HA4 fusion gene was generated. Importantly, SP encoding the nonmutated HA4 enabled the development of robust, activity-dependent plaques on 52060 cells carrying the cognate AP, whereas SP encoding the HA4 Y87A mutant did not.

To demonstrate the capability of PPI-PACE in evolving a novel protein-protein interactions, the nonfunctional HA4 Y87A mutant was evolved back to the functional HA4 parent monobody. This constitutes an extremely difficult evolution, as successful reversion to the wild type amino acid at this position requires three adjacent mutations (codon at position 87: alanine/GCG to tyrosine/TAT or TAC). Using PACE to enable genetic drift, the $HA4_{Y87A}$ SP was propagated for 66 hours in the absence of selection pressure but under high mutagenesis, after which point the selection pressure was engaged and compared to the absence of genetic drift. In the cases where neither drift nor mutagenesis were engaged or where only mutagenesis was engaged, the phage quickly washed out under constant dilution conditions. However, if a prior drift schedule was included, the phage pool dropped markedly in titer after the first 12 hours, followed by recovery over the next 24 hours, after which the phage were maintained at a roughly stable titer. Sequence analysis of single phage clones from the pool after 48 hours showed the strong enrichment of either tyrosine (3 mutations) or tryptophan (2 mutations) at position 87. While the ability of $HA4_{Y87W}$ to interact with the SH2 domain was not previously reported, the evolution of these 2 amino acids strongly suggests functional significance. These results collectively demonstrate that PPI-PACE can be integrated with enhancements of improved mutagenesis and genetic drift, and can rapidly evolve novel PPIs from inactive starting materials in short timeframes.

Rationale for Novel Bt Toxin Interaction

Among the pests susceptible to Cry1Ac, *Trichoplusia ni* (cabbage looper) has shown widespread resistance in the field. Interestingly, Cry1Ac toxicity in *T. ni* is not mediated through cadherin-like receptor interaction, but instead relies on the ABC transporter ABCC2 and aminopeptidase N (APN1). Field resistance has been shown to occur with changes in either gene, further supporting a mechanism of action that relies on these receptors. In vitro analysis shows high binding affinity of Cry1Ac to these receptors, and no detectable interaction with *T. ni* cadherin-like receptor TnCAD3 (FIG. 2). For example, Sf9 insect cells expressing TnCAD3 are not susceptible to Cry1Ac-mediated toxicity, and TBR fragments of the wild-type receptor show no binding in vitro.

Using the aforementioned sequence analysis, residues known to be critical for Cry1Ac binding were grafted onto the homologous TBR fragment of *T. ni* (designated TnTBR variants). One mutant, TnTBR3, which carried the mutations M1433F/L1436S/D1437A, showed weak affinity to Cry1Ac as measured by gel filtration, ligand blotting, and Biacore. These mutations convert positions known to be important for binding to reflect the consensus of known TBRs from a number of susceptible Lepidopteran species. Using this intermediate, Bt variant proteins with high affinity to TnTBR3 and/or TnCAD3 were evolved.

Continuous Directed Evolution of Cry1Ac Variants with Novel Receptor Specificities To enable the directed evolution of Cry1Ac, APs carrying differential length fragments of TnTBR3 fused to 434cI were constructed and assessed for transcriptional activation levels in the presence of various domains of Cry1Ac fused to RpoZ. Only full-length Cry1Ac (residues 1-690) showed activity towards the TnTBR3 fragments, with TnTBR3 fragment 3 (TnTBR3-F3) showing the greatest degree of transcriptional activation at ~8-fold. To assess if this low level of transcriptional activation was sufficient for PACE, was observed when an SP carrying the RpoZ-Cry1Ac fusion was constructed about 100-fold phage enrichment using a strain carrying the cognate TnTBR3-F3 AP, whereas a control SP lacking an RpoZ fusion was rapidly lost. These results confirm that the weak Cry1Ac/TnTBR3-F3 interaction is sufficient for phage enrichment, and may enable continuous evolution in PACE.

Figure 4:
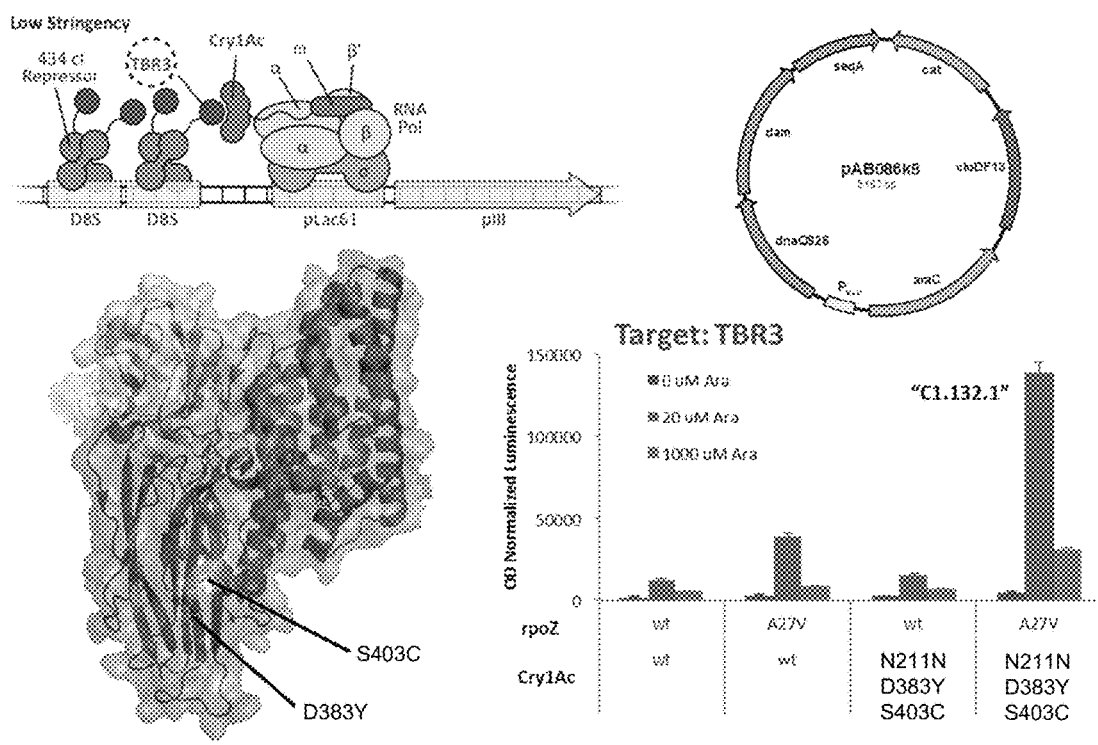
FIG. 4. describes Round 1 of PACE selection of Cry1Ac variants. The low stringency/moderate mutagenesis B2H system is graphically depicted. Mutagenesis plasmid M4 is shown as a vector map. Data on the histogram represent 132 hours of PACE. Consensus mutations of Cry1Ac are located in the receptor binding domain (Domain II).
Figure 6:
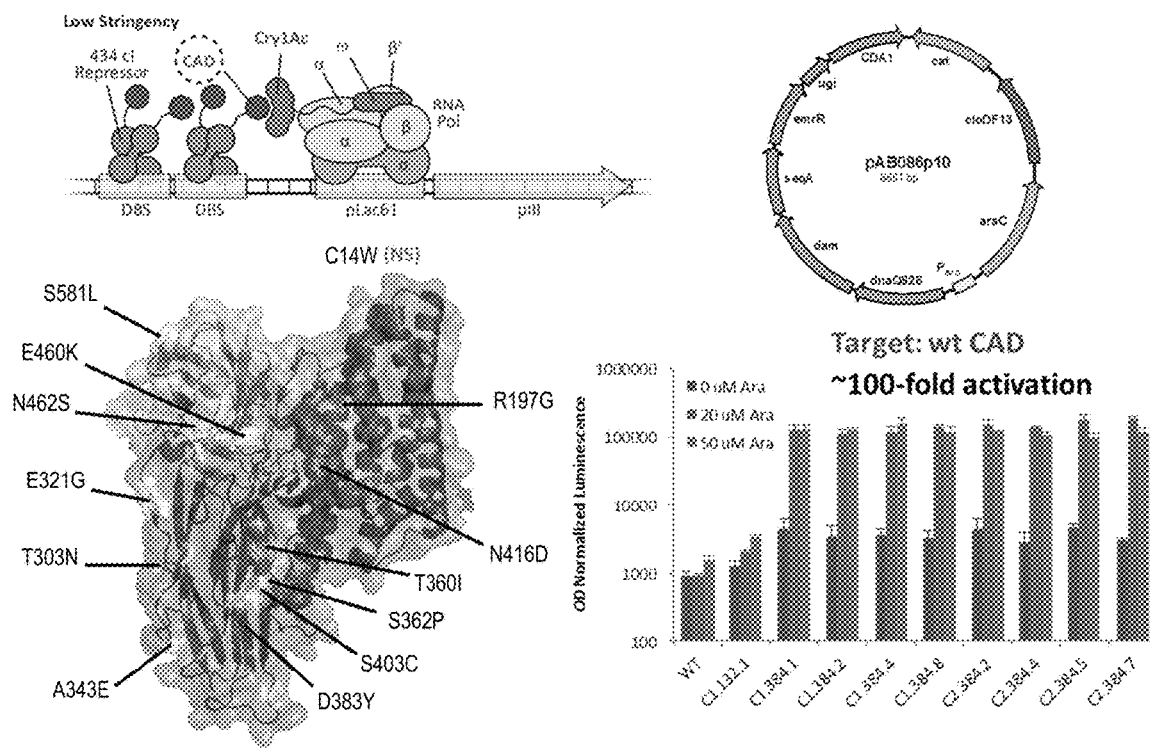
FIG. 6 describes Round 3 of PACE selection of Cry1Ac variants. The intermediate stringency/high mutagenesis B2H system is graphically depicted. Mutagenesis plasmid M6 is shown as a vector map. Data on the histogram represent 384 hours of PACE. The pool converged on the majority of the Cry1Ac mutations depicted.
Figure 7:
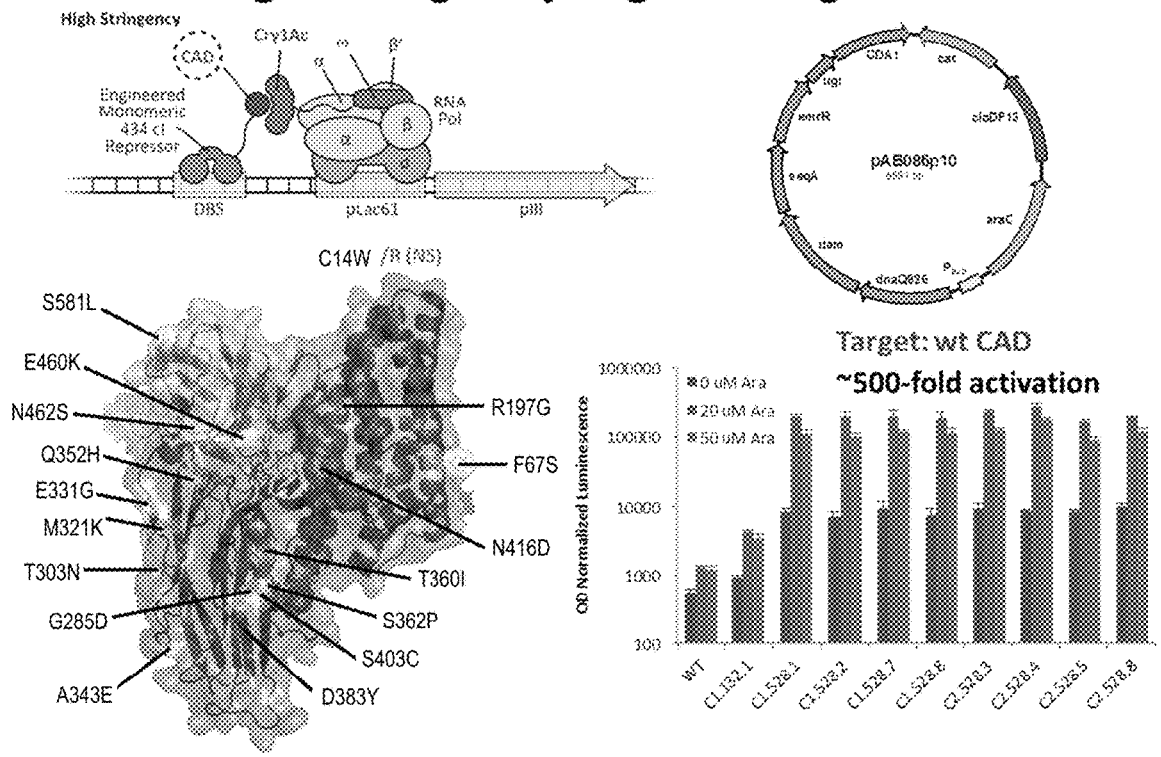
FIG. 7 describes Round 4 of PACE selection of Cry1Ac variants. The high stringency/high mutagenesis B2H system is graphically depicted. Mutagenesis plasmid M6 is shown as a vector map. Data on the histogram represent 528 hours of PACE. Four additional convergent mutations resulted from this round of PACE.
Figure 8A:
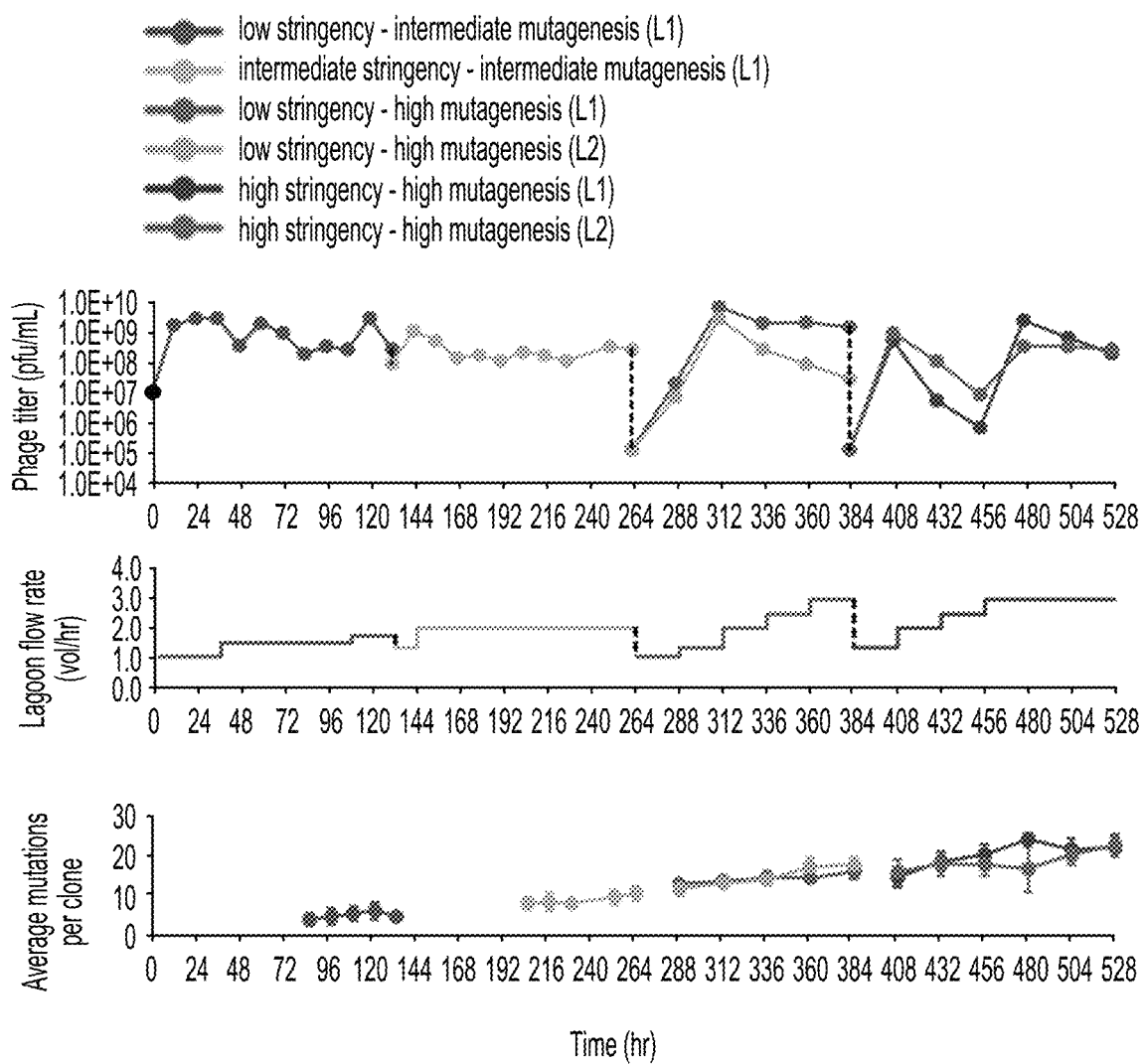
FIGS. 8A-8B illustrate PACE evolution assay data.
Figure 8B:
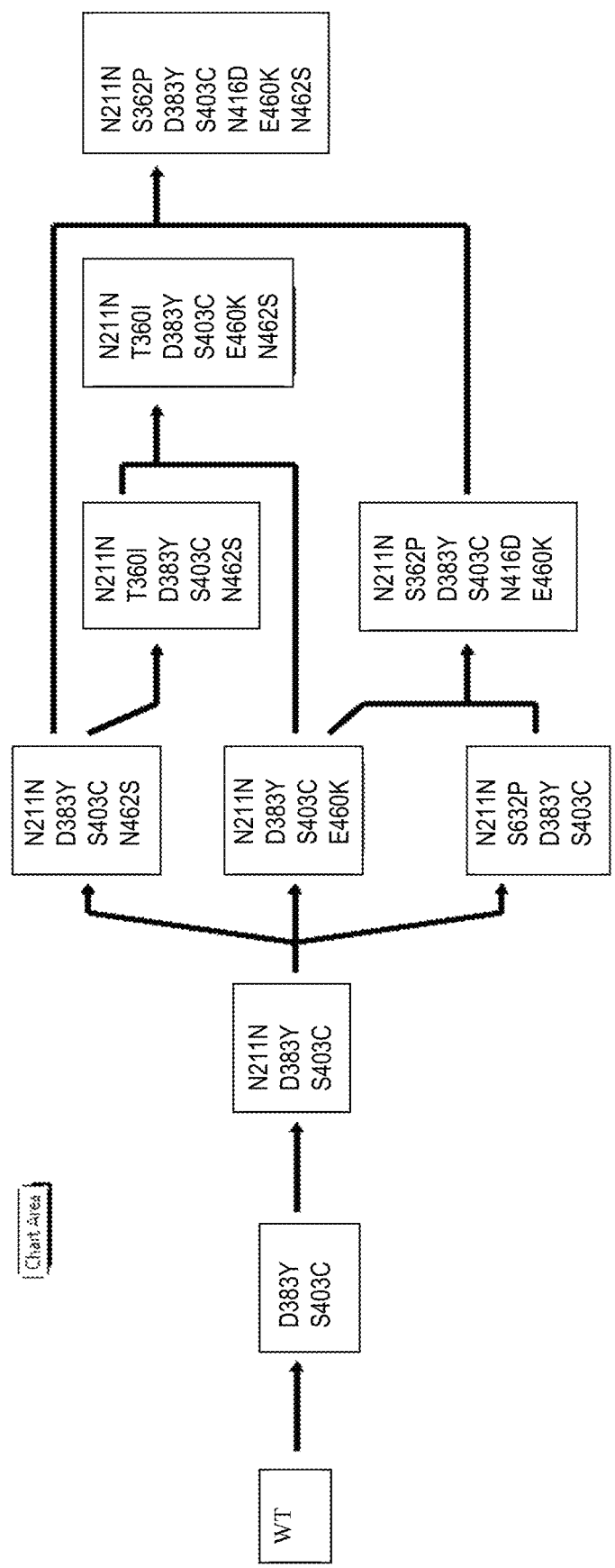

528 hours of PACE were performed using the bacterial 2 hybrid (B2H) selection in four segments (Round 1-4) specifying varying levels of both mutagenesis and selection stringency (FIGS. 3-7, Table 1). To modulate mutagenesis in the system, MP4 was used during TnTBR3 PACE experiments, as the starting material demonstrates weak binding (FIGS. 4-5). Mutagenesis was not greatly enhanced, so as to avoid mutations that destroy the ability of Cry1Ac to kill insects. Later evolutions using TnCAD3 exclusively used MP6, a mutagenesis platform with greater potency and broader mutational spectrum than MP4 (FIGS. 6-7). Further, the selection stringency was varied by increasing the lagoon flow rate and strictly controlling the number of TnTBR3/TnCAD3 fragments participating in Cry1Ac variant recognition through engineering variants of the 434cI repressor and operator(s). At the end of every 120-144 hours segment, the ability of single clones to activate transcription on either TnTBR3 or TnCAD3 was assayed.

Single clone sequencing at the end of the first segment (132 hours) showed a strong consensus of two coding mutations in Cry1Ac, and 1 coding mutation in RpoZ (FIG. 4). All mutations together resulted in a 11-fold improvement over activation using the wild-type RpoZ-Cry1Ac fusion. This consensus clone was used for further evolution. At the end of the second segment (264 hours), even greater degrees of transcriptional activation were observed, reaching up to 20-fold above the starting fusion protein. Despite numerous genotypic changes occurring after this segment, no clear consensus emerged. Thus further evolutions utilized the pool derived from 264 h of PACE using the TnTBR3. After an additional 120 hours of PACE using an AP that carried TnCAD3-F3 and MP6, Cry1AC variants with greatly enhanced affinity for TnCAD3, as assessed by the B2H were identified (FIG. 6). Mutations present in Cry1AC are shown in Table 1 (below). Whereas the wild-type toxin doesn't activate transcription when using TnCAD3, single variants from 384 hours of PACE robustly activated transcription, reaching up to 210-fold above background. A further 144 hours using a more stringent AP yielded clones that could activate transcription by up to 500-fold (FIG. 7). Collectively, these results reveal the robust nature of the B2H-PACE platform, as it enables the evolution of protein-protein interactions in the absence of any detectable affinity between the starting materials.

Table 1 below provides a list of mutations that were observed during the four-round PACE experiment described above. Residues are listed in ascending order from top to bottom, left to right and correspond to the residues in the RpoZ-Cry1Ac chimera (SEQ ID NO: 3), in which amino acid positions 1-104 represent the linear amino acid positions in the RpoZ and the remaining amino acids from position 105-712 correspond to the Cry1Ac amino acids as set forth in SEQ ID NO:1. For ease of reference, groups of mutations relating to the same residue have the same shading and are shown consecutively. To identify the corresponding amino acid position in SEQ ID NO:1, reduce the number shown in each row in Table 1 for each substitution by 104. For example, amino acid variant D487Y in Table 1 below corresponds to amino acid variant D383Y in SEQ ID NO: 1. Silent changes to the applicable codon for each amino acid position, if any, are also represented. For example, C113C represents a nucleotide sequence change introduced by PACE in the Cry1Ac coding sequence but which did not alter the naturally occurring amino acid at that position.

TABLE 1

Amino Acid Sequence Changes in Cry1Ac Produced By PACE.

Without Off-Set

| | | | | | | | | | | | |
|---|---|---|---|---|---|---|---|---|---|---|---|
| N106N | I141S | V181V | P224L | R276R | G317G | G385C | F431Y | I476T | G528G | G593G | H643Y | S685S |
| N109N | I141T | I183V | P224S | V278V | E319E | G385D | S432L | I476L | F529F | P594S | H643H | S685L |
| I110I | S144S | I183T | T225A | V280V | E319D | S386L | E435G | G477G | S530S | G595G | N645S | L686L |
| I110V | S144L | I183L | N226S | V280M | R320S | A387A | F436F | I478T | H531R | T597I | V646I | G687G |
| E112D | L145L | E184G | P227S | V280A | V321I | Q388R | T437A | I478L | L533L | G598G | V646V | V690V |
| E112K | T146I | I187I | A228E | G282G | V321A | G389G | F438F | I478M | V536V | G599G | N647D | G691S |
| C113Y | L150L | I187T | A228A | R284K | G323G | G389D | P439F | N479N | R540R | L601L | N647S | G691D |
| C113F | S151N | N188D | A228S | R284G | P324P | G389V | P439S | N479K | R540K | V602V | N647N | V692I |
| C113R | E152K | Q189R | A228V | G286G | D325G | R392G | Y441Y | Q481Q | G542G | L604L | N647K | R693G |
| C113O | F153F | E192G | L229L | D288N | D328N | S393S | G442G | L483L | F543L | N605N | G649G | R693K |
| I114L | V154I | E192A | L229S | A290V | D328Y | I394I | T443T | L486L | N545N | S606R | N650S | R693R |
| Y116S | V154V | E193G | E231H | A290S | Y332H | I394L | M444V | D487Y | S546G | S607S | N650D | N694S |
| N117S | V154G | E193D | E231A | A290A | Y332Y | R395R | A445V | T489A | S546I | G608G | N650T | N694H |
| C118W | V154A | A195T | E232K | A290E | N333N | S396N | A445G | E490D | S547G | N609H | S651L | F695S |
| C118R | P155S | R196K | M233I | T291A | L339L | S396G | N446T | A492T | V548I | N609N | S652P | G697R |
| L119S | G156S | N197T | I235V | N293N | T340T | P397P | A447E | S496S | S549N | I611I | I653V | G697G |
| L119L | A157V | N197V | Q236R | S294R | T342T | N404L | A448V | N498S | S549S | Q612Q | T657T | T698I |
| S120R | G158G | N197D | D239D | S294G | L344L | S405G | A448T | N498T | I550V | R614K | P659P | T698P |
| S120G | L161L | N197S | M240I | S294S | D345D | S405S | A448D | N498I | F556C | R614G | P659S | A699V |
| N121N | G162G | Q198Q | N241S | R295C | I346I | S405R | A448A | A502A | I559V | Y616C | A660V | A699A |
| P122T | V164A | A199A | N241D | N297D | V347L | I406V | P449L | V503V | I559I | Y616S | A662S | V701V |
| P122H | V164V | I200I | S242G | N297N | V347V | I406M | Q450K | Y504Y | I559M | Y616Y | A662T | I702V |
| E123E | D165D | S201Y | S242N | D298N | A348S | T407N | Q450R | R505R | R561R | E618G | T663T | I702R |
| V124V | D165N | S201F | A243T | L299L | L349L | T407A | I453V | K506R | A563A | E618K | T663M | D704D |
| E125E | I166V | L203L | A243V | T300A | P351L | I408V | A455V | S507C | E564K | E618D | S664L | R705R |
| V126A | I166T | E204G | T245A | R301K | S355N | T410T | A455T | C507C | E564G | V619V | L665L | I709L |
| V126L | I166I | E204E | T246P | R301G | R356K | A412T | Q456H | C507F | N566S | V619I | N667D | I709I |
| V126V | I166K | E204I | T246A | L302I | R357K | H413H | L457L | S507N | I569I | I621I | L668L | V711V |
| G128D | I167I | G205G | T246S | I303I | R357H | H413Y | G458G | S507I | A570T | I621V | Q669R | V711A |
| G128S | I167V | G205R | A247T | G304V | R357I | G415G | G460G | T509P | S573S | I621R | S670L | V711S |
| G129R | I167M | G205V | A247D | G304G | I360I | G415D | R463K | T509M | I574I | H622G | S671S | |
| E130K | I167T | L206L | P249S | N305H | V363V | Y416C | T464I | V510A | A579V | F623F | D672N | |
| E130G | G169G | N208N | L250L | N305S | Q365Q | Y416H | T464V | V510V | V580M | T626I | Y675H | |
| R131S | I170I | I212I | V253A | Y306H | E369K | Y416A | L465F | S512S | V580V | T626P | Y675F | |

TABLE 1-continued

| Amino Acid Sequence Changes in Cry1Ac Produced By PACE. | | | | | | | | | | | | |
|---|---|---|---|---|---|---|---|---|---|---|---|---|
| I132T | I170T | I212V | V253V | T307T | Y371Y | Y417C | N465T | L513M | G582G | S627P | F676L | |
| E133K | I170V | I212T | N255D | Y309Y | N373S | S420S | S466P | D514G | N583N | S627S | E677G | |
| E133A | F171S | E215G | Y256H | A310V | N373N | G421G | S466L | I516I | N583K | R629K | S678S | |
| T134A | F171L | S216Y | V258V | V311V | E377A | Q423Q | S466S | I516V | F584L | R629R | A679T | |
| T134I | G172G | R218R | V258A | V311I | E377E | Q423R | S467S | P517P | F584S | V632I | A679S | |
| G135G | P173S | E219K | L260L | R312L | N378D | I424L | T468I | P518T | F584C | V634I | A679A | |
| G135V | P173T | E221D | Y264H | R312R | F379F | M425K | T468S | N520D | G588G | V634V | A681T | |
| G135D | S174F | E221G | V265I | R312H | G381G | S426S | R472R | N522S | S589S | Y636Y | A681V | |
| Y136C | F177S | E221E | Q266Q | Y314F | S382N | A426S | R472S | V523V | V590I | A637V | A681D | |
| Y136Y | A178T | A222T | A267T | Y314S | F383F | S427S | R472K | P524L | I591I | V639A | T683A | |
| Y136S | A178V | A222S | N269N | N315N | F383I | S427A | N475S | R526K | I591V | V639I | T683T | |
| T137A | F179L | A222A | L272L | N315D | R384R | V429A | N475T | Q527K | S592P | T640A | S684F | |
| D140D | L180F | D223D | S273S | T316A | G385S | G430G | N475Y | Q527P | S592L | T640N | S684Y | |
| Relative to SEQ ID NO: 1 | | | | | | | | | | | | |
| I6V | I37S | V77V | P120L | R172R | G213G | G281C | F327Y | I372T | G424G | G489G | H539Y | S581S |
| E8D | I37T | I79V | P120S | V174V | E215E | G281D | S328L | I372L | F425F | P490S | H539H | S581L |
| E8K | S40S | I79T | T121A | V176V | E215D | S282L | E331G | G373G | S426S | G491G | N541S | L582L |
| C9Y | S40L | I79L | N122S | V176M | R216S | A283A | F332F | I374T | H427H | T493I | V542I | G583G |
| C9F | L41L | E80G | P123S | V176A | V217I | Q284R | T333A | I374L | L429L | G494G | V542V | V586V |
| C9R | T42T | I83I | A124E | G178G | V217A | G285G | F334F | I374M | V432V | G495G | N543D | G587S |
| HOL | L46L | I83T | A124A | R180K | G219G | G285D | P335P | N375N | R436R | L497L | N543S | G587D |
| Y12S | S47N | N84D | A124S | R180G | P220P | G285V | P335S | N375K | R436H | V498V | N543N | V588I |
| N13S | E48E | Q85R | A124V | G182G | D221D | R288G | Y337Y | Q377Q | G438G | L500L | N543K | R589G |
| C14W | F49F | E88G | L125L | D184N | D224N | S289S | G338G | L379L | F439L | N501N | G545G | R589K |
| C14R | V50I | E88A | L125S | A186V | D224Y | I290I | T339T | L382L | N441N | S502R | N546S | R589R |
| L15S | V50V | E89G | E127K | A186S | Y228H | I290L | M340V | D383Y | S442G | S503S | N546D | N590S |
| S16R | V50G | E89D | E127A | A186A | Y228Y | R291R | A341V | T385A | S442I | G504G | N546T | N590H |
| S16G | V50A | A91T | E128K | A186E | N229N | S292N | A341G | E386D | S443G | N505H | S547L | F591S |
| P18T | P51P | R92K | M129I | T187A | L235L | S292G | N342T | A388T | V444I | N505D | S548P | G593R |
| P18H | G52S | N93T | I131V | N189N | T236T | P293P | A343E | S392S | S445N | I507I | I549V | G593G |
| V22A | A53V | N93N | Q132R | S190R | T238T | N300L | A344V | N394S | S445S | Q508Q | T553I | T594I |
| V22L | G54G | N93D | D135D | S190G | L240L | S301G | A344T | N394T | 1446V | R510K | P555P | T594P |
| G24D | L57L | N93S | M136I | S190S | D241D | S301S | A344D | N394I | F452C | R510G | P555S | A595V |
| G24S | G58G | Q94Q | N137S | R191C | I242I | S301R | A344A | A398A | I455V | Y512C | A556V | A595A |
| G25R | V60A | A95A | N137D | N193D | V243I | I302V | P345L | V399V | I455I | Y512S | A558S | V597V |
| E26K | V60V | I96I | S138G | N193N | V243V | I302M | Q346K | Y400Y | I455M | Y512Y | A558T | I598V |
| E26G | D61D | S97Y | S138N | D194N | A244S | T303N | Q346R | R401R | R457R | E514G | T559T | I598R |
| R27S | D61N | S97F | A139T | L195L | L245L | T303K | I349V | K402R | A459A | E514K | T559M | D600D |
| I28T | I62V | L99L | A139V | T196A | P247L | I304V | A351V | S403C | E460K | E514D | S560L | R601R |
| E29K | I62T | E100G | T141A | R197K | S251N | T306T | A351T | C403C | E460G | V515V | L561L | I605L |
| E29A | I62I | E100E | T142P | R197G | R252K | A308T | Q352H | C403F | N462S | V515I | N563D | I605I |
| T30A | I62K | E100I | T142A | L198I | R253K | H309H | L353L | S403N | I465I | I517I | L564L | V607V |
| T30I | I63I | G101G | T142S | I199I | R253R | H309Y | G354G | S403I | A466T | I517V | Q565R | V607A |
| G31V | I63V | G101R | A143T | G200V | R253I | G311G | G356G | T405T | S469S | I517R | S566L | V607S |
| G31D | I63M | G101V | A143D | G200G | I256I | G311D | R359K | T405M | I470I | H518H | S567S | S580Y |
| Y32C | I63T | L102L | P145S | N201H | V259V | Y312C | T360I | V406A | A475V | F519F | D568N | F75L |
| Y32Y | G65G | N104N | L146L | N201S | Q261Q | Y312H | T360T | V406V | V476M | T522I | Y571H | A118A |
| Y32S | I66I | I108I | V149A | Y202H | E265K | Y312A | L361F | S408S | V476V | T522P | Y571F | L168L |
| T33A | I66T | I108V | V149V | T203T | Y267Y | Y313C | N361T | L409M | G478G | S523P | F572L | N211D |
| L76F | I66V | I108T | N151D | Y205Y | N269S | S316S | S362P | D410G | N479N | S523S | E573G | R280R |
| D119D | F67S | E111G | Y152H | A206V | N269N | G317G | S362L | 14121 | N479K | R525K | S574S | V325A |
| S169S | F67L | S112Y | V154V | V207V | E273A | Q319Q | S362S | 1412V | F480L | R525R | A575T | N371T |
| T212A | G68G | R114R | V154A | V207I | E273E | Q319R | S363S | P413P | F480S | V528I | A575S | Q423K |
| G281S | P69S | E115K | L156L | R208L | N274D | I320L | T364I | P414T | F480C | V530I | A575A | S488P |
| G326G | P69T | E117D | Y160H | R208R | F275F | M321K | T364S | N416D | G484G | V530V | A577T | T536A |
| N371Y | S70F | E117G | V161I | R208H | G277G | S322S | R368R | N418S | S485S | Y532Y | A577V | S580F |
| Q423P | F73S | E117E | Q162Q | Y210F | S278N | A322S | R368S | V419V | V486I | A533V | A577D | |
| S488L | A74T | A118T | A163T | Y210S | F279F | S323S | R368K | P420L | I487I | V535A | T579A | |
| T536N | A74V | A118S | N165N | N211N | F279I | S323A | N371S | R422K | I487V | V535I | T579T | |

Analysis of PPI-PACE Evolved Cry1Ac Variants

Analysis of single clones from 528 hours highlighted a number of consensus genotypes, encoding proteins that contained from 9 to 14 amino acid sequence changes, most of which localized to the predicted cadherin-binding surface of Cry1Ac (domain II). Oligotyping analysis of long-read sequencing data revealed plausible evolutionary trajectories over the entire course of the experiment (FIGS. 20A-20C). While PACE does not explicitly promote recombination as a mechanism of gene diversification, multiple putative recombination events were observed during the course of Cry1Ac evolution (FIGS. 20A-C). These recombination events, which may arise from multiple phage occasionally infecting the same host cell, yielded seminal, highly functional new variants.

Figure 12:
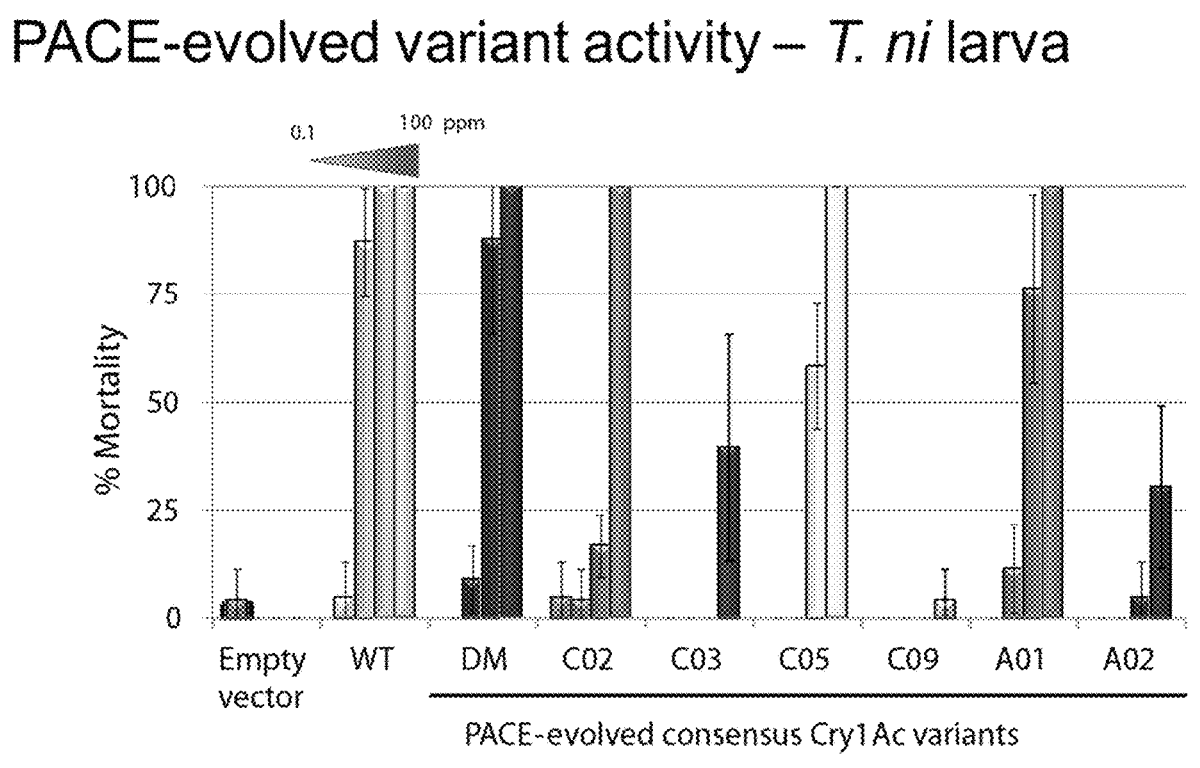

Trypsin-activated Cry1Ac consensus variants showed robust activity in insect-based assays with Sf9 cells expressing the full-length wild type TnCAD3 receptor (FIG. 11). Furthermore, purified activated Cry1Ac variants showed very high binding affinity ($K_d$=18-34 nM) to a TnCAD fragment containing the TBR (TnCAD-FL), highlighting the ability of B2H-PACE to evolve nanomolar protein binders in as short as three weeks (FIG. 14). Consensus amino acid sequence variants demonstrated trypsin sensitivity under conditions in which wild-type Cry1Ac was highly stable, suggesting the PACE evolved consensus variants were proteolytically unstable (FIG. 10). All consensus variants affected *T. ni* larval viability in diet bioassays, but less potently than the wild-type Cry1Ac starting material (FIG. 12). To improve the stability of the evolved Cry1Ac variants, two orthogonal approaches were investigated: combinatorial mutation reversion analysis of evolved consensus variants and removal of destabilizing factors in the PACE strain.

Reversions were conducted on variants exhibiting the fewest number of amino acid sequence changes, for example, Cry1Ac_C05 which contained 9 amino acid changes. Later reversion analysis included consensus variants containing as many as 14 amino acid changes. Using this combinatorial approach, variants having improved properties, for example approaching the stability of wild type Cry1Ac (as measured by melting analysis and proteolytic stability) while retaining binding affinity to TnCAD3 were identified.

Improved Cry1Ac1 Binding Using Continuous Directed Evolution

Several consensus Cry1Ac1 variants containing mutations that were found in multiple PACE-evolved clones were designed, synthesized in expression vectors, expressed in Bt, purified and tested in multiple assays. These consensus Cry1Ac1 variants are listed in Table 2.

*includens*, soybean looper) cadherin and *T. ni* (cabbage looper) cadherin, as measured by increased relative fluorescence intensity of Sytox Green dye. Protein concentrations are shown for each toxin. Short names for consensus PACE-evolved variants (C02, C03, C05, C09, A01 and A02) from Table 2 are used. Each data point is a mean of three measurements, with SD shown.

The data indicate that consensus PACE-evolved variants are much more active than the wild-type Cry1Ac1, despite being tested at lower doses.

TABLE 3

Toxicity of PACE-evolved variants to Sf9 cells expressing *T. ni* cadherin.

|  | Relative fluorescence | Standard deviation |
| --- | --- | --- |
| Buffer | 473 | 22 |
| Empty vector | 766 | 113 |
| Cry1Ac1, 28 ug/ml | 549 | 90 |
| Cry1Ac1_D384Y_S404C, 16 ug/ml | 1041 | 61 |
| Cry1Ac1-C02, 7 ug/ml | 6939 | 120 |
| Cry1Ac1-C03, 4 ug/ml | 7590 | 455 |
| Cry1Ac1-C05, 9 ug/ml | 8189 | 708 |
| Cry1Ac1-C09, 3 ug/ml | 4929 | 281 |

TABLE 2

Consensus Amino Acid Variants in Cry1Ac1. Mutations present in all 6 consensus variants are in bold.

| Consensus PACE-evolved Cry1Ac1 variant: | Amino Acid Sequence Changes in Cry1Ac1 |
| --- | --- |
| VP528_Blue (Cry1Ac1_C02) | Cry1Ac1_D384Y_S404C_E461K_N463S_E332G_T304N_A344E_T361I_S582L_F68S_G286D_C15W |
| VP528_Blue_Red (Cry1Ac1-C03) | Cry1Ac1_D384Y_S404C_E461K_N463S_T304N_A344E_T361I_S582L_C15W_M322K_Q353H_F68S_G286D_E332G |
| VP_Blue_minus (Cry1Ac1-C05) | Cry1Ac1_D384Y_S404C_C15W_T304N_A344E_T361I_E461K_N463S_S582L |
| VP_Red_plus (Cry1Ac1-C09) | Cry1Ac1_D384Y_S404C_R198G_S363P_N417D_E332G_E461K_N463S_S582L_T386A |
| VP528_Red (Cry1Ac1-A01) | Cry1Ac1_D384Y_S404C_E461K_N463S_T304N_A344E_T361I_S582L_C15W_M322K_Q353H |
| VP_Red (Cry1Ac1-A02) | Cry1Ac1_D384Y_S404C_R198G_S363P_N417D_E332G_E461K_N463S_S582L |

Activity of PACE Derived Cry1Ac1 Amino Acid Sequence Variants in Cell-Based Assays PACE derived Cry1Ac1 variants were tested for relative toxicity in insect cell-based assays. Lawns of Sf9 cells, engineered to express cadherin CAD3 from *T. ni* (cabbage looper, FIG. 11, Table 3) or *Chrysodeixis includens* (Table 4), were overlayed with a composition containing membrane-impermeable Sytox Green dye and PACE derived Cry1Ac1 variants pre-treated with trypsin to release the three-domain toxic core. Variants which bind to cadherin receptors aggregate to form pores, allowing the dye to enter the compromised cell membrane, binding to DNA and causing intense green fluorescence.

Figure 11:
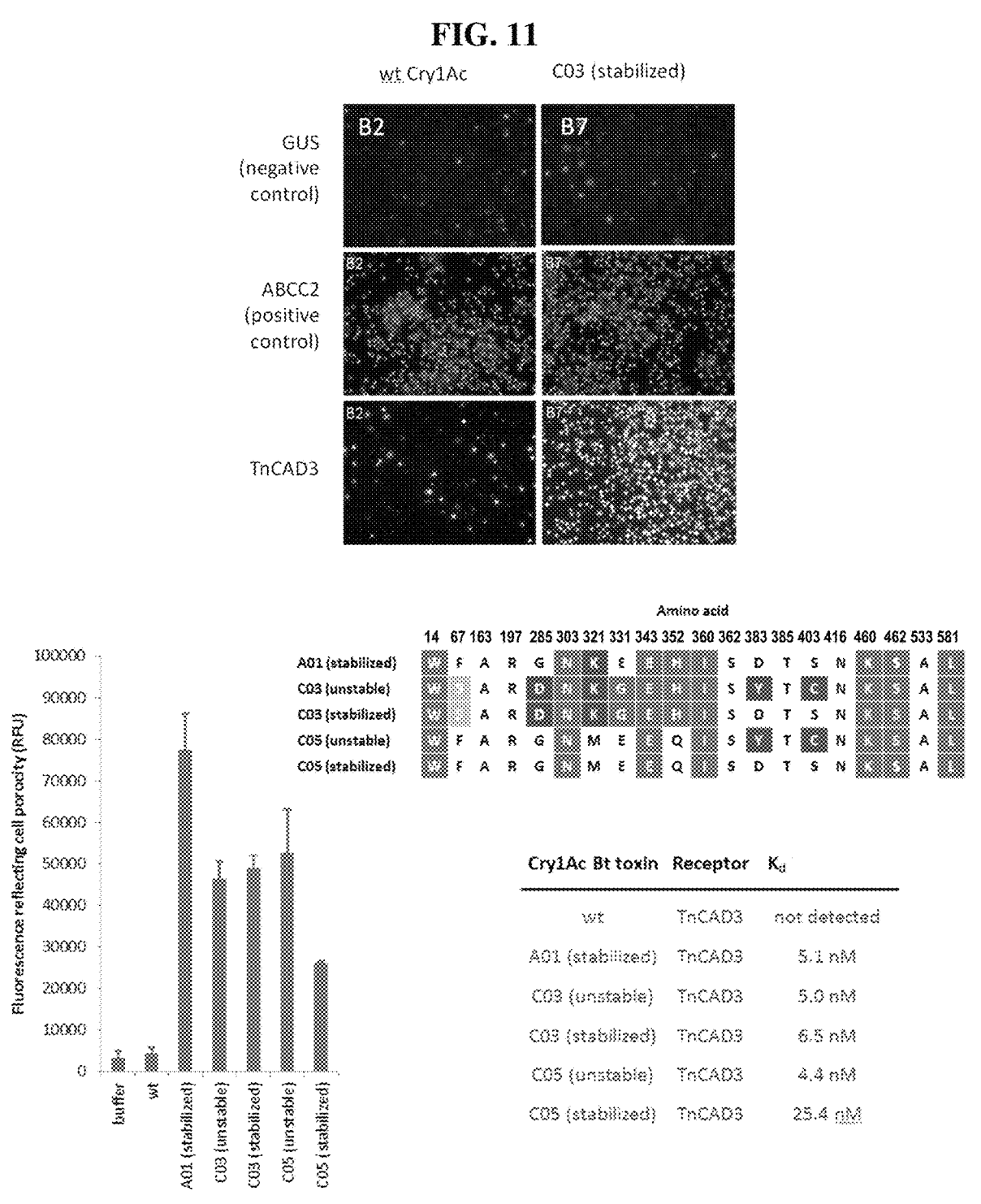

The toxicity of Cry1Ac1 and its variants to Sf9 cells expressing *T. ni* (cabbage looper) cadherin, was measured by increased fluorescence intensity of Sytox Green dye (FIG. 11) Short names for consensus PACE-evolved variants (C02, C03, C05, C09, A01 and A02) are used (see Table 2). Stabilized and non-stabilized ("unstable") variants were tested. FIG. 11 also shows Kd values.

Tables 3 and 4 illustrate the toxicity of Cry1Ac1 and its variants to Sf9 cells expressing *C. includens* (*Chrysodeixis*

TABLE 3-continued

Toxicity of PACE-evolved variants to Sf9 cells expressing *T. ni* cadherin.

|  | Relative fluorescence | Standard deviation |
| --- | --- | --- |
| Cry1Ac1-A01, 4 ug/ml | 10591 | 613 |
| Cry1Ac1 A02, 1 ug/ml | 5425 | 385 |

TABLE 4

Toxicity of PACE-evolved variants to Sf9 cells expressing *C. includens* cadherin.

|  | Relative fluorescence | Standard deviation |
| --- | --- | --- |
| Buffer | 546 | 191 |
| Empty vector | 407 | 70 |
| Cry1Ac1, 28 ug/ml | 116 | 47 |
| Cry1Ac1_D384Y_S404C, 16 ug/ml | 180 | 115 |
| Cry1Ac1-C02, 7 ug/ml | 4468 | 697 |

TABLE 4-continued

Toxicity of PACE-evolved variants to Sf9 cells expressing *C. includens* cadherin.

| | Relative fluorescence | Standard deviation |
|---|---|---|
| Cry1Ac1-C03, 4 ug/ml | 3425 | 624 |
| Cry1Ac1-C05, 9 ug/ml | 3391 | 69 |
| Cry1Ac1-C09, 3 ug/ml | 3286 | 649 |
| Cry1Ac1-A01, 4 ug/ml | 4287 | 572 |
| Cry1Ac1 A02, 1 ug/ml | 3642 | 284 |

Consensus PACE Variants are Susceptible to Proteolysis

This example demonstrates the susceptibility of consensus PACE variants to trypsinolysis. As shown in FIG. 10, following trypsin treatment, an SDS gel band at 66 kDa, the trypsin core (presumably the active three-domain Bt toxin), is visibly present on for the wild-type Cry1Ac1 and double mutant forms of the protein. Almost no visible core toxin is seen in the SDS gels for the PACE-derived Cry1Ac consensus variants.

The upper panel of FIG. 10 shows an SDS gel with solubilized Bt spore/crystal mixtures (S) and trypsin-treated (T) consensus PACE-evolved Cry1Ac1 variants. The band of the toxic core size is pointed to with the red arrow. EV: Empty vector control; DM: Double mutant Cry1Ac1_D384Y_S404C.

Improved Stability of PACE-Derived Cry1Ac1 Variants

In order to improve the proteolytic stability of consensus PACE variants while maintaining activity via combinatorial, combinatorial reversal of PACE-evolved mutations back to the wild type residues was attempted. First, 5 mutations were reversed that were present in all consensus variants (invariable consensus) in Table 2 (in bold), using consensus variants Cry1Ac1_C05 and Cry1Ac1_C09. That set also include a construct that include just the minimum, or invariable consensus (Cry1Ac1_D383Y_S403C_E460K_N462S_S581L). This set included 13 variants.

Next, all possible combinations of reversal mutations for consensus PACE variants Cry1Ac1_C03, Cry1Ac1_C05 and Cry1Ac1_A01 were designed—a total of 276 variants, of which 180 variant genes were generated, for a total of 191 variants.

Of the total of 191 generated variants, 190 variants were expressed in Bt, of which 141 variants formed a stable ~66 kDa core upon treatment with trypsin. An example of SDS gel with trypsin-treated Cry1Ac1 variants is shown in the lower panel of FIG. 10, showing an SDS gel for the wild-type Cry1Ac1 (well G3), consensus PACE-evolved variant Cry1Ac1_C05 and various "stabilization" Cry1Ac1 variants.

Cry1Ac1 variants that form a stable core of ~66 kDa in the presence of trypsin were further screened in cell-based assay with insect cells Sf9 expressing *T. ni* cadherin receptor, to select Cry1Ac1 variants that retained ability for functional binding to cadherin leading to cell membrane disruption. An example of the data from such test is shown in FIG. 15, illustrating the screening of Cry1Ac1 variants (solubilized and trypsinized Bt spore/crystal mixtures) for toxicity to Sf9 cells expressing *T. ni* cadherin expressed as relative fluorescence caused by influx of SytoxGreen fluorescent dye into cells as result of toxin-induced membrane disruption.

Fifteen variants with the highest activity in cell-based assay were selected for protein purification using column chromatography on Superdex Q (ion-exchange) and HiLoad Superdex 200 (size exclusion) columns, and are listed in Table 5.

TABLE 5

Stabilized Cry1Ac1_PACE variants selected for column chromatography purification and detailed functional analysis.

| Name | Amino Acid Changes in Cry1Ac1 |
|---|---|
| Cry1Ac1_pace_mut_0106 | D384Y, S404C, C15W, T361I, N463S, S582L |
| Cry1Ac1_pace_mut_0085 | D384Y, S404C, T304N, T361I, E461K, N463S |
| Cry1Ac1_C05_Y384D_C404S | C15W, T304N, A344E, T361I, E461K, N463S, S582L |
| Cry1Ac1_A01_Y384D_C404S | C15W, T304N, M322K, A344E, Q353H, T361I, E461K, N463S, S582L |
| Cry1Ac1_C03_Y384D_C404S | C15W, F68S, G286D, T304N, M322K, E332G, A344E, Q353H, T361I, E461K, N463S, S582L |
| Cry1Ac1_pace_mut_0133 | E461K, N463S, E332G, T304N, A344E, T361I, S582L, F68S, G286D, C15W |
| Cry1Ac1_pace_mut_0263 | T361I, E461K, S582L |
| Cry1Ac1_pace_mut_0050 | D384Y, S404C, C15W, T361I, E461K |
| Cry1Ac1_pace_mut_0169 | T304N, E461K |
| Cry1Ac1_pace_mut_0038 | D384Y, S404C, T304N, T361I |
| Cry1Ac1_pace_mut_0255 | T304N, N463S, S582L |
| Cry1Ac1_pace_mut_0001 | D384Y, S404C, C15W |
| Cry1Ac1_pace_mut_0170 | T304N, N463S |
| Cry1Ac1_pace_mut_0127 | S404C, E461K, N463S, T304N, A344E, T361I, S582L, C15W, M322K, Q353H, F68S, G286D, E332G |
| Cry1Ac1_pace_mut_0097 | D384Y, S404C, C15W, A344E, T361I, S582L |

These purified proteins were tested for thermal stability in protein melting assay (FIG. 13), tightness of in vitro binding (FIG. 14), and toxicity in cell-based assay with Sf9 cells expressing *T. ni* cadherin (FIG. 16).

Figure 13:
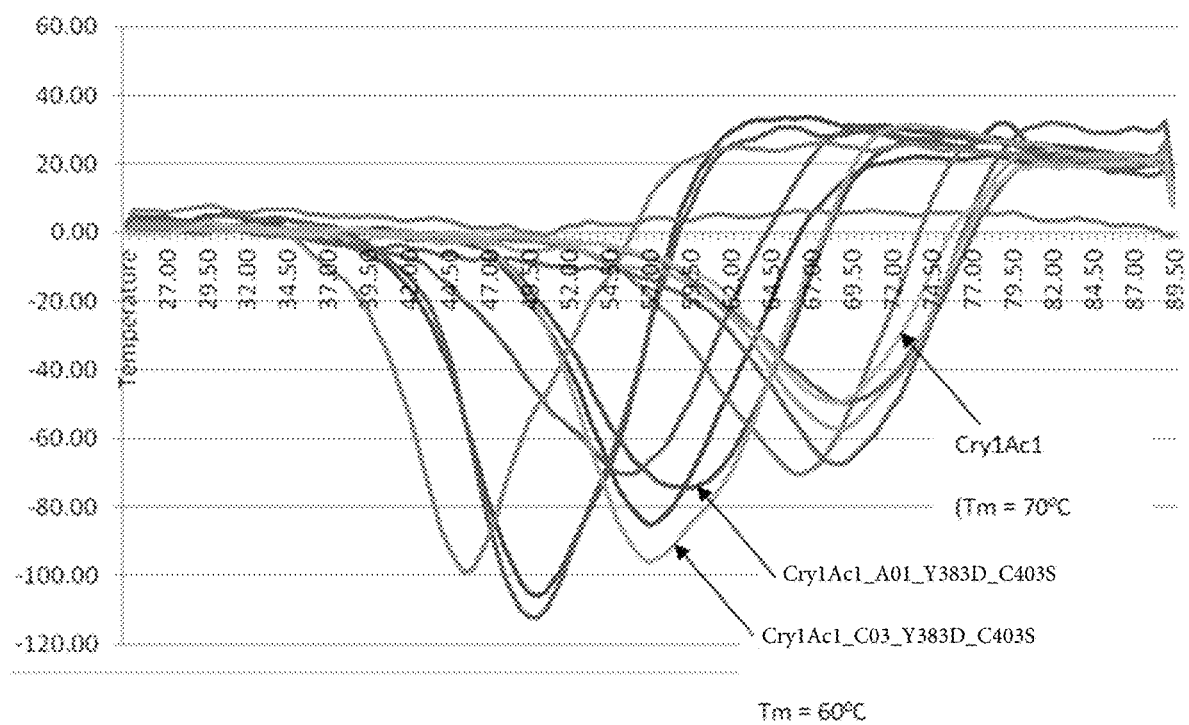
FIG. 13 shows data from a melting assay with purified "stabilization" consensus PACE-evolved Cry1Ac1 variants.
Figure 20A:
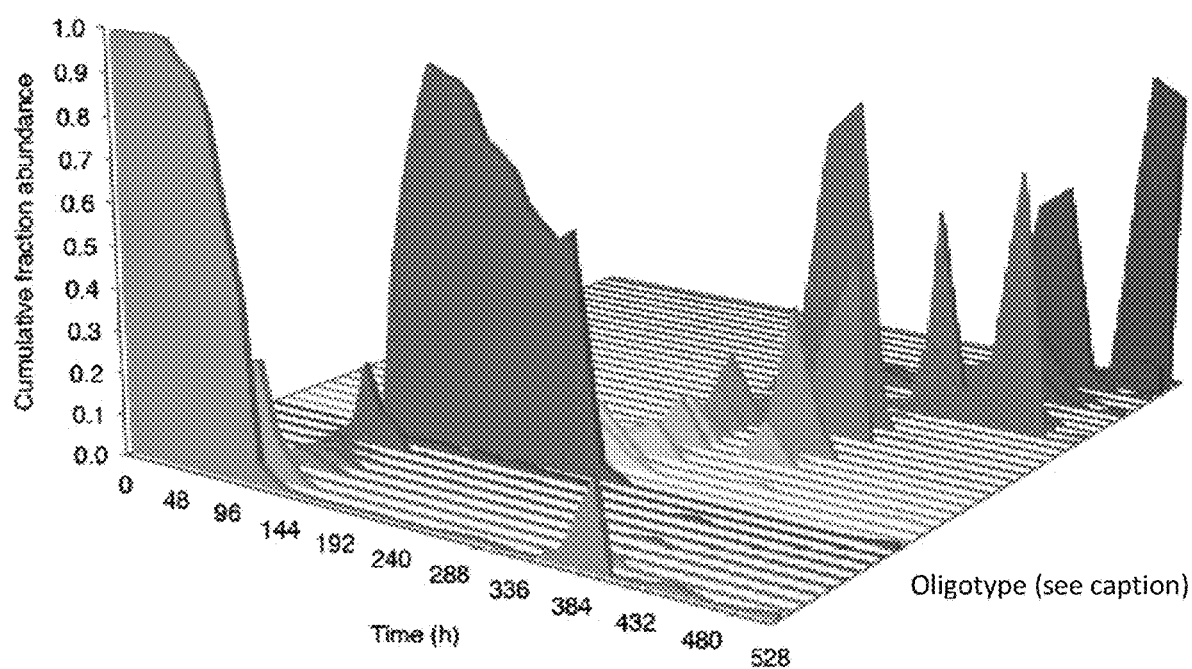
Figure 20C:
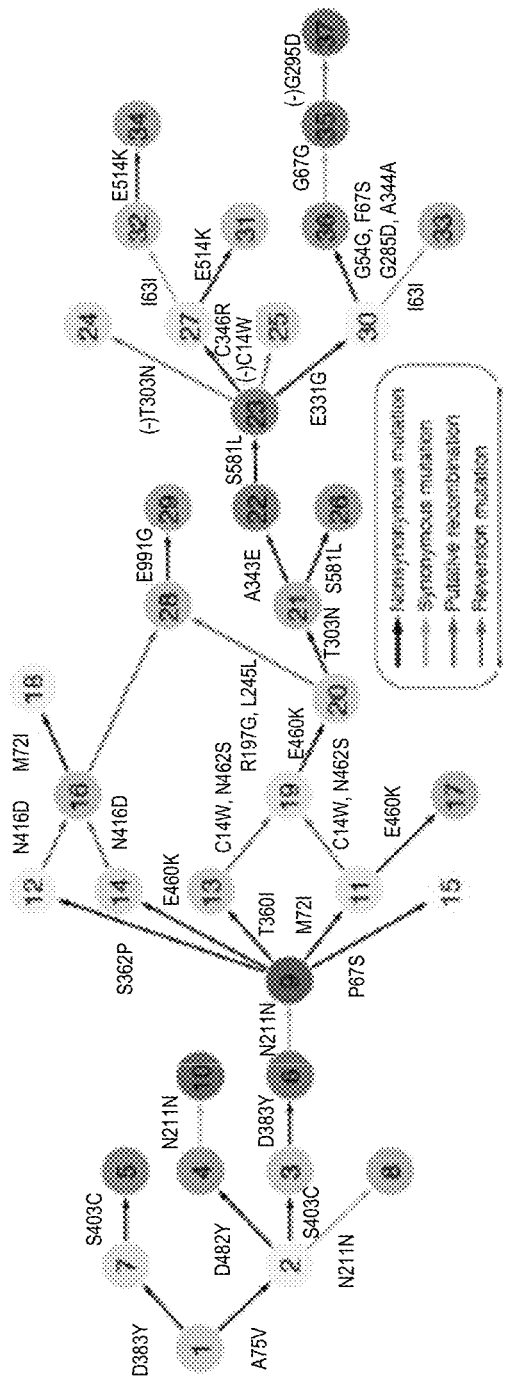

FIG. 13 illustrates data from a protein melting assay with purified "stabilization" consensus PACE-evolved Cry1Ac1 variants.

FIG. 14 illustrates data from in vitro binding of purified stabilized consensus PACE-evolved Cry1Ac1 variants to toxin-binding domain TBR3 from the *T. ni* cadherin, immobilized on a ForteBio chip via His-tag.

FIG. 16 Illustrates the toxicity of purified Cry1Ac1 consensus Cry1Ac1 PACE-evolved variant Cry1Ac1_C03 and stabilized consensus Cry1Ac1 PACE-evolved variants (at 10 µg/ml), to Sf9 cells expressing *C. includens* cadherin.

In Vivo Activity of Evolved Cry1Ac Variants

Based on combination of the above-described assays, three Cry1Ac1 variants were selected for diet bioassays with *T. ni* and *C. includens*. These variants are listed in Table 6. Diet bioassays were performed with Bt spore/crystal mixtures isolated from sporulated and lysed Bt cultures.

TABLE 6

Stabilized consensus Cry1Ac1 amino acid sequence variants selected for insect bioassay testing.

| Stabilized Cry1Ac1 variant | Mutations in Cry1Ac1 |
|---|---|
| Cry1Ac1_C05_Y384D_C404S | C15W, T304N, A344E, T361I, E461K, N463S, S582L |
| Cry1Ac1_C03_Y384D_C404S | C15W, F68S, G286D, T304N, M322K, E332G, A344E, Q353H, T361I, E461K, N463S, S582L |
| Cry1Ac1_A01_Y384D_C404S | E461K, N463S, T304N, A344E, T361I, S582L, C15W, M322K, Q353H |

Figures 17, 18:
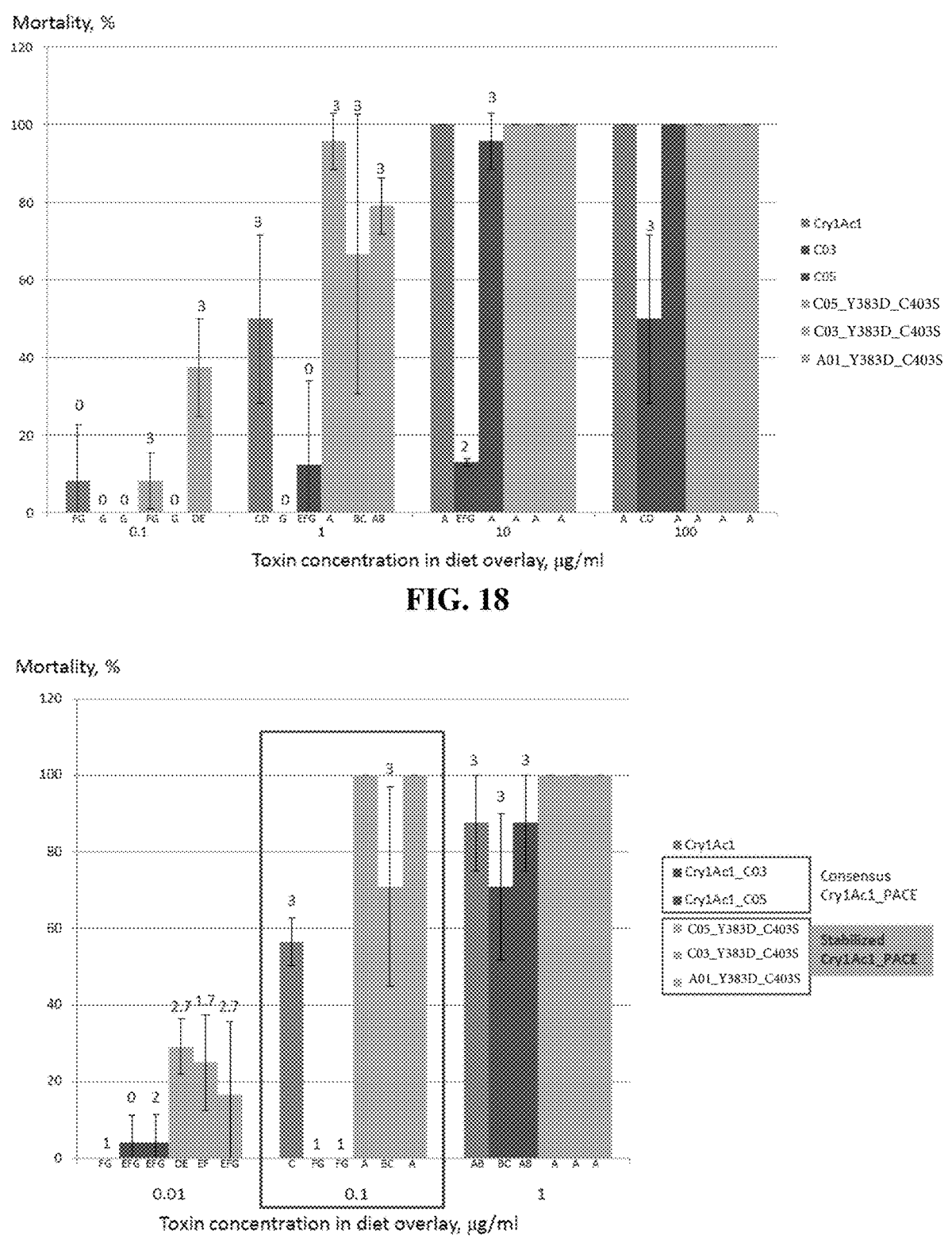
Figure 19:
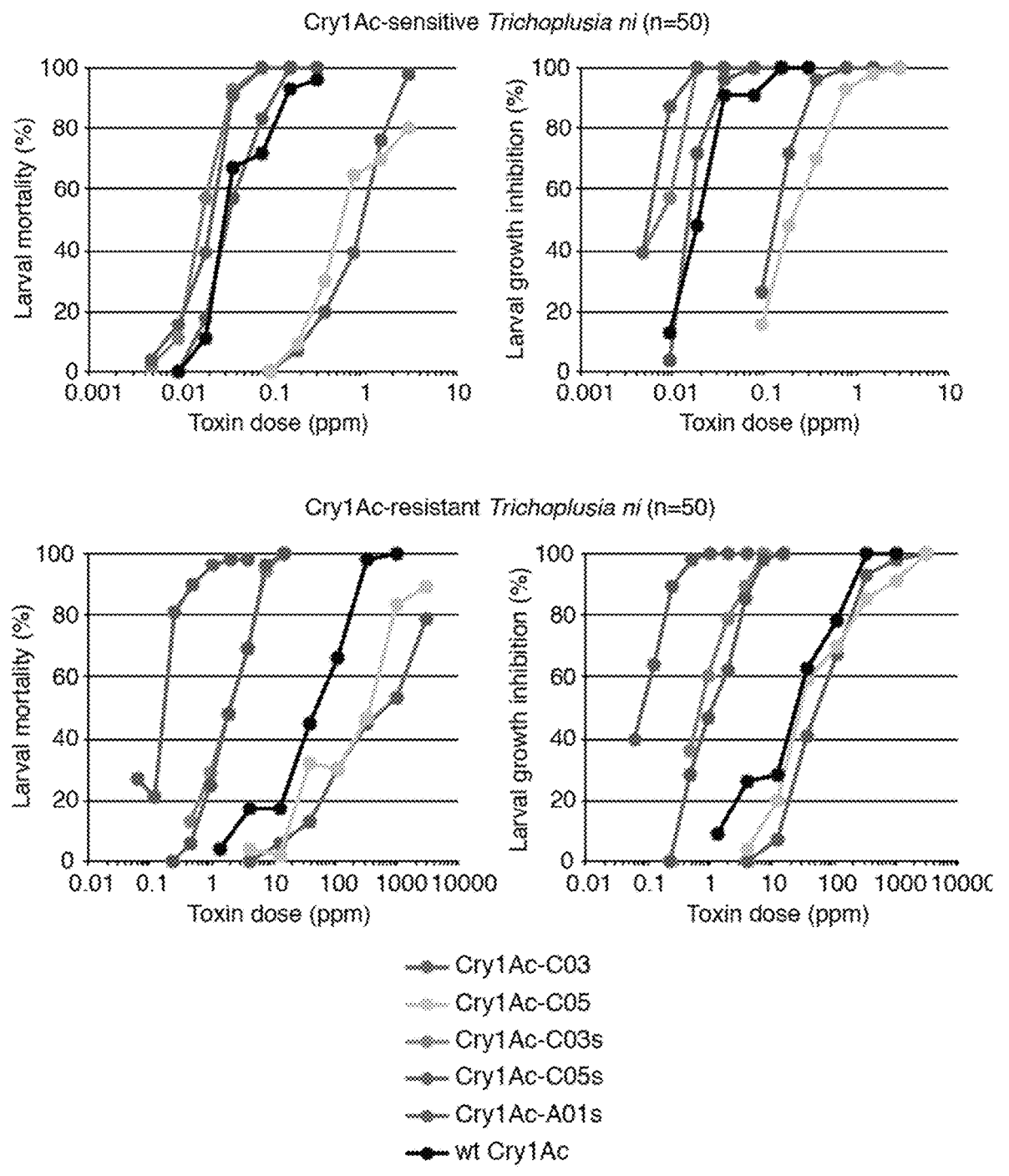

Results of diet bioassay with C. includens and T. ni are shown in FIGS. 17-19 and in Table 7, illustrating the activity (mortality and growth inhibition) of stabilized consensus PACE-evolved Cry1Ac1 variants (sucrose gradient purified Bt crystals) in diet bioassay. Numbers above bars in FIGS. 17 and 18 are stunting scores (maximum stunting score—3). Letters below bars are for mortality T-grouping.

Figure 22:
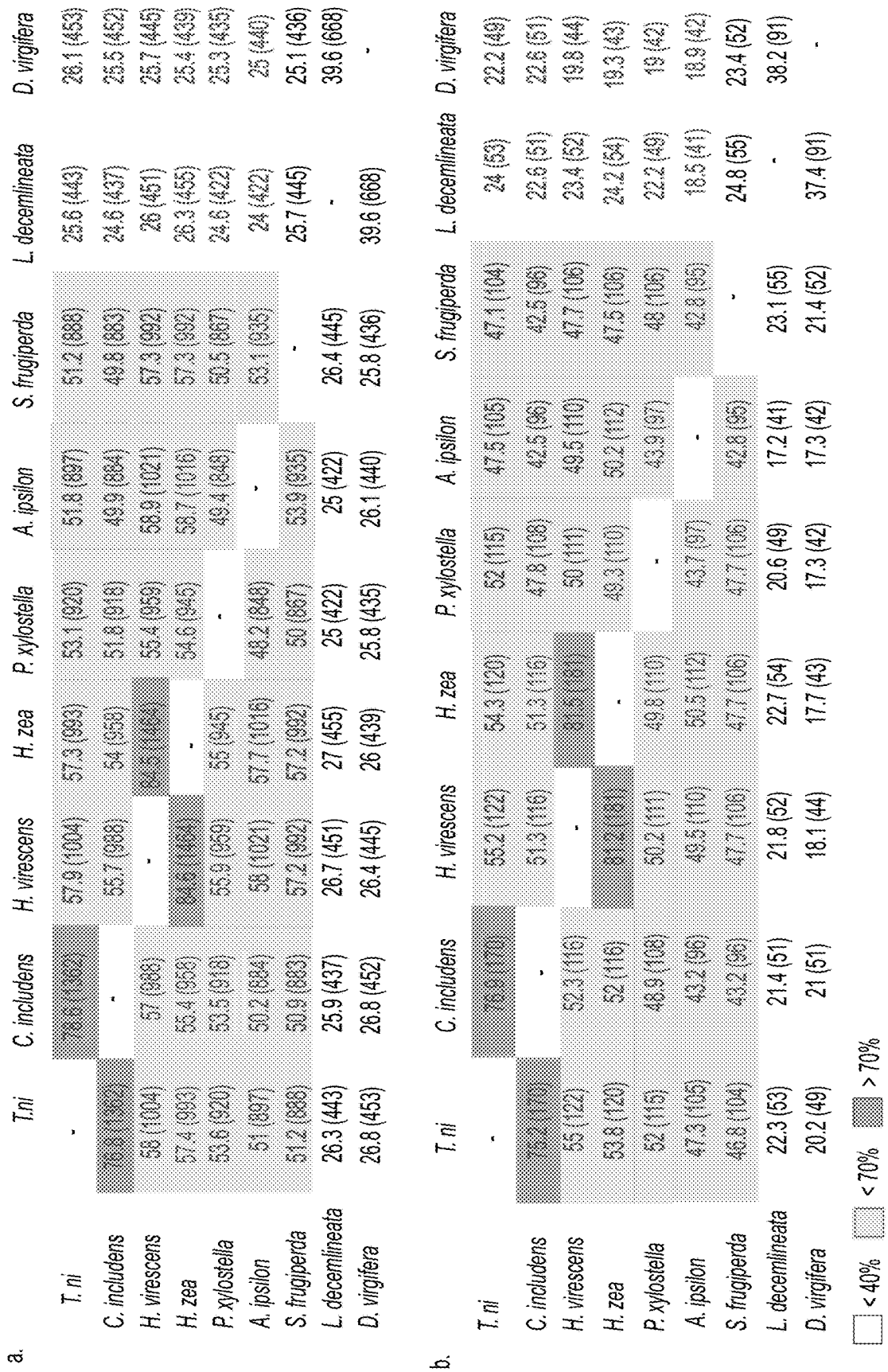
FIG. 22 shows comparison of cadherin receptor sequence identity. The % sequence identity using the full-length cadherin receptor (top) or fragment used for directed evolution experiments (bottom) for insects tested in FIG. 21. Numbers in parenthesis denote the number of identical amino acids between the two receptors. Mortality and stunting data from diet bioassays correlates with cadherin receptor sequence identity.

To characterize the species profile of their insecticidal activity, the evolved Cry1Ac variants were tested in diet bioassays on 11 additional agricultural pests: a lepidopteran related to T. ni (Chrysodeixis includes, soybean looper) that encodes a cadherin-like receptor highly homologous to TnCAD, eight more distantly related lepidopteran pests (Heliothis virescens, tobacco budworm; Helicoverpa zea, corn earworm; Plutella xylostella, diamondback moth; Agrotis ipsilon, black cutworm; Spodoptera frugiperda, fall armyworm; Anticarsia gemmatalis, velvetbean caterpillar; Diatraea saccharalis, sugarcane borer; and Spodoptera eridania, southern armyworm), and three non-lepidopteran pests (Leptinotarsa decemlineata, Colorado potato beetle; Lygus lineolaris, tarnished plant bug; and Diabrotica virgifera, western corn rootworm) (FIG. 21 and FIG. 22). Data indicates that the stabilized evolved Cry1Ac variants were more potent than wild-type Cry1Ac against C. includes, and comparably potent as wild-type Cry1Ac against the other lepidopteran pests assayed (FIG. 21). Neither the evolved nor wild-type Cry1Ac exhibited insecticidal activity against the lepidopteran S. eridania or the three non-lepidopterans tested. These results further support the mechanism of action of the PACE-evolved Bt toxins as binding to the cadherin receptor in T. ni and the related cadherin receptor in C. includes, while retaining binding to native receptors in all tested lepidopteran species. These data also reveal that the evolved Bt toxins did not acquire activity against species lacking a receptor homologous to TnCAD. Taken together, these findings demonstrate that an evolved Bt toxin that binds a novel target can potently kill closely related insect pest species, while maintaining a similar overall insect spectrum specificity as the parental Bt toxin.

As evident from the data presented herein, stabilized Cry1Ac1 variants are not only much more active than consensus PACE-evolved variants, but also more active than the wild-type Cry1Ac1.

TABLE 7

Insecticidal activity of PACE-evolved and stabilized variants against Cry1Ac-resistant and susceptible T. ni.

| | | Toxin | LC50 | 95% CL | Slope | SE | Relative potency (%) |
|---|---|---|---|---|---|---|---|
| Susceptible T. ni | Response: Mortality | Cry1Ac | 0.039 | 0.019-0.069 | 2.54 | 0.26 | 100 |
| | | Protein 1 | 0.793 | 0.505-1.082 | 2.84 | 0.41 | 5 |
| | | Protein 2 | 0.715 | 0.407-1.176 | 1.78 | 0.22 | 5 |
| | | Protein 3 | 0.035 | 0.026-0.045 | 3.59 | 0.41 | 111 |
| | | Protein 4 | 0.018 | 0.014-0.020 | 4.68 | 0.75 | 217 |
| | | Protein 5 | 0.021 | 0.015-0.024 | 4.82 | 1.09 | 186 |
| | Response: growth inhibition | Cry1Ac | 0.019 | 0.011-0.027 | 3.09 | 0.39 | 100 |
| | | Protein 1 | 0.136 | 0.110-0.160 | 4.00 | 0.62 | 14 |
| | | Protein 2 | 0.217 | 0.167-0.268 | 2.59 | 0.32 | 9 |
| | | Protein 3 | 0.016 | 0.014-0.018 | 5.53 | 0.82 | 119 |
| | | Protein 4 | 0.007 | 0.003-0.010 | 3.65 | 0.61 | 271 |
| | | Protein 5 | 0.005 | 0.004-0.006 | 4.92 | 0.90 | 380 |
| Cry1Ac resistant T. ni | Response: Mortality | Cry1Ac | 51.229 | 9.929-90.241 | 1.89 | 0.36 | 100 |
| | | Protein 1 | 408.713 | 263.629-680.973 | 0.81 | 0.10 | 13 |
| | | Protein 2 | 235.698 | 79.467-510.323 | 1.12 | 0.15 | 22 |
| | | Protein 3 | 1.938 | 1.550-2.352 | 2.55 | 0.29 | 2643 |
| | | Protein 4 | 1.841 | 1.390-2.312 | 2.25 | 0.28 | 2783 |
| | | Protein 5 | 0.153 | 0.046-0.289 | 2.01 | 0.22 | 33483 |
| | Response: growth inhibition | Cry1Ac | 23.402 | 4.587-46.512 | 1.49 | 0.25 | 100 |
| | | Protein 1 | 56.626 | 40.600-75.685 | 1.84 | 0.21 | 41 |
| | | Protein 2 | 47.232 | 20.236-90.729 | 1.16 | 0.12 | 50 |
| | | Protein 3 | 1.116 | 0.797-1.484 | 2.19 | 0.23 | 2097 |
| | | Protein 4 | 0.733 | 0.515-0.949 | 2.06 | 0.28 | 3193 |
| | | Protein 5 | 0.083 | 0.061-0.104 | 2.57 | 0.38 | 28195 |

SEQUENCES

It will be understood that the sequences provided herein are exemplary and that they are disclosed herein to illustrate some embodiments of the present disclosure. They are neither meant to be limiting to the disclosure, nor to limit the meaning of the terms "Cry1Ac" or "cadherin." Those of ordinary skill in the art will understand that the sequences provided herein are exemplary only and will be able to ascertain additional suitable sequences, e.g., homologs and orthologs of B. thuringiensis Cry1Ac and Trichoplusia ni cadherin in B. thuringiensis and Trichoplusia ni as well as in other species.

*B. thuringiensis* Cry1Ac; GenBank Accession No. AY730621
(residues 2-609)

(SEQ ID NO: 1)
DNNPNINECIPYNCLSNPEVEVLGGERIETGYTPIDISLSLTQFLLSEFVPGAGFVLGLV

DIIWGIFGPSQWDAFLVQIEQLINQRIEEFARNQAISRLEGLSNLYQIYAESFREWEADP

TNPALREEMRIQFNDMNSALTTAIPLFAVQNYQVPLLSVYVQAANLHLSVLRDVSVFGQR

WGFDAATINSRYNDLTRLIGNYTDYAVRWYNTGLERVWGPDSRDWVRYNQFRRELTLTVL

DIVALFPNYDSRRYPIRTVSQLTREIYTNPVLENFDGSFRGSAQGIERSIRSPHLMDILN

SITIYTDAHRGYYYWSGHQIMASPVGFSGPEFTFPLYGTMGNAAPQQRIVAQLGQGVYRT

LSSTLYRRPFNIGINNQQLSVLDGTEFAYGTSSNLPSAVYRKSGTVDSLDEIPPQNNNVP

PRQGFSHRLSHVSMFRSGFSNSSVSIIRAPMFSWIHRSAEFNNIIASDSITQIPAVKGNF

LFNGSVISGPGFTGGDLVRLNSSGNNIQNRGYIEVPIHFPSTSTRYRVRVRYASVTPIHL

NVNWGNSSIFSNTVPATATSLDNLQSSDFGYFESANAFTSSLGNIVGVRNFSGTAGVIID

RFEFIPVT (Domain 1: 1-275 (pore formation); Domain 2: 276-463 (receptor binding); Domain 3: 464-609 (sugar binding)

RpoZ-Cry1Ac1_1 fusion-amino acid sequence (SEQ ID NO: 3)
MARVTVQDAV EKIGNRFDLV LVAARRARQM QVGGKDPLVP EENDKTTVIA LREIEEGLIN

NQILDVRERQ EQQEQEAAEL QAVTAIAEGR RAAAEQKLIS EEDLDNNPNI NECIPYNCLS

NPEVEVLGGE RIETGYTPID ISLSLTQFLL SEFVPGAGFV LGLVDIIWGI FGPSQWDAFL

VQIEQLINQR IEEFARNQAI SRLEGLSNLY QIYAESFREW EADPTNPALR EEMRIQFNDM

NSALTTAIPL FAVQNYQVPL LSVYVQAANL HLSVLRDVSV FGQRWGFDAA TINSRYNDLT

RLIGNYTDYA VRWYNTGLER VWGPDSRDWV RYNQFRRELT LTVLDIVALF PNYDSRRYPI

RTVSQLTREI YTNPVLENFD GSFRGSAQGI ERSIRSPHLM DILNSITIYT DAHRGYYYWS

GHQIMASPVG FSGPEFTFPL YGTMGNAAPQ QRIVAQLGQG VYRTLSSTLY RRPFNIGINN

QQLSVLDGTE FAYGTSSNLP SAVYRKSGTV DSLDEIPPQN NNVPPRQGFS HRLSHVSMFR

SGFSNSSVSI IRAPMFSWIH RSAEFNNIIA SDSITQIPAV KGNFLFNGSV ISGPGFTGGD

LVRLNSSGNN IQNRGYIEVP IHFPSTSTRY RVRVRYASVT PIHLNVNWGN SSIFSNTVPA

TATSLDNLQS SDFGYFESAN AFTSSLGNIV GVRNFSGTAG VIIDRFEFIP VT*

RpoZ-Cry1Ac1 nucleotide sequence (SEQ ID NO: 4)
atggcacgcgtaactgttcaggacgctgtagagaaaattggtaaccgttttgacctggtactggtc gccgcgcgtcgcgctcgtcagatgcaggtaggcggaaaggatccgctggtaccggaagaaaacgat aaaaccactgtaatcgcgctgcgcgaaatcgaagaaggtctgatcaacaaccagatcctcgacgtt cgcgaacgccaggaacagcaagagcaggaagccgctgaattacaagccgttaccgctattgctgaa ggtcgtcgtgcggccgcggaacaaaagcttatttctgaagaggacttgGATAACAATCCGAACATCA

ATGAATGCATTCCTTATAATTGTTTAAGTAACCCTGAAGTAGAAGTATTAGGTGGAGAAAGAATAGAA

ACTGGTTACACCCCAATCGATATTTCCTTGTCGCTAACGCAATTTCTTTTGAGTGAAT

TTGTTCCCGGTGCTGGATTTGTGTTAGGACTAGTTGATATAATATGGGGAATTTTTGG

TCCCTCTCAATGGGACGCATTTCTTGTACAAATTGAACAGTTAATTAACCAAAGAAT

AGAAGAATTCGCTAGGAACCAAGCCATTTCTAGATTAGAAGGACTAAGCAATCTTT

ATCAAATTTACGCAGAATCTTTTAGAGAGTGGGAAGCAGATCCTACTAATCCAGCAT

TAAGAGAAGAGATGCGTATTCAATTCAATGACATGAACAGTGCCCTTACAACCGCT

ATTCCTCTTTTTGCAGTTCAAAATTATCAAGTTCCTCTTTTATCAGTATATGTTCAAG

-continued

```
CTGCAAATTTACATTTATCAGTTTTGAGAGATGTTTCAGTGTTTGGACAAAGGTGGG

GATTTGATGCCGCGACTATCAATAGTCGTTATAATGATTTAACTAGGCTTATTGGCA

ACTATACAGATTATGCTGTACGCTGGTACAATACGGGATTAGAACGTGTATGGGGAC

CGGATTCTAGAGATTGGGTAAGGTATAATCAATTTAGAAGAGAATTAACACTAACT

GTATTAGATATCGTTGCTCTGTTCCCGAATTATGATAGTAGAAGATATCCAATTCGA

ACAGTTTCCCAATTAACAAGAGAAATTTATACAAACCCAGTATTAGAAAATTTTGAT

GGTAGTTTTCGAGGCTCGGCTCAGGGCATAGAAAGAAGTATTAGGAGTCCACATTTG

ATGGATATACTTAACAGTATAACCATCTATACGGATGCTCATAGGGGTTATTATTAT

TGGTCAGGGCATCAAATAATGGCTTCTCCTGTAGGGTTTTCGGGGCCAGAATTCACT

TTTCCGCTATATGGAACTATGGGAAATGCAGCTCCACAACAACGTATTGTTGCTCAA

CTAGGTCAGGGCGTGTATAGAACATTATCGTCCACTTTATATAGAAGACCTTTTAAT

ATAGGGATAAATAATCAACAACTATCTGTTCTTGACGGGACAGAATTTGCTTATGGA

ACCTCCTCAAATTTGCCATCCGCTGTATACAGAAAAAGCGGAACGGTAGATTCGCTG

GATGAAATACCGCCACAGAATAACAACGTGCCACCTAGGCAAGGATTTAGTCATCG

ATTAAGCCATGTTTCAATGTTTCGTTCAGGCTTTAGTAATAGTAGTGTAAGTATAATA

AGAGCTCCTATGTTCTCTTGGATACATCGTAGTGCTGAATTTAATAATATAATTGCAT

CGGATAGTATTACTCAAATCCCTGCAGTGAAGGGAAACTTTCTTTTTAATGGTTCTGT

AATTTCAGGACCAGGATTTACTGGTGGGACTTAGTTAGATTAAATAGTAGTGGAAA

TAACATTCAGAATAGAGGGTATATTGAAGTTCCAATTCACTTCCCATCGACATCTAC

CAGATATCGAGTTCGTGTACGGTATGCTTCTGTAACCCCGATTCACCTCAACGTTAA

TTGGGGTAATTCATCCATTTTTTCCAATACAGTACCAGCTACAGCTACGTCATTAGAT

AATCTACAATCAAGTGATTTTGGTTATTTTGAAAGTGCCAATGCTTTTACATCTTCAT

TAGGTAATATAGTAGGTGTTAGAAATTTTAGTGGGACTGCAGGAGTGATAATAGAC

AGATTTGAATTTATTCCAGTTACTtaa
```

*Trichoplusia ni* cadherin, GenBank Accession No. AEA29692
(residues 1133-1582).
(SEQ ID NO: 2)

```
AGNTFRLSREQSTVNGVLVRVDGQSFPRVSATDEDGLHAGSVSFSVVGAAAEYFSMRN

FEDNTGELYLSQPLPLEDDGFDITIRGSDAGTEPGSLFSEVSFRLVFVPTHGDPVFSVSQY

TVAFIEKEAGLLESHQLPRAVDPKNYMCEEMNEPCHEIYYSIIDNNEEGYFQVDSTTNVI

SLSRELERASQASHVVRVAASNTLLDPAAPPPLLPSSTFLLTINVREADPRPVFEREIYTA

GIYETDTSNRELLTVHATHTEGLDITYTMDLDTMVVDPSLEGVRESAFTLHPSSGVLSLN

MNPLDTMVGMFEFDVVATDTRGAEARTDVKIYLITHLNRVYFLFNNTLDVVDSNRAFI

ADTFSSVFSLTCNIDAVLRAPDSSGAARDDRTEVRAHFIRNHVPATTDEIEQLRSNTILLR

AIQETLLTRELHLEDFVGGSSPELGVDNSLT
```

*Trichoplusia ni* cadherin Fragment 3 of CAD3 (wild-type) amino acid
sequence
(SEQ ID NO: 5)

```
RPVFEREIYTAGIYETDTSNRELLTVHATHTEGLDITYTMDLDTMVVDPSLEGVRESAFT

LHPSSGVLSLNMNPLDTMVGMFEFDVVATDTRGAEARTDVKIYLITHLNRVYFLFNNTL

DVVDSNRAFIADTFSSVFSLTCNIDAVLRAPDSSGAARDDRTEVRAHFIRNHVPATTDEI

EQLRSNTILLRAIQETLLTRELHLEDFVGGSSPELGVDNSLT*
```

-continued

*Trichoplusia ni* cadherin Fragment 3 of TBR3 mutant amino acid sequence
(SEQ ID NO: 6)

```
RPVFEREIYTAGIYETDTSNRELLTVHATHTEGLDITYTMDLDTMVVDPSLEGVRESAFT

LHPSSGVLSLNFNPSATMVGMFEFDVVATDTRGAEARTDVKIYLITHLNRVYFLFNNTL

DVVDSNRAFIADTFSSVFSLTCNIDAVLRAPDSSGAARDDRTEVRAHFIRNHVPATTDEI

EQLRSNTILLRAIQETLLTRELHLEDFVGGSSPELGVDNSLT*
```

EQUIVALENTS AND SCOPE, INCORPORATION BY REFERENCE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A pesticidal protein comprising an amino acid sequence that is at least 98% identical to SEQ ID NO: 1, wherein the protein comprises at least one of the following amino acid substitutions: I6V, E8D, E8K, C9Y, C9F, C9R, I10L, Y12S, N135, C14W, C14R, L155, S16R, S16G, P18T, P18H, V22A, V22L, G24D, G24S, G25R, E26K, E26G, R27S, I28T, E29K, E29A, T30A, T301, G31V, G31D, Y32C, Y32S, T33A, L76F, T212A, G281S, N371Y, Q423P, S488L, T536N, I37S, I37T, S40L, S47N, V50I, V50G, V50A, G52S, A53V, V60A, D61N, I62V, I62T, 162K, I63V, I63M, I63T, I66T, I66V, F67S, F67L, P69S, P69T, 570F, A74T, A74V, I79V, I79T, I79L, E80G, I83T, N84D, Q85R, E88G, E88A, E89G, E89D, A91T, R92K, N93T, N93D, N93S, S97Y, S97F, E100G, E100I, G101R, G101V, 1108V, 1108T, E111G, S112Y, E115K, E117D, E117G, A118T, A1185, P120L, P120S, T121A, N122S, P123S, A124E, A124S, A124V, L125S, E127K, E127A, E128K, M1291, I131V, Q132R, M1361, N137S, N137D, S138G, S138N, A139T, A139V, T141A, T142P, T142A, T142S, A143T, A143D, P145S, V149A, N151D, Y152H, V154A, Y160H, V1611, A163T, V176M, V176A, R180K, R180G, D184N, A186V, A186S, A186E, T187A, 5190R, 5190G, R191C, N193D, D194N, T196A, R197K, R197G, L1981, G200V, N201H, N201S, Y202H, A206V, V2071, R208L, R208H, Y210F, Y210S, E215D, R216S, V2171, V217A, D224N, D224Y, Y228H, V243I, A244S, P247L, S251N, R252K, R253K, R253I, E265K, N269S, E273A, N274D, S278N, F279I, G281C, G281D, S282L, Q284R, G285D, G285V, R288G, I290L, S292N, S292G, N300L, S301G, S301R, 1302V, 1302M, T303N, T303K, 1304V, A308T, H309Y, G311D, Y312C, Y312H, Y312?, Y313C, Q319R, I320L, M321K, A322S, S323A, F327Y, S328L, E331G, P335S, M340V, N342T, A343E, A344V, A344T, A344D, P345L, Q346K, Q346R, I349V, A351V, A351T, Q352H, R359K, T360I, L361F, L361T, S362P, S362L, T364I, T364S, R368S, R368K, N371S, I372T, I372L, I374T, I374L, I374M, N375K, D383Y, T385A, E386D, A388T, N394S, N394T, N394I, K402R, S403C, S403F, S403N, S403I, T405M, V406A, L409M, D410G, I412V, P414T, N418S, P420L, R422K, R436H, F439L, S442G, S442I, S443G, V444I, S445N, I446V, F452C, I455V, I455M, E460K, E460G, N462S, A466T, A475V, V476M, N479K, F480L, F480S, F480C, V486I, I487V, P490S, T493I, S502R, N505H, N505D, R510K, R510G, Y512C, Y512S, E514G, E514K, E514D, V515I, I517V, I517R, T522I, T522P, S523P, R525K, V528I, V530I, A533V, V535A, V535I, H539Y, N541S, V542I, N543D, N543S, N543K, N546S, N546D, N546T, S547L, S548P, I549V, T553I, P555S, A556V, A558S, A558T, T559M, S560L, N563D, Q565R, S566L, D568N, Y571H, Y571F, F572L, E573G, A575T, A575S, A577T, A577V, A577D, T579A, S581L, G587S, G587D, V588I, R589G, R589K, N590S, N590H, F591S, G593R, T594I, T594P, A595V, I598V, I598R, I605L, V607A, V607S, S580Y, F75L, N211D, V325A, N371T, Q423K, S488P, T536A, and S580F.

2. The pesticidal protein of claim 1, wherein the protein comprises at least 2 of the amino acid substitutions.

3. The pesticidal protein of claim 1, wherein at least one amino acid substitution is located between amino acid residues 275-462 of SEQ ID NO: 1.

4. The pesticidal protein of claim 1, wherein the protein comprises at least one amino acid substitution selected from C14W, C14R, F67S, R197G, N371T, T303N, M321K, E331G, A343E, Q352H, T360I, S362P, E460K, N462S, D383Y, S403C, and S581L.

5. The pesticidal protein of claim 1, wherein the protein does not comprise an amino acid substitution at the residue corresponding to residue D383 of SEQ ID NO: 1 or at the residue corresponding to residue S403 of SEQ ID NO: 1.

6. The pesticidal protein of claim 1, wherein the protein comprises the wild-type amino acid at the residue corresponding to D383 of SEQ ID NO: 1 and at the residue corresponding to S403 of SEQ ID NO: 1.

7. The pesticidal protein of claim 1, wherein the protein comprises the following amino acid substitutions E460K, N462S, T303N, A343E, T360I, S581L, C14W, M321K, and Q352H.

8. The pesticidal protein of claim 1, wherein the protein comprises the following amino acid substitutions E460K, N462S, T303N, A343E, T360I, S581L, C14W, M321K, Q352H, F67S, G285D, and E331G.

9. A pesticidal protein comprising a receptor binding domain that comprises an amino acid sequence that is at least about 92% identical to amino acid residues 275-462 as set forth in SEQ ID NO: 1, wherein the receptor binding domain comprises at least one of the following amino acid substitutions: G285D, I372T, F439L, G285V, P335S, I372L, S442G, M340V, I374T, S442I, I290L, I374L, S443G, S292N, I374M, V444I, S292G, N342T, N375K, S445N, N300L, A343E, D383Y, I446V, S301G, A344V, T385A, F452C, S301R, A344T, E386D, I455V, I302V, A344D, A388T, I455M, I302M, P345L, N394S, E460K, T303N, Q346K, N394T, E460G, T303K, Q346R, N394I, N462S, I304V, I349V, K402R, A308T, A351V, S403C, H309Y, A351T, S403F, G311D, Q352H, S403I, Y312C, R359K, T405M, Y312H, T360I, V406A, L361F, L409M, Y313C, L361T, D410G, Q319R, S362P, I412V, I320L, S362L, P414T, S278N, M321K, T364I, F279I, A322S, T364S, N418S, G281S, S323A, R368S, P420L, G281C, V325A, R368K, R422K, G281D, F327Y, N371S, and Q423K.

10. The pesticidal protein of claim 9, wherein the protein comprises at least one amino acid substitution selected from T303N, M321K, E331G, A343E, Q352H, T360I, S362P, E460K, and N462S.

11. A pesticidal composition comprising an amount of the protein of claim 1 that is effective to kill a Lepidoptera insect pest, wherein the insect is sensitive to treatment with a protein represented by SEQ ID NO: 1.

12. A recombinant cell comprising a pesticidally effective amount of the protein of claim 1, wherein said protein is expressed in said cell from a recombinant DNA construct operably linked to a promoter functional in said cell.

13. A plant comprising the recombinant cell of claim 12.

14. The plant of claim 13, wherein the plant expresses a pesticidally effective amount of the pesticidal protein.

15. A method of pest control, the method comprising providing to a pest the protein of claim 1.

16. The pesticidal protein of claim 1, wherein the at least one amino acid substitution is introduced at an amino acid position selected from the group consisting of C14, F67, R197, G267, T303, M321, E331, A343, Q352, T360, S362, E460, N462, D486, S506, and S581.

17. The pesticidal protein of claim 1, wherein the at least one amino acid substitution is introduced at an amino acid position selected from the group consisting of E460, N462, T303, A343, T360, S581, C14, M321, and Q352.

18. The pesticidal protein of claim 1, wherein the protein comprises an amino acid substitution at a residue selected from the group consisting of E460, N462, T303, A343, T360, S581, C14, M321, Q352, F67, G285, and E331.

19. The pesticidal protein of claim 1, wherein the protein comprises the amino acid substitution selected from the group consisting of E460K, N462S, T303N, A343E, T360I, S581L, C14W, M321K, Q352H, F67S, G285D, and E331G.

20. The pesticidal protein of claim 9, wherein the protein binds a receptor in a target pest with greater affinity than a protein represented by SEQ ID NO: 1.

* * * * *

UNITED STATES PATENT AND TRADEMARK OFFICE
CERTIFICATE OF CORRECTION

PATENT NO. : 11,524,983 B2
APPLICATION NO. : 15/217839
DATED : December 13, 2022
INVENTOR(S) : David R. Liu et al.

It is certified that error appears in the above-identified patent and that said Letters Patent is hereby corrected as shown below:

In the Claims

Claim 1, Column 67, Line 55, the text: "N13S, C14W, C14R, L15S, S16R, S16G, P18T, P18H" should be replaced with --N13S, C14W, C14R, L15S, S16R, S16G, P18T, P18H--.

Claim 1, Column 67, Line 57, the text: "T30I" should be replaced with --T30I--.

Claim 1, Column 67, Line 60, the text: "I62K" should be replaced with --I62K--.

Claim 1, Column 67, Line 61, the text: "S70F" should be replaced with --S70F--.

Claim 1, Column 67, Line 64, the text: "S97Y, S97F, E100G, E100I, G101R, G101V, 1108V, 1108T" should be replaced with --S97Y, S97F, E100G, E100I, G101R, G101V, I108V, I108T--.

Claim 1, Column 67, Line 65, the text: "A118S" should be replaced with --A118S--.

Claim 1, Column 67, Line 67, the text: "M129I" should be replaced with --M129I--.

Claim 1, Column 68, Line 50, the text: "M136I" should be replaced with --M136I--.

Claim 1, Column 68, Line 52, the text: "V161I" should be replaced with --V161I--.

Claim 1, Column 68, Line 54, the text: "S190R, S190G" should be replaced with --S190R, S190G--.

Claim 1, Column 68, Line 55, the text: "L198I" should be replaced with --L198I--.

Claim 1, Column 68, Line 56, the text: "V207I" should be replaced with --V207I--.

Claim 1, Column 68, Line 57, the text: "V217I" should be replaced with --V217I--.

Signed and Sealed this
Seventh Day of February, 2023

Katherine Kelly Vidal
*Director of the United States Patent and Trademark Office*

CERTIFICATE OF CORRECTION (continued)
U.S. Pat. No. 11,524,983 B2

Claim 1, Column 68, Line 61, the text: "1302V" should be replaced with --I302V--.

Claim 1, Column 68, Line 62, the text: "1302M, T303N, T303K, 1304V, A308T, H309Y, G311D" should be replaced with --I302M, T303N, T303K, I304V, A308T, H309Y, G311D--.

Claim 1, Column 68, Line 63, the text: "Y312?" should be replaced with --Y312Δ--.

Claim 1, Column 69, Line 3, the text: "N394I, K402R, 5403C, 5403F, 5403N, 54031, T405M" should be replaced with --N394I, K402R, S403C, S403F, S403N, S403I, T405M--.

Claim 1, Column 69, Line 5, the text: "54421" should be replaced with --S4421--.

Claim 1, Column 69, Line 9, the text: "Y5125" should be replaced with --Y512S--.

Claim 1, Column 69, Line 13, the text: "P5555" should be replaced with --P555S--.

Claim 1, Column 69, Line 14, the text: "A5585" should be replaced with --A558S--.

Claim 1, Column 69, Line 15, the text: "A5755" should be replaced with --A575S--.

Claim 1, Column 69, Line 19, the text: "V6075" should be replaced with --V607S--.

Claim 5, Column 69, Line 34, the text: "5403" should be replaced with --S403--.

Claim 6, Column 69, Line 38, the text: "5403" should be replaced with --S403--.

Claim 9, Column 70, Line 7, the text: "5403C" should be replaced with --S403C--.

Claim 16, Column 70, Line 35, the text: "5362" should be replaced with --S362--.

Claim 17, Column 70, Line 39, the text: "5581" should be replaced with --S581--.